(12) United States Patent
Schaebitz et al.

(10) Patent No.: US 7,785,601 B2
(45) Date of Patent: Aug. 31, 2010

(54) METHODS OF TREATING NEUROLOGICAL CONDITIONS WITH HEMATOPOIETIC GROWTH FACTORS

(75) Inventors: Wolf-Ruediger Schaebitz, Dossenheim (DE); Armin Schneider, Heidelberg (DE); Carola Krueger, Speyer (DE); Clemens Sommer, Guenzburg (DE); Stefan Schwab, Heidelberg (DE); Rainer Kollmar, Heidelberg (DE); Martin Maurer, Heidelberg (DE); Daniela Weber, Mannheim (DE); Nikolaus Gassler, Heidelberg (DE)

(73) Assignee: Sygnis Bioscience GmbH & Co. KG, Heidelberg (DE)

( * ) Notice: Subject to any disclaimer, the term of this patent is extended or adjusted under 35 U.S.C. 154(b) by 849 days.

(21) Appl. No.: 10/659,295

(22) Filed: Sep. 11, 2003

(65) Prior Publication Data

US 2004/0141946 A1 Jul. 22, 2004

Related U.S. Application Data

(63) Continuation of application No. 10/331,755, filed on Dec. 31, 2002, now abandoned.

(51) Int. Cl.
*A61K 38/00* (2006.01)
*A61K 38/18* (2006.01)
*C07K 14/53* (2006.01)

(52) U.S. Cl. .................. 424/198.1; 514/2; 530/399
(58) Field of Classification Search .............. None
See application file for complete search history.

(56) References Cited

U.S. PATENT DOCUMENTS

| 4,810,643 | A | 3/1989 | Souza |
|---|---|---|---|
| 5,599,690 | A | 2/1997 | Fenton et al. |
| 2002/0151488 | A1 | 10/2002 | Lauffenburger et al. |
| 2002/0198150 | A1* | 12/2002 | Chajut .......................... 514/12 |
| 2004/0141946 | A1 | 7/2004 | Schaebitz et al. |
| 2004/0186052 | A1* | 9/2004 | Iyer et al. ...................... 514/12 |
| 2005/0142101 | A1 | 6/2005 | Forssmann et al. |
| 2005/0142102 | A1 | 6/2005 | Schaebitz et al. |

FOREIGN PATENT DOCUMENTS

| DE | 100 33 219 A1 | 1/2002 |
|---|---|---|
| EP | 0 327 545 B2 | 9/1987 |
| EP | 1 374 898 | 1/2002 |
| EP | 1 327 449 | 7/2003 |
| JP | 1992000357539 | 9/1991 |
| JP | 05246885 | 9/1993 |
| JP | 2002-530068 | 9/2002 |
| JP | 2002-281962 | 10/2002 |
| WO | WO 87/01132 | 2/1987 |
| WO | WO 99/17798 | 4/1999 |
| WO | WO 99/61445 | 12/1999 |
| WO | WO 99/61446 | 12/1999 |
| WO | WO 00/04926 | 2/2000 |
| WO | WO 00/44785 | 8/2000 |
| WO | WO 02/22163 A1 | 3/2002 |
| WO | WO 02/072144 A1 | 9/2002 |
| WO | 02/099081 | 12/2002 |
| WO | WO 02/099081 | 12/2002 |
| WO | 03/061685 | 7/2003 |

OTHER PUBLICATIONS

Wells, 1990, Biochemistry 29:8509-8517.*
Ngo et al., 1994, The Protein Folding Problem and Tertiary Structure Prediction, pp. 492-495.*
Bork, 2000, Genome Research 10: 398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Bath et al. Cochrane Database Syst Rev. 2006; 3: CD0005207: 1-13.*
Hagg et al. Int Clin Psychopharmacol. 2003; 18: 173-174.*
Siren et al. Eur Arch Psychiatry Clin Neurosci. 2001; 251: 179-184.*
del Zoppo GJ, Curr Opin Hematol. 2000; 7: 309-15.*
Emerich et al., Clin Pharmacokinet. 2001; 40: 105-23.*
Lu et al. Neurobiology of Disease. 2001; 8: 194-206.*
Bouma et al. Journal of Neurosurgery. 1992; 77: 360-368.*
MacVittie et al., Blood, 95(3):837-845, Feb. 1, 2000.*
NCBI protein accession No. P09919, the amino acid sequence for Filgrastim, published Jul. 1, 1989.*
Brines et al. PNAS, USA, 97(19): 10526-10531, Sep. 12, 2000.*
Deleuze et al., Intensive care Medicine, 26:1579-1580, Oct. 2000.*
Morita-Fujimura et al. Journal of Cerebral Blood Flow and Metabolism, 19(6): 634-642, Jun. 1999.*
Curran and Goa, Drugs 62(8): 1207-1213, May 15, 2002.*
Neupogen (Filgrastim) Product Label Insert, Amgen, published Apr. 2, 1998*
Whalen et al., Critical Care Medicine, 27(5):1014-1018, May 1999.*
Whalen et al. Crit Care Med. 28(11):3710-3717 (2000).*
Sakowitz et al. (Acta neurochirurgica. Supplement, 2006; 96: 139-43—abstract only.*
Whalen et al., Crit Care Med. 1999, 27: 1014-1018—HTML version only available; downloaded Dec. 21, 2009; 9 pages total.*
Sheibani et al., Crit Care Med. 2004; 32: 2274-2278.*

(Continued)

*Primary Examiner* — Bridget E Bunner
*Assistant Examiner* — Christina Borgeest
(74) *Attorney, Agent, or Firm* — Oblon, Spivak, McClelland, Maier & Neustadt, L.L.P.

(57) ABSTRACT

The present invention relates to a method of treating neurological conditions in a mammal by administering a hematopoietic growth factor such as granulocyte-colony stimulating factor (GCSF) and granulocyte-macrophage colony stimulating factor (GMCSF). The invention also provides methods of screening for compounds that bind to a GCSF or GMCSF receptor found on the surface of a neuronal cell; and which provides a neuroprotective, neuroproliferative and/or a STAT gene activation activity.

19 Claims, 27 Drawing Sheets

OTHER PUBLICATIONS

Marzban et al., European Journal of Neurology, 2009; 16 (Suppl. 3) 335-624; abstract P2765; 1 page.*

Modiry et al., European Journal of Neurology, 2009; 16 (Suppl. 3) 335-624; abstract P2766; 1 page.*

Tarkowski, et al, "Local and systemic GM-CSF increase in Alzheimer's disease and vascular dementia", Acta Neurol Scand, 2001:103: 166-174.

Tarkowski, et al., "Intrathecal release of pro- and anti-inflammatory cytokines during stroke", Clin Exp Immunol, 1997;110:492-499.

Tarkowski, et al., "Intrathecal Expression of Proteins Regulating Apoptisis in Acute Stroke", Apoptosis During Stroke, Feb. 1999.

Heard, et al., "Effect of prophylactic administration of recombinant human granulocyte colony-stimulating factor (filgrastim) on the frequency of nosocomial infections in patients with acute traumatic brain injury or cerebral hemorrhage", Crit Care Med, 1998, vol. 26, No. 4, pp. 748-754

Patterson, The emerging neuropoietic cytokine family: first CDF/LIF, CNTF and IL-6: next ONC, MGF, GCSF?, Current Biology, Ltd. vol. 2, No. 1, (1992).

Zavala, et al., "G-CSF Therapy of Ongoing Experimental Allergic Encephalomyelitis Via Chemokine- and Cytokine-Based Immune Deviation", Article by the American Association of Immunologists (2002), pp. 2011-2019.

Suzumara, et al., "Selective induction of interleukin-6 in mouse microglia by granulocyte-macrophage colony-stimulating factor", Brain Research, 713 (1996), pp. 192-198.

Lee, et al., "GM-CSF Promotes Proliferation of Human Fetal and Adult Microglia in Primary Cultures", GLIA 12:309-318 (1994).

Guillemin, et al., "Granulocyte Macrophage Colony Stimulating Factor Stimulates In Vitro Proliferation of Astrocytes Derived From Simian Mature Brains", GLIA, 16:71-80 (1996).

Dame, et al., "The Distribution of Granulocyte-Macrophage Colony-Stimulaing Factor and its Receptor in the Developing Human Fetus", Pediatric Research, vol. 46, No. 4, (1999), pp. 358-366.

Dame, et al., "The effect of interleukin-1β (II-1β) and tumor necrosis factor-α (TNF-α) on granulocyte macrophage-colony stimulating factor (GM-CSF) production by neuronal precursor cells", Eur. Cytokine Netw, vol. 13, No. 1, Mar. 2002, pp. 128-133.

Baldwin, et al., "Identification and Characterization of a High-Affinity Granulocyte-Macrophage Colony-Stimulating Factor Receptor on Primary Rat Oligodendrocytes", Blood, vol. 82, No. 11, Dec. 1, 1993, pp. 3279-3282.

Schaebitz W. R. et al: "Recombinant Granulocyte-Colony Stimulating Factor (RG-CSF) Is Neuroprotective Following Focal Transient Cerebral Ischemia and Excitotoxity" Society for Neuroscience Abstracts,Society for Neuroscience, US, vol. 27, No. Part 2, Nov. 10, 2001, p. 2027, AN76411, XP008009334, ISSN: 0190-5295 the whole document.

Konishi Y, et al.: "Trophic Effect of Erythropoietin and Other Hematopoietic Factors on Central Cholinergic Neurons In Vitro an In Vivo.", Brain Research, Apr. 23, 1993, vol. 609, Nos. 1-2, pp. 29-35, XP001183386 ISSN: 0006-8993, Abstract, Introduction, p. 29, Discussion pp. 32-34.

Hierholzer, et al., "Activation of Stat Proteins Following Ischemia Reperfusion Injury Demonstrates a Distinct IL-6 and G-CSF Mediated Profile.", Transplantation Proceedings, Sep. 1998. Vol. 30, No. 6, p. 2647, XP001182894, ISSN: 0041-1345 the whole document.

Tian Shin-Shay, et al.: "Multiple Signaling Pathways Induced by Granulocyte Colony-Stimulating Factor Involving Activation of JAKs, STAT5, and/or STAT3 are Required for Regulation of Three Distinct Classes of Immediate Early Genes" Blood, vol. 88, No. 12, 1996, pp. 4435-4444 XP001183387 ISSN: 0006-4971 the whole document.

Ward Alister, et al., "Tyrosine-Dependent and—Independent Mechanisms of STAT3 Activation by the Human Granulocyte Colony-Stimulating Factor (G-CSF) Receptor are Differentially Utilized Depending on G-CSF Concentration", Blood, vol. 93, No. 1, Jan. 1, 1999 pp. 113-124 XP001183113, ISSN: 0006-4971 the whole document.

Schaebitz, et al. "Neuroprotective Effect of Granulocyte Colony-Stimulating Factor After Focal Cerebral Ischemia.", Stroke, vol. 34, No. 3, Mar. 2003, pp. 745-751, XP002294803, ISSN: 0039-2399 the whole document.

International Preliminary Examination Report as received in corresponding PCTi/IB 03/06446 filed December 31, 2003 case.

U.S. Appl. No. 11/931,295, filed Oct. 31, 2007, Schaebitz, et al.
U.S. Appl. No. 10/331,755, filed Dec. 31, 2002, Schaebitz, et al.
U.S. Appl. No. 10/659,295, filed Sep. 11, 2003, Schaebitz, et al.
U.S. Appl. No. 10/880,101, filed Jun. 30, 2004, Schaebitz, et al.
U.S. Appl. No. 11/846,699, filed Aug. 29, 2007, Schaebitz, et al.
U.S. Appl. No. 11/930,758, filed Oct. 31, 2007, Schaebitz, et al.
U.S. Appl. No. 11/931,128, filed Oct. 31, 2007, Schaebitz, et al.
U.S. Appl. No. 11/931,326, filed Oct. 31,2007, Schaebitz, et al.
U.S. Appl. No. 11/931,618, filed Oct. 31, 2007, Schaebitz, et al.
U.S. Appl. No. 11/932,383, filed Oct. 31, 2007, Schaebitz, et al.

* cited by examiner

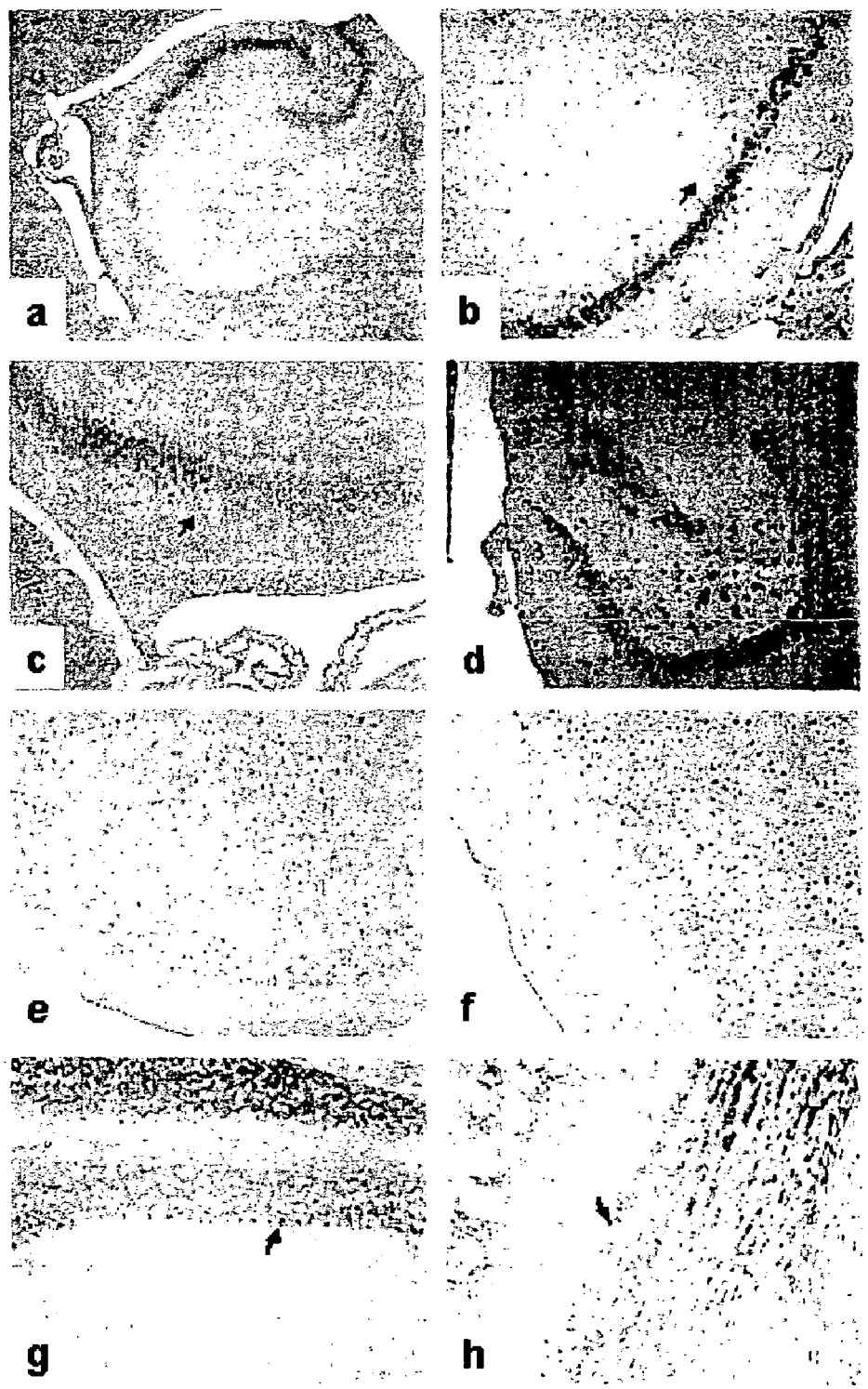
Figure 4, part I

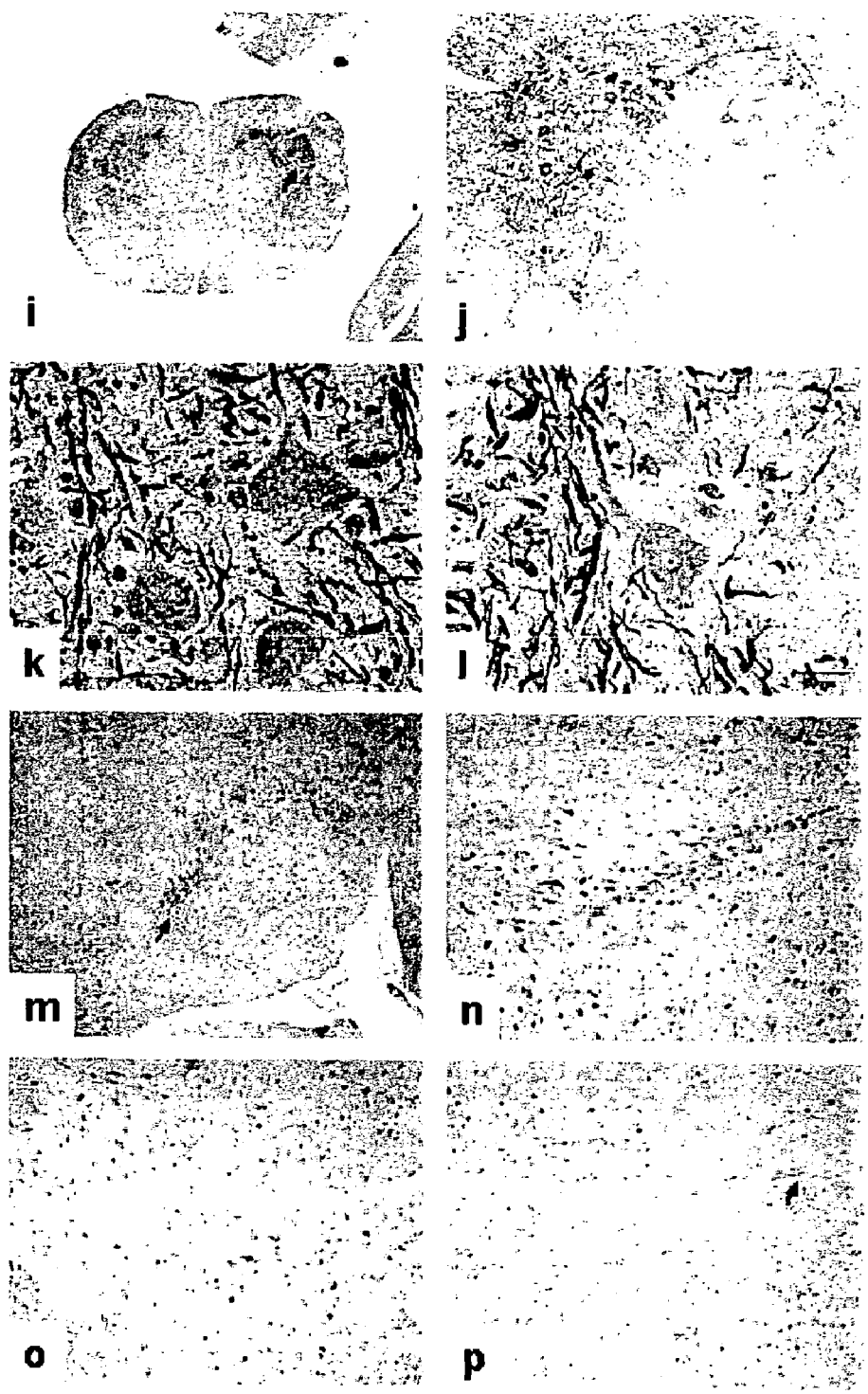
Figure 4, part II

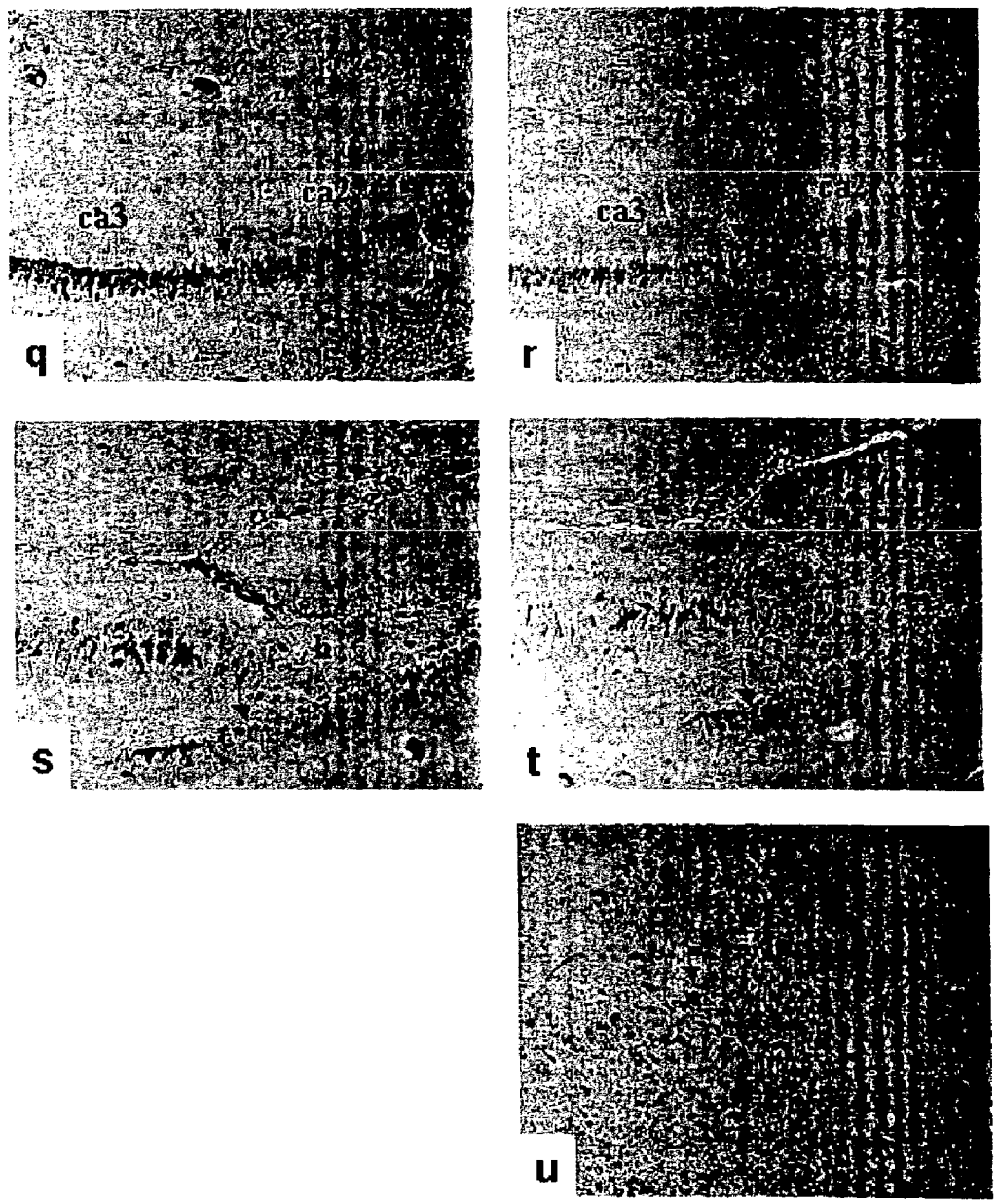
Figure 4, part III

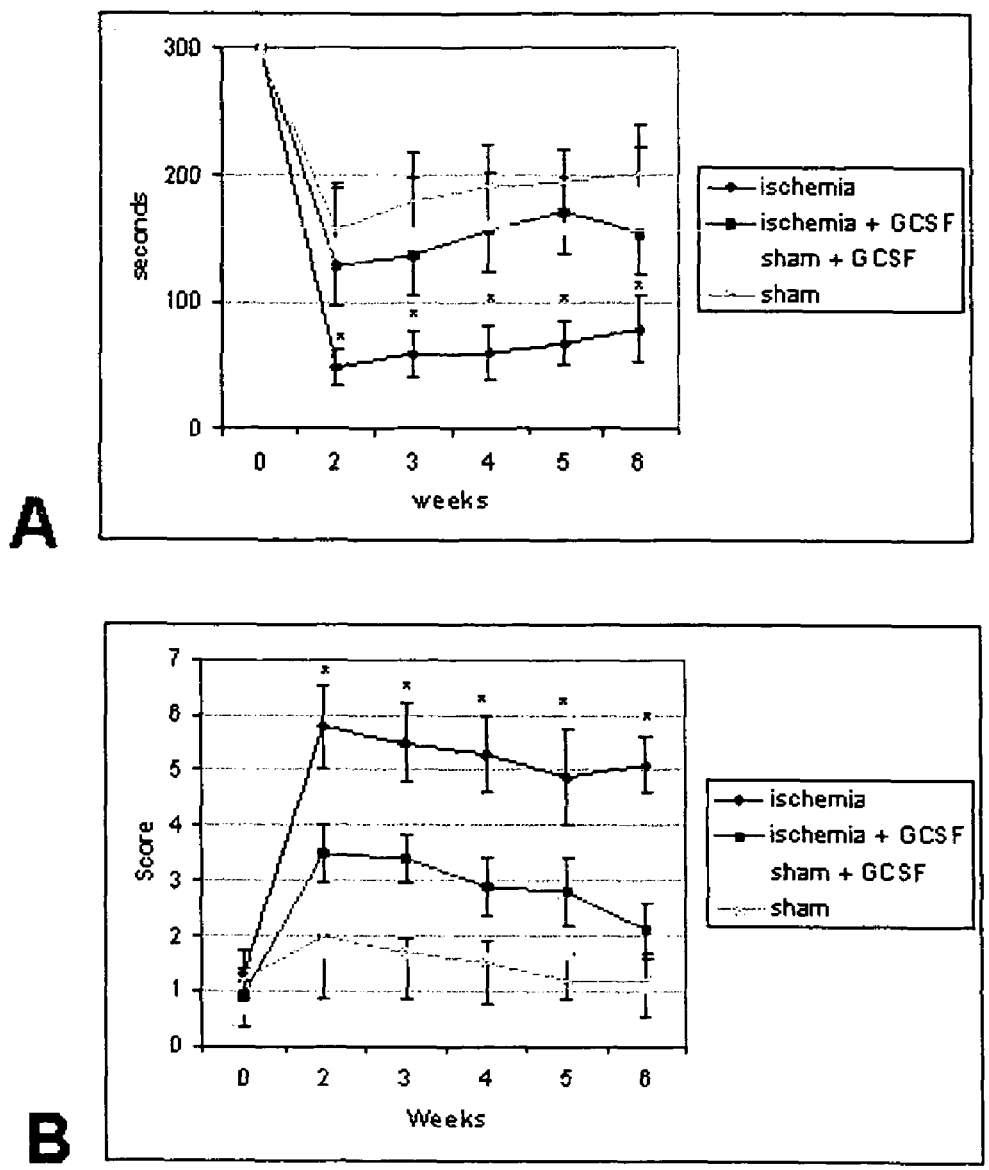
Figure 8, part I

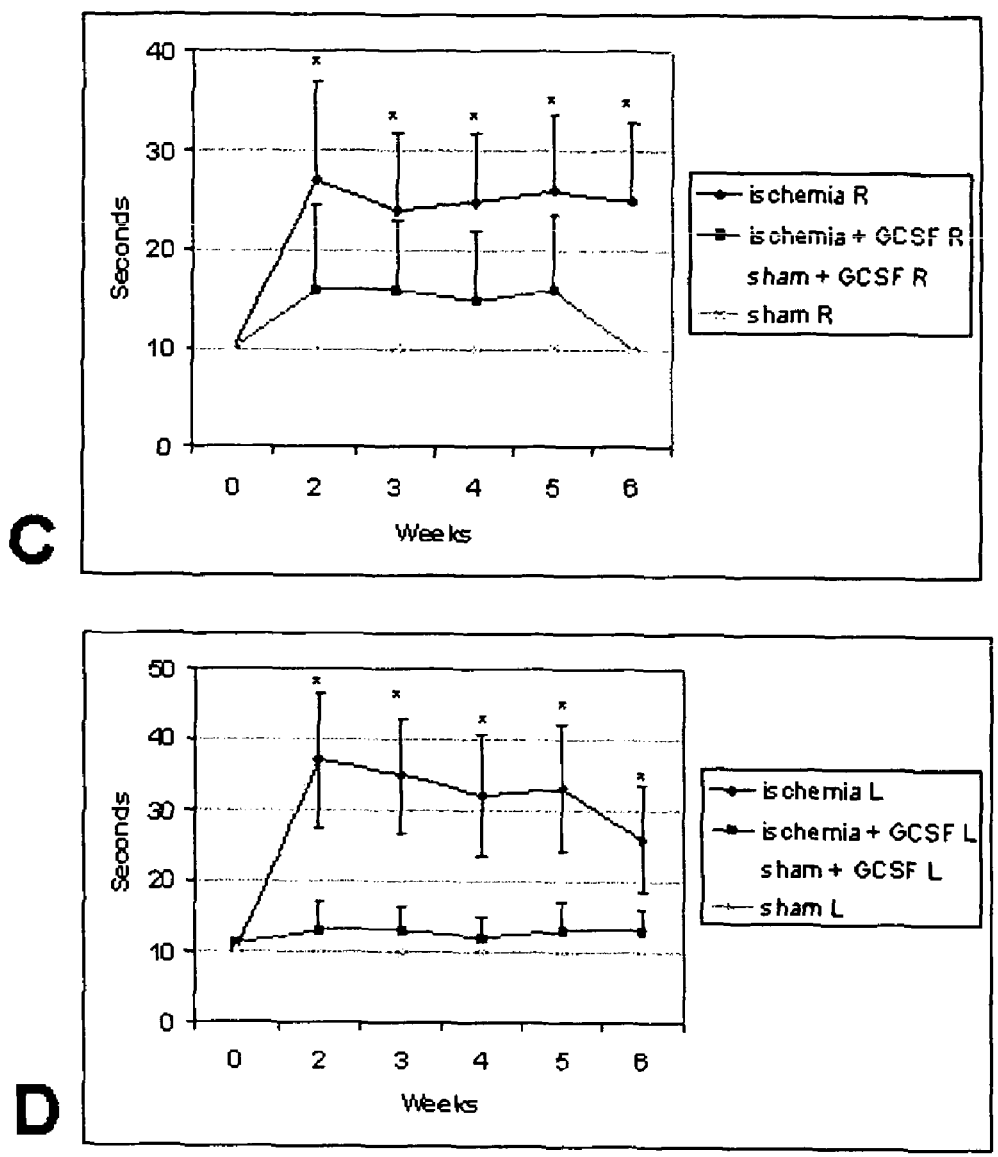
Figure 8, part II

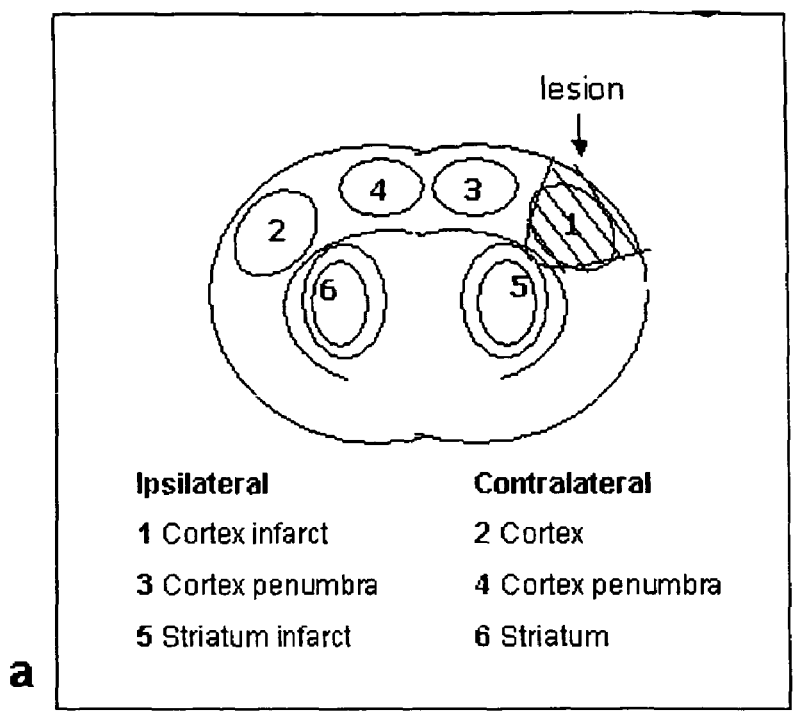
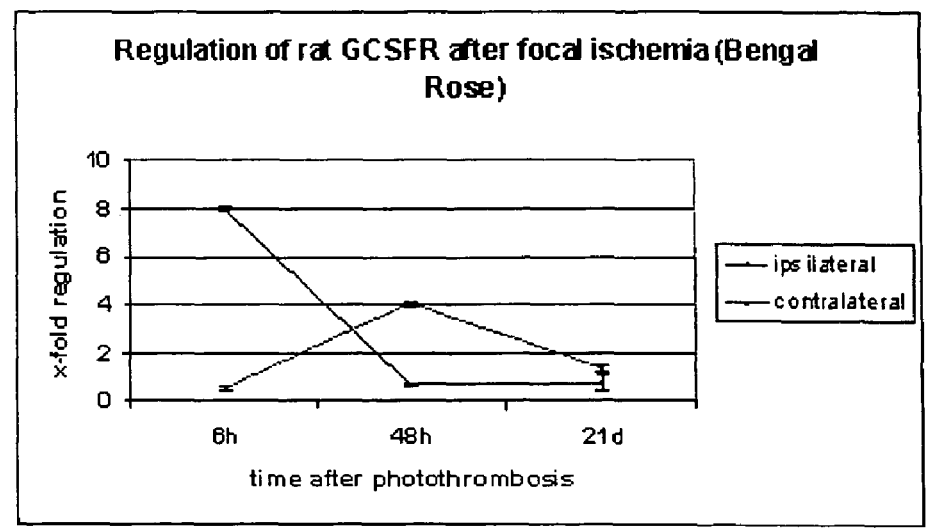
Figure 9

```
  1   M A G P A T Q S P M K L M A L Q L L L W H S A L W T V Q E A   hum G-CSF
  1   M A Q L S A Q R R M K L M A L Q L L L W Q S A L W S G R E A   mouse G-CS
  1   - - - - - - - - M M K L M A L Q L L L W H S A L W S G Q E A   rat G-CSF
  1   - - - - - - - - - K L M A L Q L L L W H S A L W M V Q E A     feline G-C
  1   - - - - - - - - - M X L M V L Q L L L W H S A L W T V H E A   bovine G-C
  1   - - - - - - - - - M K L M A L Q L L L W H I A L W M V P E A   pig G-CSF 31   T P L G P A S S L P - - - - - - Q S F L K C L E Q V R K I     hum G-CSF
 31   V P L V T V S A L P P S L P L P R S F L K S L E Q V R K I     mouse G-CS
 22   I P L L T V S S L P P S L P L P R S F L K S L E Q V R K I     rat G-CSF
 21   T P L G P T S S L P - - - - - - Q S F L K C L E Q V R K V     feline G-C
 22   T P L G P A R S L P - - - - - - Q S F L L K C L E Q V R K I   bovine G-C
 22   A P L S P A S S L P - - - - - - Q S F L K C L E Q V R K I     pig G-CSF 55   Q G D G A A L Q E K L V S E C A T Y K L C H P E E L V L L G   hum G-CSF
 61   Q A S G S V L L E Q L - - - C A T Y K L C H P E E L V L L G   mouse G-CS
 52   Q A R N T E L L E Q L - - - C A T Y K L C H P E E L V L F G   rat G-CSF
 45   Q A D G T A L Q E R L - - - C A A H K L C H P E E L V L L G   feline G-C
 46   Q A D G A E L Q E R L - - - C A A H K L C H P E E L M L L R   bovine G-C
 46   Q A D G A E L Q E R L - - - C A T H K L C H P Q E L V L L G   pig G-CSF 85   H S L G I P W A P L S S C P S Q A L Q L A G C L S Q L H S G   hum G-CSF
 88   H S L G I P K A S L S G C S S Q A L Q Q T Q C L S Q L H S G   mouse G-CS
 79   H S L G I P K A S L S S C S S Q A L Q Q T K C L S Q L H S G   rat G-CSF
 72   H A L G I P Q A P L S S C S S Q A L Q L T G C L R Q L H S G   feline G-C
 73   H S L G I P Q A P L S S C S S Q S L Q L T S C L M Q L H G G   bovine G-C
 73   H S L G L P Q A S L S S C S S Q A L Q L T G C L M Q L H G G   pig G-CSF 115   L F L Y Q G L L Q A L E G I S P E L G P T L D T L Q L D V A   hum G-CSF
118   L C L Y Q G L L Q A L S G I S P A L A P T L D L L Q L D V A   mouse G-CS
109   L F L Y Q G L L Q A L A G I S S E L A P T L D M L H L D V D   rat G-CSF
102   L F L Y Q G L L Q A L A G I S P E L A P T L D M L Q L D I T   feline G-C
103   L F L Y Q G L L Q A L A G I S P E L A P T L D T L Q L D V T   bovine G-C
103   L V L Y Q G L L Q A L A G I S P E L A P A L D I L Q L D V T   pig G-CSF 145   D F A T T I W Q Q M E E L G M A P A L Q P T Q G A M P A F A   hum G-CSF
148   N F A T T I W Q Q M E N L G V A P T V Q P T Q S A M P A F T   mouse G-CS
139   N F A T T I W Q Q M E S L G V A P T V Q P T Q S T M P I F T   rat G-CSF
132   D F A I N I W Q Q M E D V G M A P A V P P T Q G T M P T F T   feline G-C
133   D F A T N I W L Q M E D L G A A P A V Q P T Q G A M P T F T   bovine G-C
133   D L A T N I W L Q M E D L R M A P A S L P T Q G T V P T F T   pig G-CSF 175   S A F Q R R A G G V L V A S H L Q S F L E V S Y R V L R H L   hum G-CSF
178   S A F Q R R A G G V L A I S Y L Q G F L E T A R L A L H H L   mouse G-CS
169   S A F Q R R A G G V L T S Y L Q S F L E T A H H A L H H L     rat G-CSF
162   S A F Q R R A G G T L V A S N L Q S F L E V A Y R A L R H F   feline G-C
163   S A F Q R R A G G V L V A S Q L H R F L E L A Y R G L R Y L   bovine G-C
163   S A F Q R R A G G V L V V S Q L Q S F L E L A Y R V L R Y L   pig G-CSF 205   A Q P                                                         hum G-CSF
208   A                                                             mouse G-CS
199   P R P A Q K H F P E S L F I S I                               rat G-CSF
192   T K P                                                         feline G-C
193   A T P                                                         bovine G-C
193   A T P                                                         pig G-CSF
```

Figure 10

MARLGNCSLTWAALIILLLPGSLEECGHISVSAPIVHLGDPITASCLI-KQNCSHLDPEPQ  hgcsrr
MVGLGACTLTGVTLIFLLLPRSLESCGHIEISPPVVRLGDPVLASCTISPNCSKLDQQAK  mgcsrr
------------------LEGCGQIRISPPIVHLGDPVLASCTISPNCSKLDRQPK  rgcsrr (frag)

ILWRLGAE-LQPGGRQQRLSDGTQESIITLPHLNHTQAFLSCCLNWGNSLQILDQVELRA  hgcsrr
ILWRLQDEPIQPGDRQHHLPDGTQESLITLPHLNYTQAFLFCLVPWEDSVQLLDQAELHA  mgcsrr
ILWRLQDEPNQPGDRQHHLPDGSQESIITLPHLNYTQAFLFCLVPWNNSFQVLDQAELRA  rgcsrr (frag)

GYPPAIPHNLSCLMNLTTSSLICQWEPGPETHLPTSFTLKSFKSRGNCQTQGDSILDCVP  hgcsrr
GYPPASPSNLSCLMHLTTNSLVCQWEPGPETHLPTSFILKSFRSRADCQYQGDTIPDCVA  mgcsrr
CCKSLQPP----------THLLQC  rgcsrr (frag)

KDCQSHCCIPRKHLLLYQNWGIWVQAENALGTSWSPQLCLDPWDVVKLEPPWLRTWDPSP  hgcsrr
KKRQNNCSIPRKNLLLYQYWAIWWQAENWLGSSESPKLCLDPWDVVKLEPPWLQALDIGP  mgcsrr
                                                              rgcsrr (frag)

EAAPPQAGCLQLCWEPWQPGLHINQKCELRHKPQRGEASWALVGPLPLEALQYELCGLLP  hgcsrr
DVVSHQPGCLWLSWWKPWWKPSEYMEQECELRYQPQLKGANWTLVFHLPSSKDQFELCGLHQ  mgcsrr
                                                              rgcsrr (frag)

ATAYTLQIRCIRWPLPGHWSDWSPSLELRTTERAPTVRLDTWWRQRQLDP--RTVQLFWK  hgcsrr
APVYTLQWRCIRSSLPGFWSPWSPGLQLRPTWKAPTIRLDTWCQKKQLDPGTVSVQLFWK  mgcsrr
                                                              rgcsrr (frag)

PVFLEEDSGRIQGYVVSWRPSGQAGAILPLCNTTELSCTFHLPSEAQEVALVAYNSAGTS  hgcsrr
PTPLQEDSGQIQGYLLSWWNSPDHQGQDIHLCNTTQLSCIFLLPSEAQNVTLVAYNKAGTS  mgcsrr
                                                              rgcsrr (frag)

RPTPVVFSESRGPALTRLHAWARDPHSLWVGWEPPNPWPQGYVIEWGLGPPSASNSNKTWV  hgcsrr
SPTTVVFLENEGPAVTGLHAWAQDLNTIWVDWEAPSLLPQGYLIEWEWSSPSYNNSYKSWV  mgcsrr
                                                              rgcsrr (frag)

RWEQNGRATGFLLKENIRPFQLYEIIVTPLYQDTWGPSQHVYAYSQEWAPSHAPELHLKH  hgcsrr
WIEPNGNITGILLKDNINPFQLYRITVAPLYPGIVGPPVNVYTFAGERAPPHAPALHLKH  mgcsrr
                                                              rgcsrr (frag)

IGKTWAQLEWWPEPPELGKSPLTHYTIFWTNAQNQSFSAILNASSRGFVLHGLEPASLYH  hgcsrr
VGTTWAQLEWWPEAPRLGWIPLTHYTIFWADAGDHSFSVTLNISLHDFVLKHLEPASLYH  mgcsrr
                                                              rgcsrr (frag)

IHLWAASQAGATNSTVLTLWTLTPEGSELHIILGLFGLLLLLTCLCGTAWWLCCSPNRKNP  hgcsrr
VYLWATSRAGSTNSTGLTLRTLDP--SDLNIFLGIL-CLVLLSTTCVVTWWLCCKRRGKTS  mgcsrr
                                                              rgcsrr (frag)

LWPSVPDPAHSSLGSWWPTIWEEDAFQLPGLG---TPPITKLTVLEEDEKKPVPWESHNS  hgcsrr
FWGDVPDPAHSSLSSWLPTIWTEETFQLPSFWDSSVPSITKITELEED-KKPTHWWDSE-S  mgcsrr
                                                              rgcsrr (frag)

SETCGLPTLVQTYVLQGDPRAVSTQPQSQSGTSDQVLYGQLLGSPTSPGPGHYLRCDSTQ  hgcsrr
SGNGSLPALVQAYVLQGDPREISNQSQPPSRTGDQVLYGQVLESPTSPGVWQYIRSDSTQ  mgcsrr
                                                              rgcsrr (frag)

PLLAGLTPSPKSYENLWFQASPLGTLVTPAPSQEDDCVFGPLLNFPLLQGIRVHGWEALG  hgcsrr
PLLGCPTPSPKSYENIWFHSRPQETFVPQPPNQEDDCVFGPPFDFPLFQGLQVHGVEEQG  mgcsrr
                                                              rgcsrr (frag)

SF  hgcsrr
GF  mgcsrr
    rgcsrr (frag)

Figure 11

Biotinylated G-CSF detected on blot
via Streptavidin-HRP
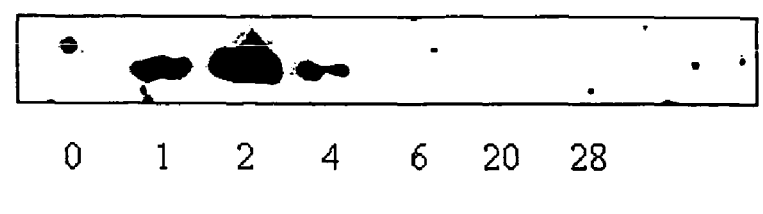
0   1   2   4   6   20   28
A                  hours after injection
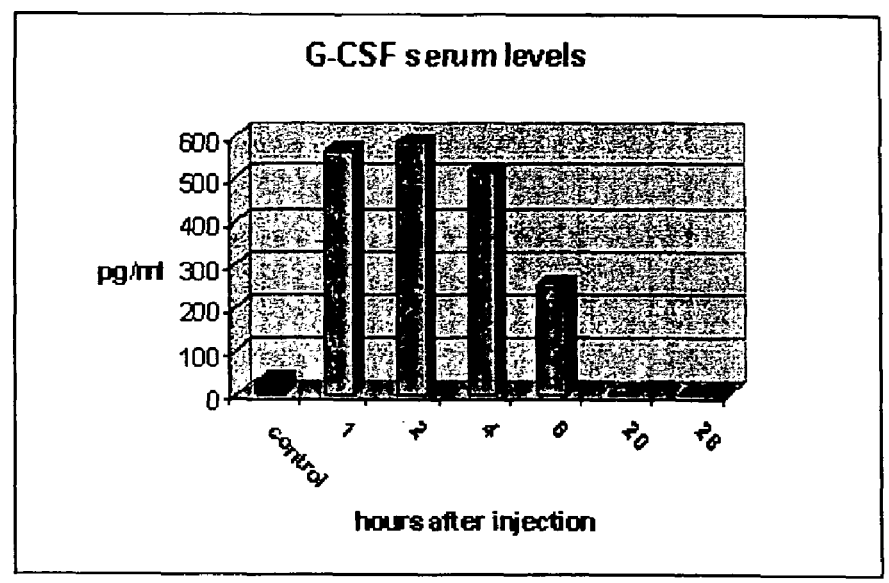
B
Figure 14

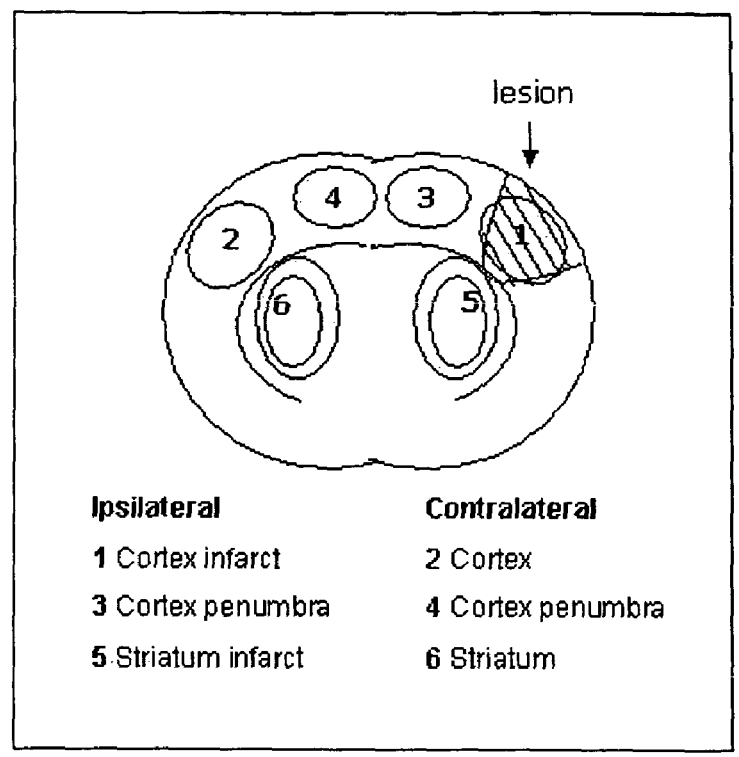
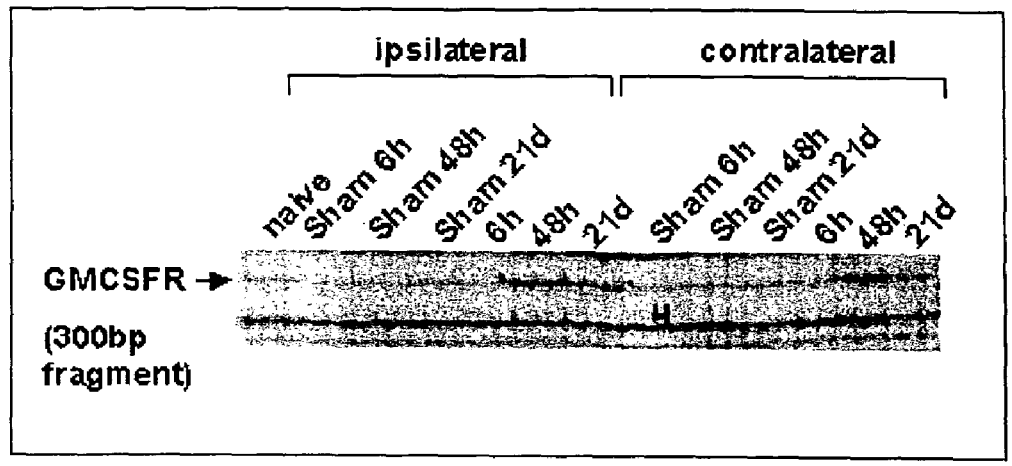
Figure 15

Figure 17

```
                    10                  20                  30                  40
- - - - - - - - - - - - - - - - A P T R S P N P V T R P W K H V D A I K E A L    rat gnc:
M W L Q N L L F L G I V V Y S L S A P T R S P I T V T R P W K H V E A I K E A L    mouse gn
M W L Q S L L L L G T V A C S I S A P A R S P S P S T Q P W E H V N A I Q E A R    hum gnc:

50                  60                  70                  80
S L L N D M R A L E N E K N E D V D I I S N E F S I Q R P T C V Q T R L K L Y K    rat gnc:
N L L D D M P V T L N - - - E E V E V V S N E F S F K K L T C V Q T R L K I F E    mouse gn
R L L N L S R D T A A E N N E T V E V I S E M F D L Q E P T C L Q T R L E L Y K    hum gnc:

90                  100                 110                 120
Q G L R G N L T K L N G A L T M I A S H Y Q T N C P P T P E T D C E I E V T T F    rat gnc:
Q G L R G N F T K L K G A L N M T A S Y Y Q T Y C P P T P E T D C E T Q V T T Y    mouse gn
Q G L R G S L T K L K G P L T M M A S H Y K Q H C P P T P E T S C A T Q I I T F    hum gnc:

130                 140
E D F I K N L K G F L F D I P F D C W K P V Q K                                    rat gnc:
A D F I D S L K T F L T D I P T E C K K P G Q K                                    mouse gn
E S F K E N L K D F L L V I P F D C W E P V Q E                                    hum gnc:
```

Figure 18

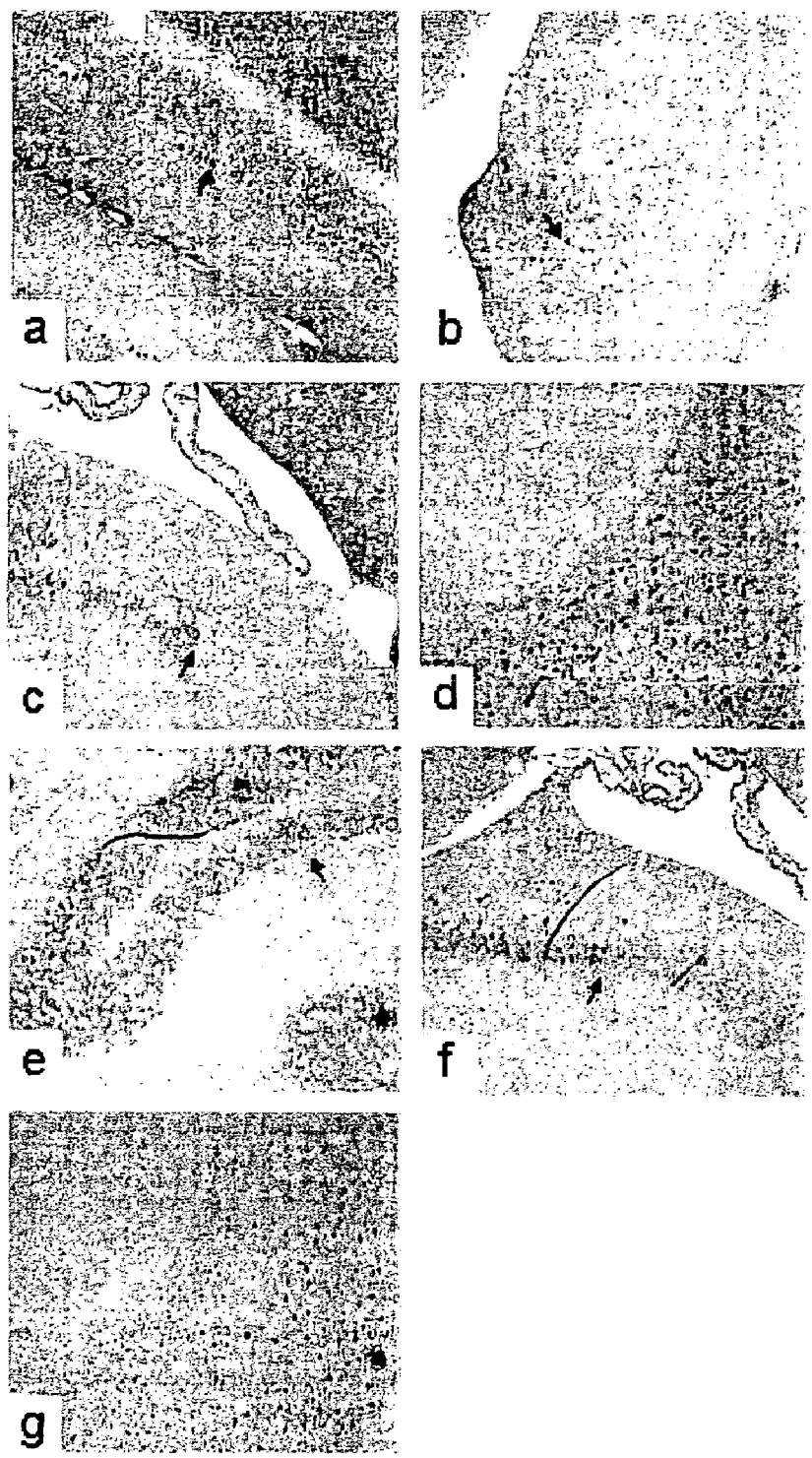
Figure 19, part I

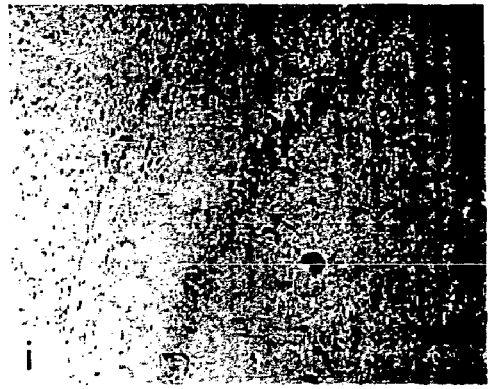
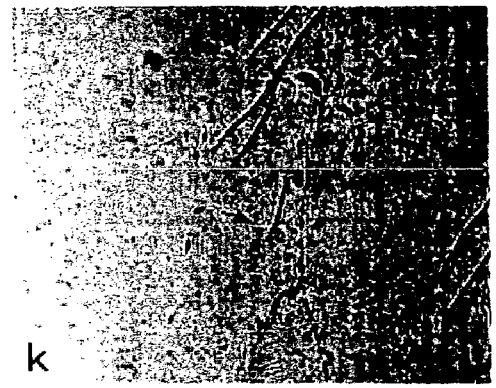
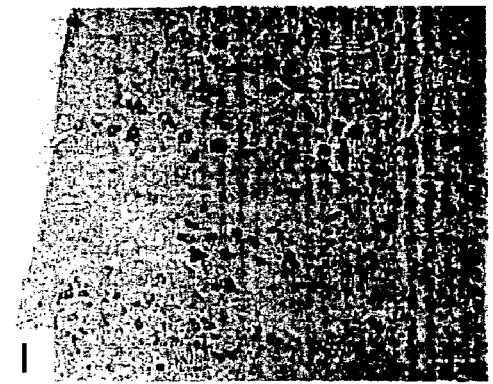
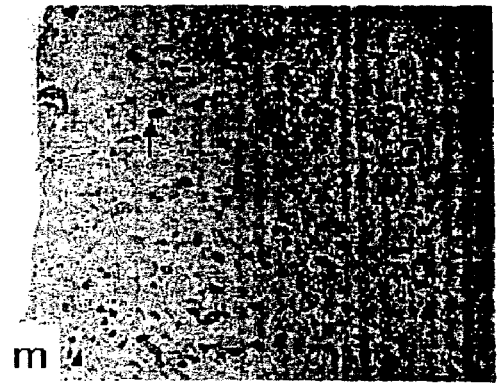
Figure 19, part II

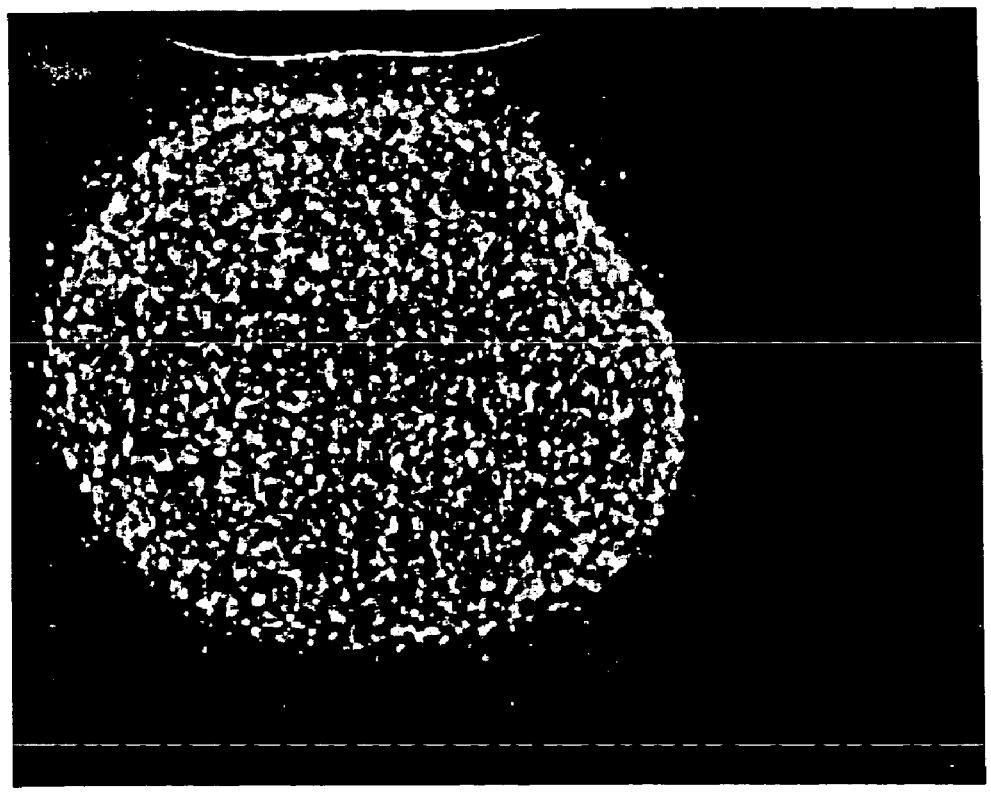
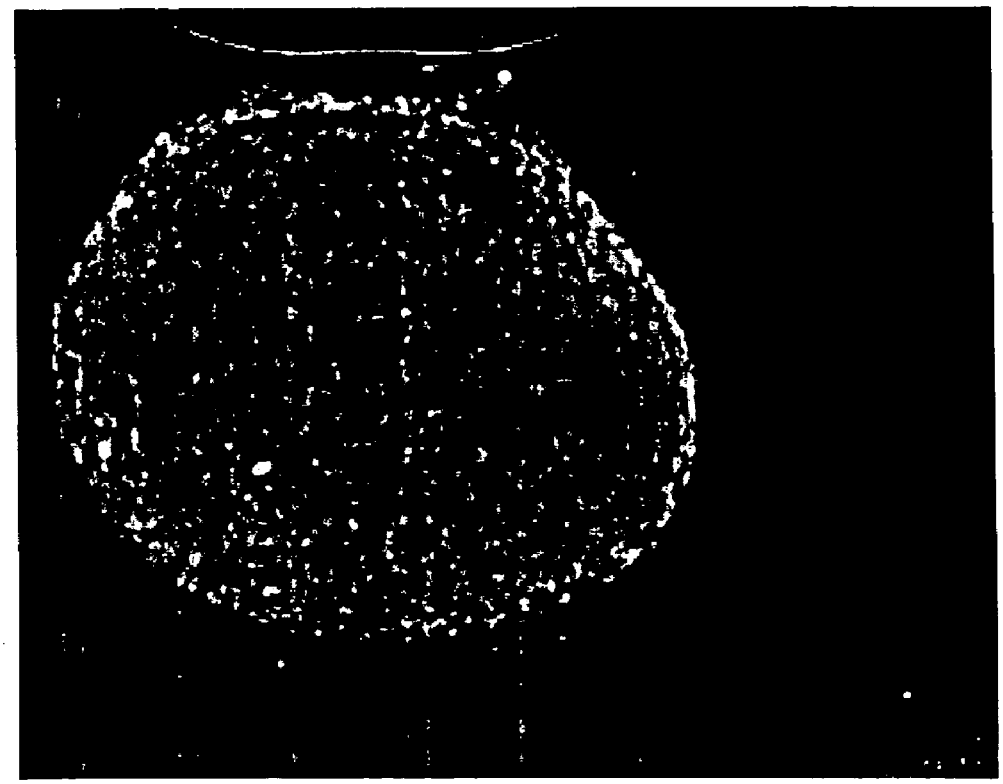
Figure 22

SEQUENCE LISTING

<160> NUMBER OF SEQ ID NOS: 41

<210> SEQ ID NO 1
<211> LENGTH: 70
<212> TYPE: PRT
<213> ORGANISM: Artificial Sequence
<220> FEATURE:
<223> OTHER INFORMATION: computer generated consensus sequence
<220> FEATURE:
<221> NAME/KEY: misc_feature
<222> LOCATION: (2)..(5)
<223> OTHER INFORMATION: Xaa is any amino acid
<220> FEATURE:
<221> NAME/KEY: misc_feature
<222> LOCATION: (6)..(41)
<223> OTHER INFORMATION: Xaa is any amino acid
<220> FEATURE:
<221> NAME/KEY: misc_feature
<222> LOCATION: (33)..(41)
<223> OTHER INFORMATION: may be present or absent
<220> FEATURE:
<221> NAME/KEY: misc_feature
<222> LOCATION: (47)..(49)
<223> OTHER INFORMATION: Xaa is any amino acid
<220> FEATURE:
<221> NAME/KEY: misc_feature
<222> LOCATION: (47)..(49)
<223> OTHER INFORMATION: amino acids may be present or absent
<220> FEATURE:
<221> NAME/KEY: misc_feature
<222> LOCATION: (46)..(46)
<223> OTHER INFORMATION: Xaa may be any amino acid
<220> FEATURE:
<221> NAME/KEY: misc_feature
<222> LOCATION: (50)..(60)
<223> OTHER INFORMATION: Xaa is any amino acid
<220> FEATURE:
<221> NAME/KEY: misc_feature
<222> LOCATION: (57)..(60)
<223> OTHER INFORMATION: may be present or absent
<220> FEATURE:
<221> NAME/KEY: misc_feature
<222> LOCATION: (63)..(64)
<223> OTHER INFORMATION: Xaa is any amino acid
<220> FEATURE:
<221> NAME/KEY: misc_feature
<222> LOCATION: (64)..(64)
<223> OTHER INFORMATION: may be present or absent
<220> FEATURE:
<221> NAME/KEY: misc_feature
<222> LOCATION: (69)..(69)
<223> OTHER INFORMATION: Xaa is any amino acid

<400> SEQUENCE: 1

Asn Xaa Xaa Xaa Xaa Ser Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Leu Val Ile Met Xaa Trp Xaa
            35                  40                  45

Xaa Xaa Pro Xaa Xaa Xaa Xaa Xaa Xaa Xaa Xaa Tyr Phe Xaa Xaa
        50                  55                  60

Val Ile Leu Met Xaa Trp
65                  70

<210> SEQ ID NO 2
<211> LENGTH: 21
<212> TYPE: DNA
<213> ORGANISM: Artificial Sequence
<220> FEATURE:

<223> OTHER INFORMATION: synthetic DNA

<400> SEQUENCE: 2
gcgggcaaat caggatctca c                                     21

<210> SEQ ID NO 3
<211> LENGTH: 21
<212> TYPE: DNA
<213> ORGANISM: Artificial Sequence
<220> FEATURE:
<223> OTHER INFORMATION: synthetic DNA

<400> SEQUENCE: 3
cgaagctcag cttgatccag g                                     21

<210> SEQ ID NO 4
<211> LENGTH: 280
<212> TYPE: DNA
<213> ORGANISM: Rattus rattus

<400> SEQUENCE: 4
gcgggcaaat caggatctca cccccccattg tccatcttgg ggatcctgtc ctggcctcct    60
gcaccatcag cccaaactgc agcaaactgg accgacagcc aaagatccta tggagactgc   120
aagatgaacc aaaccagcct ggggacagac agcatcacct gcctgacggg tcccaggagt   180
ccatcatcac tctgcctcat ctgaactaca ctcaggcctt cctcttctgc ttggtgccat   240
ggaacaacag cttccaggtc ctggatcaag ctgagcttcg                         280

<210> SEQ ID NO 5
<211> LENGTH: 22
<212> TYPE: DNA
<213> ORGANISM: Artificial Sequence
<220> FEATURE:
<223> OTHER INFORMATION: synthetic DNA

<400> SEQUENCE: 5
cccctcaaac ctatcctgcc tc                                    22

<210> SEQ ID NO 6
<211> LENGTH: 22
<212> TYPE: DNA
<213> ORGANISM: Artificial Sequence
<220> FEATURE:
<223> OTHER INFORMATION: synthetic DNA

<400> SEQUENCE: 6
tccaggcaga gatcagcgaa tg                                    22

<210> SEQ ID NO 7
<211> LENGTH: 21
<212> TYPE: DNA
<213> ORGANISM: Artificial Sequence
<220> FEATURE:
<223> OTHER INFORMATION: synthetic DNA

<400> SEQUENCE: 7
ccattgtcca tcttggggat c                                     21

<210> SEQ ID NO 8
<211> LENGTH: 21
<212> TYPE: DNA
<213> ORGANISM: Artificial Sequence
<220> FEATURE:
<223> OTHER INFORMATION: synthetic DNA -continued

<400> SEQUENCE: 8
cctggaagct gttgttccat g                                              21

<210> SEQ ID NO 9
<211> LENGTH: 20
<212> TYPE: DNA
<213> ORGANISM: Artificial Sequence
<220> FEATURE:
<223> OTHER INFORMATION: synthetic DNA

<400> SEQUENCE: 9
accccaccgt gttcttcgac                                                20

<210> SEQ ID NO 10
<211> LENGTH: 20
<212> TYPE: DNA
<213> ORGANISM: Artificial Sequence
<220> FEATURE:
<223> OTHER INFORMATION: synthetic DNA

<400> SEQUENCE: 10
catttgccat ggacaagatg                                                20

<210> SEQ ID NO 11
<211> LENGTH: 7
<212> TYPE: PRT
<213> ORGANISM: Artificial Sequence
<220> FEATURE:
<223> OTHER INFORMATION: synthetic peptide sequence

<400> SEQUENCE: 11

Leu Gly His Ser Leu Gly Ile
1               5

<210> SEQ ID NO 12
<211> LENGTH: 39
<212> TYPE: DNA
<213> ORGANISM: Artificial Sequence
<220> FEATURE:
<223> OTHER INFORMATION: synthetic DNA

<400> SEQUENCE: 12
cgggatccgg gaccgcgtat ctgatgacga gcgtgtcaa                            39

<210> SEQ ID NO 13
<211> LENGTH: 25
<212> TYPE: DNA
<213> ORGANISM: Artificial Sequence
<220> FEATURE:
<223> OTHER INFORMATION: synthetic DNA

<400> SEQUENCE: 13
ctcggagacg ctgaggaagg acctg                                          25

<210> SEQ ID NO 14
<211> LENGTH: 40
<212> TYPE: DNA
<213> ORGANISM: Artificial Sequence
<220> FEATURE:
<223> OTHER INFORMATION: synthetic DNA

<400> SEQUENCE: 14
ctgcggccct agaccacgcc caccgctccc cgtgacgtcg                           40

<210> SEQ ID NO 15
<211> LENGTH: 22
<212> TYPE: DNA
<213> ORGANISM: Artificial Sequence
<220> FEATURE:
<223> OTHER INFORMATION: synthetic DNA

<400> SEQUENCE: 15
acgtcgttgg ctcagttatg tc                                              22

<210> SEQ ID NO 16
<211> LENGTH: 24
<212> TYPE: DNA
<213> ORGANISM: Artificial Sequence
<220> FEATURE:
<223> OTHER INFORMATION: synthetic DNA

<400> SEQUENCE: 16
atttatgtca gagatggagg atgg                                            24

<210> SEQ ID NO 17
<211> LENGTH: 20
<212> TYPE: DNA
<213> ORGANISM: Artificial Sequence
<220> FEATURE:
<223> OTHER INFORMATION: synthetic DNA

<400> SEQUENCE: 17
accccaccgt gttcttcgac                                                 20

<210> SEQ ID NO 18
<211> LENGTH: 20
<212> TYPE: DNA
<213> ORGANISM: Artificial Sequence
<220> FEATURE:
<223> OTHER INFORMATION: synthetic DNA

<400> SEQUENCE: 18
catttgccat ggacaagatg                                                 20

<210> SEQ ID NO 19
<211> LENGTH: 22
<212> TYPE: DNA
<213> ORGANISM: Artificial Sequence
<220> FEATURE:
<223> OTHER INFORMATION: synthetic DNA

<400> SEQUENCE: 19
acgtcgttgg ctcagttatg tc                                              22

<210> SEQ ID NO 20
<211> LENGTH: 24
<212> TYPE: DNA
<213> ORGANISM: Artificial Sequence
<220> FEATURE:
<223> OTHER INFORMATION: synthetic DNA

<400> SEQUENCE: 20
atttatgtca gagatggagg atgg                                            24

<210> SEQ ID NO 21
<211> LENGTH: 177
<212> TYPE: DNA
<213> ORGANISM: Rattus rattus

<400> SEQUENCE: 21

```
acgtcgttgg ctcagttatg tcagacagga aatctcacca tcccacaatg attgacagct    60
ctcacaggga atcccgcctc cgctgggacc aattgacatc acggacagga atacccgccc   120
ctgtggccct gatgggcagg tcctgcctgg ctcccatcct ccatctctga cataaat      177
```

<210> SEQ ID NO 22
<211> LENGTH: 400
<212> TYPE: PRT
<213> ORGANISM: Homo sapiens

<400> SEQUENCE: 22

```
Met Leu Leu Val Thr Ser Leu Leu Cys Glu Leu Pro His Pro
1               5                   10                  15

Ala Phe Leu Leu Ile Pro Glu Lys Ser Asp Leu Arg Thr Val Ala Pro
            20                  25                  30

Ala Ser Ser Leu Asn Val Arg Phe Asp Ser Arg Thr Met Asn Leu Ser
        35                  40                  45

Trp Asp Cys Gln Glu Asn Thr Thr Phe Ser Lys Cys Phe Leu Thr Asp
    50                  55                  60

Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
            100                 105                 110

Asn Ser Gly Arg Glu Gly Thr Ala Ala Gln Asn Phe Ser Cys Phe Ile
        115                 120                 125

Tyr Asn Ala Asp Leu Met Asn Cys Thr Trp Ala Arg Gly Pro Thr Ala
    130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
        195                 200                 205

Leu Leu Asp Thr Lys Lys Ile Glu Arg Phe Asn Pro Pro Ser Asn Val
    210                 215                 220

Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
                245                 250                 255

Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
        275                 280                 285

Arg Ala Lys His Ser Val Lys Ile Arg Ala Ala Asp Val Arg Ile Leu
    290                 295                 300

Asn Trp Ser Ser Trp Ser Glu Ala Ile Glu Phe Gly Ser Asp Asp Gly
305                 310                 315                 320

Asn Leu Gly Ser Val Tyr Ile Tyr Val Leu Leu Ile Val Gly Thr Leu
                325                 330                 335

Val Cys Gly Ile Val Leu Gly Phe Leu Phe Lys Arg Phe Leu Arg Ile
            340                 345                 350
```

```
Gln Arg Leu Phe Pro Pro Val Pro Gln Ile Lys Asp Lys Leu Asn Asp
            355                 360                 365

Asn His Glu Val Glu Asp Glu Ile Ile Trp Glu Glu Phe Thr Pro Glu
            370                 375                 380

Glu Gly Lys Gly Tyr Arg Glu Val Leu Ile Val Lys Glu Ile Thr
385                 390                 395                 400

<210> SEQ ID NO 23
<211> LENGTH: 388
<212> TYPE: PRT
<213> ORGANISM: Mus musculus

<400> SEQUENCE: 23

Met Thr Ser Ser His Ala Met Asn Ile Thr Pro Leu Ala Gln Leu Ala
1               5                   10                  15

Leu Leu Phe Ser Thr Leu Leu Pro Gly Thr Gln Ala Leu Leu Ala
            20                  25                  30

Pro Thr Thr Pro Asp Ala Gly Ser Ala Leu Asn Leu Thr Phe Asp Pro
            35                  40                  45

Trp Thr Arg Thr Leu Thr Trp Ala Cys Asp Thr Ala Ala Gly Asn Val
50                  55                  60

Thr Val Thr Ser Cys Thr Val Thr Ser Arg Glu Ala Gly Ile His Arg
65                  70                  75                  80

Arg Val Ser Pro Phe Gly Cys Arg Cys Trp Phe Arg Arg Met Met Ala
            85                  90                  95

Leu His His Gly Val Thr Leu Asp Val Asn Gly Thr Val Gly Gly Ala
            100                 105                 110

Ala Ala His Trp Arg Leu Ser Phe Val Asn Glu Ser Ala Ala Gly Ser
            115                 120                 125

Gly Ala Glu Asn Leu Thr Cys Glu Ile Arg Ala Ala Arg Phe Leu Ser
            130                 135                 140

Cys Ala Trp Arg Glu Gly Pro Ala Ala Pro Ala Asp Val Arg Tyr Ser
145                 150                 155                 160

Leu Arg Val Leu Asn Ser Thr Gly His Asp Val Ala Arg Cys Met Ala
            165                 170                 175

Asp Pro Gly Asp Asp Val Ile Thr Gln Cys Ile Ala Asn Asp Leu Ser
            180                 185                 190

Leu Leu Gly Ser Glu Ala Tyr Leu Val Val Thr Gly Arg Ser Gly Ala
            195                 200                 205

Gly Pro Val Arg Phe Leu Asp Asp Val Val Ala Thr Lys Ala Leu Glu
            210                 215                 220

Arg Leu Gly Pro Pro Arg Asp Val Thr Ala Ser Cys Asn Ser Ser His
225                 230                 235                 240

Cys Thr Val Ser Trp Ala Pro Pro Ser Thr Trp Ala Ser Leu Thr Ala
            245                 250                 255

Arg Asp Phe Gln Phe Glu Val Gln Trp Gln Ser Ala Glu Pro Gly Ser
            260                 265                 270

Thr Pro Arg Lys Val Leu Val Glu Glu Thr Arg Leu Ala Phe Pro
            275                 280                 285

Ser Pro Ala Pro His Gly Gly His Lys Val Lys Val Arg Ala Gly Asp
            290                 295                 300

Thr Arg Met Lys His Trp Gly Glu Trp Ser Pro Ala His Pro Leu Glu
305                 310                 315                 320

Ala Glu Asp Thr Arg Val Pro Gly Ala Leu Leu Tyr Ala Val Thr Ala
```

```
                325                 330                 335
Cys Ala Val Leu Leu Cys Ala Leu Ala Leu Gly Val Thr Cys Arg Arg
            340                 345                 350

Phe Glu Val Thr Arg Arg Leu Phe Pro Pro Ile Pro Gly Ile Arg Asp
        355                 360                 365

Lys Val Ser Asp Asp Val Arg Val Asn Pro Glu Thr Leu Arg Lys Asp
    370                 375                 380

Leu Leu Gln Pro
385

<210> SEQ ID NO 24
<211> LENGTH: 9
<212> TYPE: PRT
<213> ORGANISM: Rattus rattus

<400> SEQUENCE: 24

Ile Asn Ser Glu Arg Thr Ser Glu Gln
1               5

<210> SEQ ID NO 25
<211> LENGTH: 127
<212> TYPE: PRT
<213> ORGANISM: Rattus rattus

<400> SEQUENCE: 25

Ala Pro Thr Arg Ser Pro Asn Pro Val Thr Arg Pro Trp Lys His Val
1               5                   10                  15

Asp Ala Ile Lys Glu Ala Leu Ser Leu Leu Asn Asp Met Arg Ala Leu
            20                  25                  30

Glu Asn Glu Lys Asn Glu Asp Val Asp Ile Ile Ser Asn Glu Phe Ser
        35                  40                  45

Ile Gln Arg Pro Thr Cys Val Gln Thr Arg Leu Lys Leu Tyr Lys Gln
    50                  55                  60

Gly Leu Arg Gly Asn Leu Thr Lys Leu Asn Gly Ala Leu Thr Met Ile
65                  70                  75                  80

Ala Ser His Tyr Gln Thr Asn Cys Pro Pro Thr Pro Glu Thr Asp Cys
                85                  90                  95

Glu Ile Asp Val Thr Thr Phe Glu Asp Phe Ile Lys Asn Leu Lys Gly
            100                 105                 110

Phe Leu Phe Asp Ile Pro Phe Asp Cys Trp Lys Pro Val Gln Lys
        115                 120                 125

<210> SEQ ID NO 26
<211> LENGTH: 141
<212> TYPE: PRT
<213> ORGANISM: Mus musculus

<400> SEQUENCE: 26

Met Trp Leu Gln Asn Leu Arg Leu Lys Ile Phe Glu Gln Gly Leu Arg
1               5                   10                  15

Gly Asn Phe Thr Lys Leu Lys Gly Ala Leu Asn Met Thr Ala Ser Tyr
            20                  25                  30

Tyr Gln Thr Tyr Cys Pro Pro Thr Pro Glu Thr Asp Cys Glu Thr Gln
        35                  40                  45

Val Thr Thr Tyr Ala Asp Phe Ile Asp Ser Leu Lys Thr Leu Phe Leu
    50                  55                  60

Gly Ile Val Val Tyr Ser Leu Ser Ala Pro Thr Arg Ser Pro Ile Phe
65                  70                  75                  80
```

Leu Thr Asp Ile Pro Phe Glu Cys Lys Lys Pro Gly Gln Lys Thr Val
                85                  90                  95

Thr Arg Pro Trp Lys His Val Glu Ala Ile Lys Glu Ala Leu Asn Leu
            100                 105                 110

Leu Asp Asp Met Pro Val Thr Leu Asn Glu Glu Val Glu Val Val Ser
        115                 120                 125

Asn Glu Phe Ser Phe Lys Lys Leu Thr Cys Val Gln Thr
    130                 135                 140

<210> SEQ ID NO 27
<211> LENGTH: 144
<212> TYPE: PRT
<213> ORGANISM: Homo sapiens

<400> SEQUENCE: 27

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 28
<211> LENGTH: 207
<212> TYPE: PRT
<213> ORGANISM: Homo sapiens

<400> SEQUENCE: 28

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

```
Ser Pro Glu Leu Gly Pro Thr Leu Asp Thr Leu Gln Leu Asp Val Ala
        130                 135                 140

Asp Phe Ala Thr Thr Ile Trp Gln Gln Met Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 29
<211> LENGTH: 208
<212> TYPE: PRT
<213> ORGANISM: Mus musculus

<400> SEQUENCE: 29

Met Ala Gln Leu Ser Ala Gln Arg Arg Met Lys Leu Met Ala Leu Gln
1               5                   10                  15

Leu Leu Leu Trp Gln Ser Ala Leu Trp Ser Gly Arg Glu Ala Val Pro
            20                  25                  30

Leu Val Thr Val Ser Ala Leu Pro Pro Ser Leu Pro Leu Pro Arg Ser
        35                  40                  45

Phe Leu Leu Lys Ser Leu Glu Gln Val Arg Lys Ile Gln Ala Ser Gly
    50                  55                  60

Ser Val Leu Leu Glu Gln Leu Cys Ala Thr Tyr Lys Leu Cys His Pro
65                  70                  75                  80

Glu Glu Leu Val Leu Leu Gly His Ser Leu Gly Ile Pro Lys Ala Ser
                85                  90                  95

Leu Ser Gly Cys Ser Ser Gln Ala Leu Gln Gln Thr Gln Cys Leu Ser
            100                 105                 110

Gln Leu His Ser Gly Leu Cys Leu Tyr Gln Gly Leu Leu Gln Ala Leu
        115                 120                 125

Ser Gly Ile Ser Pro Ala Leu Ala Pro Thr Leu Asp Leu Leu Gln Leu
    130                 135                 140

Asp Val Ala Asn Phe Ala Thr Thr Ile Trp Gln Gln Met Glu Asn Leu
145                 150                 155                 160

Gly Val Ala Pro Thr Val Gln Pro Thr Gln Ser Ala Met Pro Ala Phe
                165                 170                 175

Thr Ser Ala Phe Gln Arg Arg Ala Gly Gly Val Leu Ala Ile Ser Tyr
            180                 185                 190

Leu Gln Gly Phe Leu Glu Thr Ala Arg Leu Ala Leu His His Leu Ala
        195                 200                 205

<210> SEQ ID NO 30
<211> LENGTH: 214
<212> TYPE: PRT
<213> ORGANISM: Rattus norvegicus

<400> SEQUENCE: 30

Met Lys Leu Met Ala Leu Gln Leu Leu Leu Trp His Ser Ala Leu Trp
1               5                   10                  15

Ser Gly Gln Glu Ala Ile Pro Leu Leu Thr Val Ser Ser Leu Pro Pro
            20                  25                  30

Ser Leu Pro Leu Pro Arg Ser Phe Leu Leu Lys Ser Leu Glu Gln Val
        35                  40                  45
```

```
Arg Lys Ile Gln Ala Arg Asn Thr Glu Leu Leu Glu Gln Leu Cys Ala
 50                  55                  60
Thr Tyr Lys Leu Cys His Pro Glu Glu Leu Val Leu Phe Gly His Ser
 65                  70                  75                  80
Leu Gly Ile Pro Lys Ala Ser Leu Ser Ser Cys Ser Ser Gln Ala Leu
                 85                  90                  95
Gln Gln Thr Lys Cys Leu Ser Gln Leu His Ser Gly Leu Phe Leu Tyr
            100                 105                 110
Gln Gly Leu Leu Gln Ala Leu Ala Gly Ile Ser Ser Glu Leu Ala Pro
            115                 120                 125
Thr Leu Asp Met Leu His Leu Asp Val Asp Asn Phe Ala Thr Thr Ile
130                 135                 140
Trp Gln Gln Met Glu Ser Leu Gly Val Ala Pro Thr Val Gln Pro Thr
145                 150                 155                 160
Gln Ser Thr Met Pro Ile Phe Thr Ser Ala Phe Gln Arg Arg Ala Gly
                165                 170                 175
Gly Val Leu Val Thr Ser Tyr Leu Gln Ser Phe Leu Glu Thr Ala His
            180                 185                 190
His Ala Leu His His Leu Pro Arg Pro Ala Gln Lys His Phe Pro Glu
            195                 200                 205
Ser Leu Phe Ile Ser Ile
            210

<210> SEQ ID NO 31
<211> LENGTH: 195
<212> TYPE: PRT
<213> ORGANISM: Felis catus

<400> SEQUENCE: 31

Met Lys Leu Thr Ala Leu Gln Leu Leu Leu Trp His Ser Ala Leu Trp
 1               5                  10                  15
Met Val Gln Glu Ala Thr Pro Leu Gly Pro Thr Ser Ser Leu Pro Gln
             20                  25                  30
Ser Phe Leu Leu Lys Cys Leu Glu Gln Val Arg Lys Val Gln Ala Asp
            35                  40                  45
Gly Thr Ala Leu Gln Glu Arg Leu Cys Ala Ala His Lys Leu Cys His
 50                  55                  60
Pro Glu Glu Leu Val Leu Leu Gly His Ala Leu Gly Ile Pro Gln Ala
 65                  70                  75                  80
Pro Leu Ser Ser Cys Ser Ser Gln Ala Leu Gln Leu Thr Gly Cys Leu
                 85                  90                  95
Arg Gln Leu His Ser Gly Leu Phe Leu Tyr Gln Gly Leu Leu Gln Ala
            100                 105                 110
Leu Ala Gly Ile Ser Pro Glu Leu Ala Pro Thr Leu Asp Met Leu Gln
            115                 120                 125
Leu Asp Ile Thr Asp Phe Ala Ile Asn Ile Trp Gln Gln Met Glu Asp
130                 135                 140
Val Gly Met Ala Pro Ala Val Pro Pro Thr Gln Gly Thr Met Pro Thr
145                 150                 155                 160
Phe Thr Ser Ala Phe Gln Arg Arg Ala Gly Gly Thr Leu Val Ala Ser
                165                 170                 175
Asn Leu Gln Ser Phe Leu Glu Val Ala Tyr Arg Ala Leu Arg His Phe
            180                 185                 190
Thr Lys Pro
```

-continued

```
                195

<210> SEQ ID NO 32
<211> LENGTH: 195
<212> TYPE: PRT
<213> ORGANISM: Bos taurus

<400> SEQUENCE: 32

Met Lys Leu Met Val Leu Gln Leu Leu Leu Trp His Ser Ala Leu Trp
1               5                   10                  15

Thr Val His Glu Ala Thr Pro Leu Gly Pro Ala Arg Ser Leu Pro Gln
            20                  25                  30

Ser Phe Leu Leu Lys Cys Leu Glu Gln Val Arg Lys Ile Gln Ala Asp
        35                  40                  45

Gly Ala Glu Leu Gln Glu Arg Leu Cys Ala Ala His Lys Leu Cys His
    50                  55                  60

Pro Glu Glu Leu Met Leu Leu Arg His Ser Leu Gly Ile Pro Gln Ala
65                  70                  75                  80

Pro Leu Ser Ser Cys Ser Ser Gln Ser Leu Gln Leu Thr Ser Cys Leu
                85                  90                  95

Asn Gln Leu His Gly Gly Leu Phe Leu Tyr Gln Gly Leu Leu Gln Ala
            100                 105                 110

Leu Ala Gly Ile Ser Pro Glu Leu Ala Pro Thr Leu Asp Thr Leu Gln
        115                 120                 125

Leu Asp Val Thr Asp Phe Ala Thr Asn Ile Trp Leu Gln Met Glu Asp
    130                 135                 140

Leu Gly Ala Ala Pro Ala Val Gln Pro Thr Gln Gly Ala Met Pro Thr
145                 150                 155                 160

Phe Thr Ser Ala Phe Gln Arg Arg Ala Gly Gly Val Leu Val Ala Ser
                165                 170                 175

Gln Leu His Arg Phe Leu Glu Leu Ala Tyr Arg Gly Leu Arg Tyr Leu
            180                 185                 190

Ala Glu Pro
        195

<210> SEQ ID NO 33
<211> LENGTH: 195
<212> TYPE: PRT
<213> ORGANISM: Sus scrofa

<400> SEQUENCE: 33

Met Lys Leu Met Ala Leu Gln Leu Leu Leu Trp His Ile Ala Leu Trp
1               5                   10                  15

Met Val Pro Glu Ala Ala Pro Leu Ser Pro Ala Ser Ser Leu Pro Gln
            20                  25                  30

Ser Phe Leu Leu Lys Cys Leu Glu Gln Val Arg Lys Ile Gln Ala Asp
        35                  40                  45

Gly Ala Glu Leu Gln Glu Arg Leu Cys Ala Thr His Lys Leu Cys His
    50                  55                  60

Pro Gln Glu Leu Val Leu Leu Gly His Ser Leu Gly Leu Pro Gln Ala
65                  70                  75                  80

Ser Leu Ser Ser Cys Ser Ser Gln Ala Leu Gln Leu Thr Gly Cys Leu
                85                  90                  95

Asn Gln Leu His Gly Gly Leu Val Leu Tyr Gln Gly Leu Leu Gln Ala
            100                 105                 110

Leu Ala Gly Ile Ser Pro Glu Leu Ala Pro Ala Leu Asp Ile Leu Gln
```

-continued

```
                115                 120                 125
Leu Asp Val Thr Asp Leu Ala Thr Asn Ile Trp Leu Gln Met Glu Asp
            130                 135                 140

Leu Arg Met Ala Pro Ala Ser Leu Pro Thr Gln Gly Thr Val Pro Thr
145                 150                 155                 160

Phe Thr Ser Ala Phe Gln Arg Arg Ala Gly Gly Val Leu Val Val Ser
                165                 170                 175

Gln Leu Gln Ser Phe Leu Glu Leu Ala Tyr Arg Val Leu Arg Tyr Leu
            180                 185                 190

Ala Glu Pro
        195

<210> SEQ ID NO 34
<211> LENGTH: 836
<212> TYPE: PRT
<213> ORGANISM: Homo sapiens

<400> SEQUENCE: 34

Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
                20                  25                  30

Ala Pro Ile Val His Leu Gly Asp Pro Ile Thr Ala Ser Cys Ile Ile
            35                  40                  45

Lys Gln Asn Cys Ser His Leu Asp Pro Glu Pro Gln Ile Leu Trp Arg
    50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
            100                 105                 110

Asp Gln Val Glu Leu Arg Ala Gly Tyr Pro Pro Ala Ile Pro His Asn
        115                 120                 125

Leu Ser Cys Leu Met Asn Leu Thr Thr Ser Ser Leu Ile Cys Gln Trp
    130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
        195                 200                 205

Leu Gly Thr Ser Met Ser Pro Gln Leu Cys Leu Asp Pro Met Asp Val
    210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
        275                 280                 285
```

-continued

```
Ala Leu Gln Tyr Glu Leu Cys Gly Leu Leu Pro Ala Thr Ala Tyr Thr
    290                 295                 300
Leu Gln Ile Arg Cys Ile Arg Trp Pro Leu Pro Gly His Trp Ser Asp
305                 310                 315                 320
Trp Ser Pro Ser Leu Glu Leu Arg Thr Thr Glu Arg Ala Pro Thr Val
                325                 330                 335
Arg Leu Asp Thr Trp Trp Arg Gln Arg Gln Leu Asp Pro Arg Thr Val
            340                 345                 350
Gln Leu Phe Trp Lys Pro Val Pro Leu Glu Glu Asp Ser Gly Arg Ile
        355                 360                 365
Gln Gly Tyr Val Val Ser Trp Arg Pro Ser Gly Gln Ala Gly Ala Ile
    370                 375                 380
Leu Pro Leu Cys Asn Thr Thr Glu Leu Ser Cys Thr Phe His Leu Pro
385                 390                 395                 400
Ser Glu Ala Gln Glu Val Ala Leu Val Ala Tyr Asn Ser Ala Gly Thr
                405                 410                 415
Ser Arg Pro Thr Pro Val Val Phe Ser Glu Ser Arg Gly Pro Ala Leu
            420                 425                 430
Thr Arg Leu His Ala Met Ala Arg Asp Pro His Ser Leu Trp Val Gly
        435                 440                 445
Trp Glu Pro Pro Asn Pro Trp Pro Gln Gly Tyr Val Ile Glu Trp Gly
    450                 455                 460
Leu Gly Pro Pro Ser Ala Ser Asn Ser Asn Lys Thr Trp Arg Met Glu
465                 470                 475                 480
Gln Asn Gly Arg Ala Thr Gly Phe Leu Leu Lys Glu Asn Ile Arg Pro
                485                 490                 495
Phe Gln Leu Tyr Glu Ile Ile Val Thr Pro Leu Tyr Gln Asp Thr Met
            500                 505                 510
Gly Pro Ser Gln His Val Tyr Ala Tyr Ser Gln Glu Met Ala Pro Ser
        515                 520                 525
His Ala Pro Glu Leu His Leu Lys His Ile Gly Lys Thr Trp Ala Gln
    530                 535                 540
Leu Glu Trp Val Pro Glu Pro Pro Glu Leu Gly Lys Ser Pro Leu Thr
545                 550                 555                 560
His Tyr Thr Ile Phe Trp Thr Asn Ala Gln Asn Gln Ser Phe Ser Ala
                565                 570                 575
Ile Leu Asn Ala Ser Ser Arg Gly Phe Val Leu His Gly Leu Glu Pro
            580                 585                 590
Ala Ser Leu Tyr His Ile His Leu Met Ala Ala Ser Gln Ala Gly Ala
        595                 600                 605
Thr Asn Ser Thr Val Leu Thr Leu Met Thr Leu Thr Pro Glu Gly Ser
    610                 615                 620
Glu Leu His Ile Ile Leu Gly Leu Phe Gly Leu Leu Leu Leu Leu Thr
625                 630                 635                 640
Cys Leu Cys Gly Thr Ala Trp Leu Cys Cys Ser Pro Asn Arg Lys Asn
                645                 650                 655
Pro Leu Trp Pro Ser Val Pro Asp Pro Ala His Ser Ser Leu Gly Ser
            660                 665                 670
Trp Val Pro Thr Ile Met Glu Glu Asp Ala Phe Gln Leu Pro Gly Leu
        675                 680                 685
Gly Thr Pro Pro Ile Thr Lys Leu Thr Val Leu Glu Glu Asp Glu Lys
    690                 695                 700
Lys Pro Val Pro Trp Glu Ser His Asn Ser Ser Glu Thr Cys Gly Leu
```

```
705                 710                 715                 720
Pro Thr Leu Val Gln Thr Tyr Val Leu Gln Gly Asp Pro Arg Ala Val
                725                 730                 735

Ser Thr Gln Pro Gln Ser Gln Ser Gly Thr Ser Asp Gln Val Leu Tyr
                740                 745                 750

Gly Gln Leu Leu Gly Ser Pro Thr Ser Pro Gly Pro Gly His Tyr Leu
                755                 760                 765

Arg Cys Asp Ser Thr Gln Pro Leu Leu Ala Gly Leu Thr Pro Ser Pro
                770                 775                 780

Lys Ser Tyr Glu Asn Leu Trp Phe Gln Ala Ser Pro Leu Gly Thr Leu
785                 790                 795                 800

Val Thr Pro Ala Pro Ser Gln Glu Asp Asp Cys Val Phe Gly Pro Leu
                805                 810                 815

Leu Asn Phe Pro Leu Leu Gln Gly Ile Arg Val His Gly Met Glu Ala
                820                 825                 830

Leu Gly Ser Phe
            835

<210> SEQ ID NO 35
<211> LENGTH: 837
<212> TYPE: PRT
<213> ORGANISM: Mus musculus

<400> SEQUENCE: 35

Met Val Gly Leu Gly Ala Cys Thr Leu Thr Gly Val Thr Leu Ile Phe
1               5                   10                  15

Leu Leu Leu Pro Arg Ser Leu Glu Ser Cys Gly His Ile Glu Ile Ser
                20                  25                  30

Pro Pro Val Val Arg Leu Gly Asp Pro Val Leu Ala Ser Cys Thr Ile
                35                  40                  45

Ser Pro Asn Cys Ser Lys Leu Asp Gln Gln Ala Lys Ile Leu Trp Arg
            50                  55                  60

Leu Gln Asp Glu Pro Ile Gln Pro Gly Asp Arg Gln His His Leu Pro
65                  70                  75                  80

Asp Gly Thr Gln Glu Ser Leu Ile Thr Leu Pro His Leu Asn Tyr Thr
                85                  90                  95

Gln Ala Phe Leu Phe Cys Leu Val Pro Trp Glu Asp Ser Val Gln Leu
                100                 105                 110

Leu Asp Gln Ala Glu Leu His Ala Gly Tyr Pro Pro Ala Ser Pro Ser
            115                 120                 125

Asn Leu Ser Cys Leu Met His Leu Thr Thr Asn Ser Leu Val Cys Gln
        130                 135                 140

Trp Glu Pro Gly Pro Glu Thr His Leu Pro Thr Ser Phe Ile Leu Lys
145                 150                 155                 160

Ser Phe Arg Ser Arg Ala Asp Cys Gln Tyr Gln Gly Asp Thr Ile Pro
                165                 170                 175

Asp Cys Val Ala Lys Lys Arg Gln Asn Asn Cys Ser Ile Pro Arg Lys
            180                 185                 190

Asn Leu Leu Leu Tyr Gln Tyr Met Ala Ile Trp Val Gln Ala Glu Asn
        195                 200                 205

Met Leu Gly Ser Ser Glu Ser Pro Lys Leu Cys Leu Asp Pro Met Asp
    210                 215                 220

Val Val Lys Leu Glu Pro Pro Met Leu Gln Ala Leu Asp Ile Gly Pro
225                 230                 235                 240
```

-continued

```
Asp Val Val Ser His Gln Pro Gly Cys Leu Trp Leu Ser Trp Lys Pro
                245                 250                 255
Trp Lys Pro Ser Glu Tyr Met Glu Gln Glu Cys Glu Leu Arg Tyr Gln
            260                 265                 270
Pro Gln Leu Lys Gly Ala Asn Trp Thr Leu Val Phe His Leu Pro Ser
        275                 280                 285
Ser Lys Asp Gln Phe Glu Leu Cys Gly Leu His Gln Ala Pro Val Tyr
    290                 295                 300
Thr Leu Gln Met Arg Cys Ile Arg Ser Ser Leu Pro Gly Phe Trp Ser
305                 310                 315                 320
Pro Trp Ser Pro Gly Leu Gln Leu Arg Pro Thr Met Lys Ala Pro Thr
                325                 330                 335
Ile Arg Leu Asp Thr Trp Cys Gln Lys Lys Gln Leu Asp Pro Gly Thr
            340                 345                 350
Val Ser Val Gln Leu Phe Trp Lys Pro Thr Pro Leu Gln Glu Asp Ser
        355                 360                 365
Gly Gln Ile Gln Gly Tyr Leu Leu Ser Trp Asn Ser Pro Asp His Gln
    370                 375                 380
Gly Gln Asp Ile His Leu Cys Asn Thr Thr Gln Leu Ser Cys Ile Phe
385                 390                 395                 400
Leu Leu Pro Ser Glu Ala Gln Asn Val Thr Leu Val Ala Tyr Asn Lys
                405                 410                 415
Ala Gly Thr Ser Ser Pro Thr Thr Val Val Phe Leu Glu Asn Glu Gly
            420                 425                 430
Pro Ala Val Thr Gly Leu His Ala Met Ala Gln Asp Leu Asn Thr Ile
        435                 440                 445
Trp Val Asp Trp Glu Ala Pro Ser Leu Leu Pro Gln Gly Tyr Leu Ile
    450                 455                 460
Glu Trp Glu Met Ser Ser Pro Ser Tyr Asn Asn Ser Tyr Lys Ser Trp
465                 470                 475                 480
Met Ile Glu Pro Asn Gly Asn Ile Thr Gly Ile Leu Leu Lys Asp Asn
                485                 490                 495
Ile Asn Pro Phe Gln Leu Tyr Arg Ile Thr Val Ala Pro Leu Tyr Pro
            500                 505                 510
Gly Ile Val Gly Pro Pro Val Asn Val Tyr Thr Phe Ala Gly Glu Arg
        515                 520                 525
Ala Pro Pro His Ala Pro Ala Leu His Leu Lys His Val Gly Thr Thr
    530                 535                 540
Trp Ala Gln Leu Glu Trp Val Pro Glu Ala Pro Arg Leu Gly Met Ile
545                 550                 555                 560
Pro Leu Thr His Tyr Thr Ile Phe Trp Ala Asp Ala Gly Asp His Ser
                565                 570                 575
Phe Ser Val Thr Leu Asn Ile Ser Leu His Asp Phe Val Leu Lys His
            580                 585                 590
Leu Glu Pro Ala Ser Leu Tyr His Val Tyr Leu Met Ala Thr Ser Arg
        595                 600                 605
Ala Gly Ser Thr Asn Ser Thr Gly Leu Thr Leu Arg Thr Leu Asp Pro
    610                 615                 620
Ser Asp Leu Asn Ile Phe Leu Gly Ile Leu Cys Leu Val Leu Leu Ser
625                 630                 635                 640
Thr Thr Cys Val Val Thr Trp Leu Cys Cys Lys Arg Arg Gly Lys Thr
                645                 650                 655
Ser Phe Trp Ser Asp Val Pro Asp Pro Ala His Ser Ser Leu Ser Ser
```

```
                    660                 665                 670
Trp Leu Pro Thr Ile Met Thr Glu Glu Thr Phe Gln Leu Pro Ser Phe
            675                 680                 685

Trp Asp Ser Ser Val Pro Ser Ile Thr Lys Ile Thr Glu Leu Glu Glu
            690                 695                 700

Asp Lys Lys Pro Thr His Trp Asp Ser Glu Ser Ser Gly Asn Gly Ser
705                 710                 715                 720

Leu Pro Ala Leu Val Gln Ala Tyr Val Leu Gln Gly Asp Pro Arg Glu
                725                 730                 735

Ile Ser Asn Gln Ser Gln Pro Pro Ser Arg Thr Gly Asp Gln Val Leu
            740                 745                 750

Tyr Gly Gln Val Leu Glu Ser Pro Thr Ser Pro Gly Val Met Gln Tyr
            755                 760                 765

Ile Arg Ser Asp Ser Thr Gln Pro Leu Leu Gly Gly Pro Thr Pro Ser
            770                 775                 780

Pro Lys Ser Tyr Glu Asn Ile Trp Phe His Ser Arg Pro Gln Glu Thr
785                 790                 795                 800

Phe Val Pro Gln Pro Pro Asn Gln Glu Asp Asp Cys Val Phe Gly Pro
                805                 810                 815

Pro Phe Asp Phe Pro Leu Phe Gln Gly Leu Gln Val His Gly Val Glu
                820                 825                 830

Glu Gln Gly Gly Phe
            835

<210> SEQ ID NO 36
<211> LENGTH: 112
<212> TYPE: PRT
<213> ORGANISM: Rattus rattus

<400> SEQUENCE: 36

Leu Glu Gly Cys Gly Gln Ile Arg Ile Ser Pro Pro Ile Val His Leu
1               5                   10                  15

Gly Asp Pro Val Leu Ala Ser Cys Thr Ile Ser Pro Asn Cys Ser Lys
            20                  25                  30

Leu Asp Arg Gln Pro Lys Ile Leu Trp Arg Leu Gln Asp Glu Pro Asn
        35                  40                  45

Gln Pro Gly Asp Arg Gln His His Leu Pro Asp Gly Ser Gln Glu Ser
    50                  55                  60

Ile Ile Thr Leu Pro His Leu Asn Tyr Thr Gln Ala Phe Leu Phe Cys
65                  70                  75                  80

Leu Val Pro Trp Asn Asn Ser Phe Gln Val Leu Asp Gln Ala Glu Leu
                85                  90                  95

Arg Ala Gly Cys Lys Ser Leu Gln Pro Pro Thr His Leu Leu Gln Cys
            100                 105                 110

<210> SEQ ID NO 37
<211> LENGTH: 174
<212> TYPE: PRT
<213> ORGANISM: Homo sapiens

<400> SEQUENCE: 37

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
```

-continued

```
                35                  40                  45
Leu Leu Gly His Ser Leu Gly Ile Pro Trp Ala Pro Leu Ser Ser Cys
         50                  55                  60
Pro Ser Gln Ala Leu Gln Leu Ala Gly Cys Leu Ser Gln Leu His Ser
 65                  70                  75                  80
Gly Leu Phe Leu Tyr Gln Gly Leu Leu Gln Ala Leu Glu Gly Ile Ser
                 85                  90                  95
Pro Glu Leu Gly Pro Thr Leu Asp Thr Leu Gln Leu Asp Val Ala Asp
                100                 105                 110
Phe Ala Thr Thr Ile Trp Gln Gln Met Glu Glu Leu Gly Met Ala Pro
                115                 120                 125
Ala Leu Gln Pro Thr Gln Gly Ala Met Pro Ala Phe Ala Ser Ala Phe
            130                 135                 140
Gln Arg Arg Ala Gly Gly Val Leu Val Ala Ser His Leu Gln Ser Phe
145                 150                 155                 160
Leu Glu Val Ser Tyr Arg Val Leu Arg His Leu Ala Gln Pro
                165                 170

<210> SEQ ID NO 38
<211> LENGTH: 175
<212> TYPE: PRT
<213> ORGANISM: Homo sapiens

<400> SEQUENCE: 38

Met Thr Pro Leu Gly Pro Ala Ser Ser Leu Pro Gln Ser Phe Leu Leu
 1               5                  10                  15
Lys Cys Leu Glu Gln Val Arg Lys Ile Gln Gly Asp Gly Ala Ala Leu
                20                  25                  30
Gln Glu Lys Leu Cys Ala Thr Tyr Lys Leu Cys His Pro Glu Glu Leu
            35                  40                  45
Val Leu Leu Gly His Ser Leu Gly Ile Pro Trp Ala Pro Leu Ser Ser
         50                  55                  60
Cys Pro Ser Gln Ala Leu Gln Leu Ala Gly Cys Leu Ser Gln Leu His
 65                  70                  75                  80
Ser Gly Leu Phe Leu Tyr Gln Gly Leu Leu Gln Ala Leu Glu Gly Ile
                 85                  90                  95
Ser Pro Glu Leu Gly Pro Thr Leu Asp Thr Leu Gln Leu Asp Val Ala
                100                 105                 110
Asp Phe Ala Thr Thr Ile Trp Gln Gln Met Glu Glu Leu Gly Met Ala
                115                 120                 125
Pro Ala Leu Gln Pro Thr Gln Gly Ala Met Pro Ala Phe Ala Ser Ala
            130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro
                165                 170                 175

<210> SEQ ID NO 39
<211> LENGTH: 177
<212> TYPE: PRT
<213> ORGANISM: Homo sapiens

<400> SEQUENCE: 39

Thr Pro Leu Gly Pro Ala Ser Ser Leu Pro Gln Ser Phe Leu Leu Lys
 1               5                  10                  15
Cys Leu Glu Gln Val Arg Lys Ile Gln Gly Asp Gly Ala Ala Leu Gln
```

```
                20                  25                  30
Glu Lys Leu Val Ser Glu Cys Ala Thr Tyr Lys Leu Cys His Pro Glu
         35                  40                  45
Glu Leu Val Leu Leu Gly His Ser Leu Gly Ile Pro Trp Ala Pro Leu
 50                  55                  60
Ser Ser Cys Pro Ser Gln Ala Leu Gln Leu Ala Gly Cys Leu Ser Gln
 65                  70                  75                  80
Leu His Ser Gly Leu Phe Leu Tyr Gln Gly Leu Leu Gln Ala Leu Glu
                 85                  90                  95
Gly Ile Ser Pro Glu Leu Gly Pro Thr Leu Asp Thr Leu Gln Leu Asp
                100                 105                 110
Val Ala Asp Phe Ala Thr Thr Ile Trp Gln Gln Met Glu Glu Leu Gly
            115                 120                 125
Met Ala Pro Ala Leu Gln Pro Thr Gln Gly Ala Met Pro Ala Phe Ala
130                 135                 140
Ser Ala Phe Gln Arg Arg Ala Gly Gly Val Leu Val Ala Ser His Leu
145                 150                 155                 160
Gln Ser Phe Leu Glu Val Ser Tyr Arg Val Leu Arg His Leu Ala Gln
                165                 170                 175
Pro

<210> SEQ ID NO 40
<211> LENGTH: 1155
<212> TYPE: DNA
<213> ORGANISM: Rattus rattus

<400> SEQUENCE: 40
atgagcatca ttccctgcc tcagctcctc gccctgctct gctgctgcgg acttgctgct      60
gctactcagg gccccacaga cccgtccacg ccccctaacc tgggcctcgc ccacttccac     120
aacctgacct tcgaccccgg gacctggaca ctgagctggg cctgtggcgg ccatgatggg     180
gcagtgatgt cgtgcacggt gattgaccag gaggcaggga tccggcgcag agtgcggtcc     240
cggggctgcc gctgccggtt tcagccaatg gagttacacc gcggggtcga cctggaggtt     300
gcggggaca aggccatgc caagtccat cagactctgc gcttcgagaa tgaaggtgcc        360
ccaggctccg gggcagagaa cctgacctgt gagatccttg ctgcccactt cctgtgctgt     420
tattgggcgg tggggccggc tgcacccgat gacatcagat actcactgcg cgtgctcaac     480
gccactggtc atgaggtcgc cagctgctcc gctgccccg gaaccccacc cacgcgttgc      540
caggctgatg atctcacaca tctgccccgc ctcgcataca tcgtcgtcac tgggcagagc     600
cggacggggc tggtgcggtt cctggatgcc gtggtcaaca ccaagggcat tgagcgcctg     660
ggtcccccag ataacgtctc tgcctcctgt aacttctccc actgcaccat cacctgggct     720
ccgccccta cctgggcgcc tatgacggaa caggatttcc gctttgagat cgagtggaag     780
aaggcggagc ccagcagcat tgcccagaag gtggttatcg cagggcgcga ggacaacgcc     840
ttcgccttcc ccagccccgc ccccgtggc cgctctgggt cagagttcg tgcagggggac      900
acacgcagtg atcggtggag cgactggagc ccgccctgg agctcggctc ggaggccaca      960
accccgccgc gggccctggt gttggcggcg tcgagctgtg cagccctgct gtgtgcgctg    1020
gcactggggg cggcctgcag gagactcgcg ctctcacgcc gcctcctccc cccatcccc    1080
gggatccggg accgcgtatc tgatgacgag cgtgtcaact cggagacgct gaggaaggac    1140
ctgctgcggc cctag                                                    1155
```

```
<210> SEQ ID NO 41
<211> LENGTH: 384
<212> TYPE: PRT
<213> ORGANISM: Rattus rattus

<400> SEQUENCE: 41

Met Ser Ile Ile Pro Leu Pro Gln Leu Leu Ala Leu Leu Cys Cys Cys
1               5                   10                  15

Gly Leu Ala Ala Ala Thr Gln Gly Pro Thr Asp Pro Ser Thr Pro Pro
            20                  25                  30

Asn Leu Gly Leu Ala His Phe His Asn Leu Thr Phe Asp Pro Gly Thr
        35                  40                  45

Trp Thr Leu Ser Trp Ala Cys Gly Gly His Asp Gly Ala Val Met Ser
50                  55                  60

Cys Thr Val Ile Asp Gln Glu Ala Gly Ile Arg Arg Val Arg Ser
65                  70                  75                  80

Arg Gly Cys Arg Cys Arg Phe Gln Pro Met Glu Leu His Arg Gly Val
                85                  90                  95

Asp Leu Glu Val Ala Gly Asp Lys Gly His Ala Gln Val His Gln Thr
            100                 105                 110

Leu Arg Phe Glu Asn Glu Gly Ala Pro Gly Ser Gly Ala Glu Asn Leu
        115                 120                 125

Thr Cys Glu Ile Leu Ala Ala His Phe Leu Cys Cys Tyr Trp Ala Val
    130                 135                 140

Gly Pro Ala Ala Pro Asp Asp Ile Arg Tyr Ser Leu Arg Val Leu Asn
145                 150                 155                 160

Ala Thr Gly His Glu Val Ala Ser Cys Ser Ala Ala Pro Gly Thr Pro
                165                 170                 175

Pro Thr Arg Cys Gln Ala Asp Asp Leu Thr His Leu Pro Arg Leu Ala
            180                 185                 190

Tyr Ile Val Val Thr Gly Gln Ser Arg Thr Gly Leu Val Arg Phe Leu
        195                 200                 205

Asp Ala Val Val Asn Thr Lys Gly Ile Glu Arg Leu Gly Pro Pro Asp
    210                 215                 220

Asn Val Ser Ala Ser Cys Asn Phe Ser His Cys Thr Ile Thr Trp Ala
225                 230                 235                 240

Pro Pro Pro Thr Trp Ala Pro Met Thr Glu Gln Asp Phe Arg Phe Glu
                245                 250                 255

Ile Glu Trp Lys Lys Ala Glu Pro Ser Ser Ile Ala Gln Lys Val Val
            260                 265                 270

Ile Ala Gly Arg Glu Asp Asn Ala Phe Ala Phe Pro Ser Pro Ala Pro
        275                 280                 285

Arg Gly Arg Leu Trp Val Arg Val Arg Ala Gly Asp Thr Arg Ser Asp
    290                 295                 300

Arg Trp Ser Asp Trp Ser Pro Ala Leu Glu Leu Gly Ser Glu Ala Thr
305                 310                 315                 320

Thr Pro Pro Arg Ala Leu Val Leu Ala Ala Ser Ser Cys Ala Ala Leu
                325                 330                 335

Leu Cys Ala Leu Ala Leu Gly Ala Ala Cys Arg Arg Leu Ala Leu Ser
            340                 345                 350

Arg Arg Leu Leu Pro Pro Ile Pro Gly Ile Arg Asp Arg Val Ser Asp
        355                 360                 365
```

```
-continued

Asp Glu Arg Val Asn Ser Glu Thr Leu Arg Lys Asp Leu Leu Arg Pro
    370                 375                 380
```

METHODS OF TREATING NEUROLOGICAL CONDITIONS WITH HEMATOPOIETIC GROWTH FACTORS

BACKGROUND OF THE INVENTION

1. Field of the Invention

The present invention relates to a method of treating neurological conditions in a mammal by administering a hematopoietic growth factor such as granulocyte-colony stimulating factor (GCSF), granulocyte-macrophage colony stimulating factor (GMCSF), and/or other hematopoetic factors, for example, MCSF except for erythropoietin (EPO). The invention also provides methods of screening for compounds that bind to a GCSF or GMCSF receptor found on the surface of a neuronal cell; and which provides a neuroprotective, neuroproliferative and/or a STAT gene activation activity.

2. Discussion of the Related Art

Growth factors are proteins that are essentially involved in regulating survival, proliferation, maturation, and outgrowth of developing neuronal cells. For example, the expression of a large number of growth factors increases in response to various brain insults. Many factors display endogenous neuroprotective and neurotrophic effects (see Arvidsson A et al., *Neuroscience* 2001; 106:27-41; Larsson E, et al., *J Cereb Blood Flow Metab* 1999; 19:1220-8; Mattson M P, et al., *J Neurotrauma* 1994; 11:3-33; Semkova I, et al., *Brain Res Brain Res Rev* 1999; 30:176-88). These effects were also reported after exogenous administration in vitro and in vivo after brain trauma and stroke (see Semkova I., et al., *Brain Res. Rev.* 1999; 30:176-88; Fisher M, et al., *J Cereb. Blood Flow Metab.* 1995; 15:953-9; Schäbitz W R et al., *Stroke* 2001; 32:1226-33; Schäbitz W R, et al., *Stroke* 2000; 31:2212-7). After binding to high-affinity membrane receptors the effects of growth factors are mediated by a cascade of intracellular signal-transduction events (Kemie S G. et al., *Arch Neurol* 2000; 57:654-7), which induces cells to grow and differentiate; or provides trophic support for cell survival.

Granulocyte-colony stimulating factor (GCSF), a 20 kDa protein, together with tumor necrosis factor-α (TNF-α) and the interleukins is a member of the cytokine family of growth factors. GCSF is the major growth factor involved in the production of neutrophilic granulocytes.

GCSF exerts its function via the activation of a membrane receptor (GCSF receptor) that belongs to the super-family of hematopoietin receptors, also being referred to as class I cytokine receptors (de Koning and Touw, *Curr. Opin. Hematol.*, 1996, 3, 180-4).

A number of receptors for lymphokines, hematopoietic growth factors, and growth hormone-related molecules have been found to share a common binding domain. These receptors are referred to as hematopoietin receptors and the corresponding ligands as hematopoietins. Further, hematopoietins have been subdivided into two major structural groups: Large/long and small/short hematopoietins. One subset of individual receptor chains that are part of receptor complexes for large hematopoietins contain common structural elements in their extracellular parts: an immunoglobin-like domain, a hematopoietin-receptor domain, and 3 fibronectin type-III domains (2 in the leptin receptor). This subgroup was designated the "gp130 family of receptors" (Mosley, et al., *J. Biol. Chem.* 1996, 271, 32635-43) and include Leptin receptor (LPTR), Granulocyte colony stimulating factor receptor (GCSFR), Interleukin-6/-11/LIF/OSM/CNTF common beta chain (GP130), Leukemia inhibiting factor receptor (LIFR), Oncostatin-M receptor beta chain (OSMR), Interleukin-12 receptor beta-1 chain (IL12RB1), Interleukin-12 receptor beta-2 chain (IL12RB2). These receptor chains homodimerize (GCSFR, GP130, LPTR) or heterodimerize (GP130 with LIFR or OSMR, IL12RB1 with IL12RB2) upon binding the cognate cytokine. In addition, a prosite consensus pattern is characteristic of this receptor family, which is:

N-x(4-S-x(28,35)-[LVIM]-x-W-x(0,3)—P-x(5,9)-[YF]-x (1,2)-[VILM]-x-W (SEQ ID NO:1)

GCSF stimulates proliferation, survival, and maturation of cells committed to the neutrophilic granulocyte lineage through binding to the specific GCSF receptor (GCSFR) (see Hartung T., et al., *Curr. Opin. Hematol.* 1998; 5:221-5). GCSFR mediated signaling activates the family of Signal Transducer and Activator of Transcription (STAT) proteins which translocate to the nucleus and regulate transcription (Darnell J E Jr., *Science* 1997; 277:1630-5). GCSF is typically used for the treatment of different kinds of neutropenia in humans. It is one of the few growth factors approved for clinical use. In particular, it is used to reduce chemotherapy (CT)-induced cytopenia (Viens et al., *J. of Clin. Oncology*, Vol. 20, No. 1, 2002:24-36). GCSF has also been implicated for therapeutic use in infectious diseases as potential adjunctive agent (Hübel et al., *J. of Infectious Diseases*, Vol. 185: 1490-501, 2002). GCSF has reportedly been crystallized to some extent (EP 344 796), and the overall structure of GCSF has been surmised, but only on a gross level (Bazan, *Immunology Today* 11: 350-354 (1990); Parr et al. *J. Molecular Recognition* 8: 107-110 (1988)).

In recent years a number of growth factors such as bFGF and pharmaceutically promising substances such as thrombocyte adhesion blockers like anti-GP IIb/IIa and Abcizimab have been tested for neuroprotective efficacy in clinical studies. Unfortunately, none of these prevailed in the clinical studies. In particular, NMDA antagonists, free radical scavengers and glutamate antagonists failed or demonstrated severe side-effects. The list of substances such as anti-ICAM or inhibitors of the glutamate-mediated NO-synthetase that have tested positive in cell-based assays and animal models but failed in clinical studies is getting increasingly longer (De Keyser, et al. (1999), *Trends Neurosci*, 22, 535-40).

Most studies on cerebral ischemia and testing of pharmacological substances in vivo have only been concerned with the immediate effects of the drug or paradigm under investigation (i.e. infarct size 24 h after induction of the stroke). However, a more valid parameter of true efficacy of a particular substance is the long-term effect on functional recovery, which is also reflected in human stroke studies, where clinical scales (e.g., Scandinavian stroke scale, NIH scale, Barthel index) also reflect the ability to perform daily life activities. Recovery in the first few days after focal lesions may be due to resolution of edema or reperfusion of the ischemic penumbra. Much of the functional recovery after the acute phase is likely due to brain plasticity, with adjacent cortical areas of the brain taking over functions previously performed by the damaged regions (Chen R, Cohen L G, Hallett M. *Neuroscience* 2002; 111(4):761-73). The two main mechanisms proposed to explain reorganization are unmasking of previously present but functionally inactive connections and growth of new connections such as collateral sprouting (Chen R, Cohen L G, Hallett M. 2002 *Neuroscience* 2002; 111(4): 761-73). Short term plastic changes are mediated by removing inhibition to excitatory synapses, which is likely due to reduced GABAergic inhibition (Kaas J H. *Annu Rev Neurosci.* 1991; 14:137-67; Jones E G. *Cereb Cortex.* 1993 September-October; 3(5):361-72.). Plasticity changes that occur over a longer time involve mechanisms in addition to the unmasking of latent synapses such as long-term potentiation (LTP), which requires NMDA receptor activation and increased intracellular calcium concentration (Hess and Donoghue, *J Neurophysiol.* 1994 71(6):2543-7). Long term changes also involve axonal regeneration and sprouting with alterations in synapse shape, number, size and type (Kaas J H. *Annu Rev Neurosci.* 1991; 14:137-67, 3:).

Stroke is the third-leading cause of death, and the main cause of disability in the western world. It presents a large socioeconomic burden. The etiology can be either ischemic (in the majority of cases) or hemorraghic. The cause of ischemic stroke is often embolic, or thrombotic. So far, there is no effective treatment for the majority of stroke patients. The only clinically proven drugs so far are tissue plasminogen activator (TPA) and Aspirin. After massive cell death in the immediate infarct core due to lack of glucose and oxygen, the infarct area expands for days, owing to secondary mechanisms such as glutamate excitotoxicity, apoptotic mechanisms, and generation of free radicals.

Amyotrophic lateral sclerosis (ALS; Lou-Gehrig's disease; Charcot's disease) is a neurodegenerative disorder with an annual incidence of 0.4 to 1.76 per 100.000 population (Adams et al., *Principles of Neurology*, 6$^{th}$ ed., New York, pp 1090-1095). It is the most common form of motor neuron disease with typical manifestations of generalized fasciculations, progressive atrophy and weakness of the skeletal muscles, spasticity and pyramidal tract signs, dysarthria, dysphagia, and dyspnea. The pathology consists principally in loss of nerve cells in the anterior horn of the spinal cord and motor nuclei of the lower brainstem, but can also include the first order motor neurons in the cortex. Pathogenesis of this devastating disease is still largely unknown, although the role of superoxide-dismutase (SOD 1) mutants in familial cases has been worked out quite well, which invokes an oxidative stress hypothesis. So far, more than 90 mutations in the SOD1 protein have been described, that can cause ALS (Cleveland and Rothstein (2001), *Nat Rev Neurosci,* 2, 806-19). Also, a role for neurofilaments in this disease was shown. Excitotoxicity, a mechanism evoked by an excess glutamate stimulation is also an important factor, exemplified by the beneficial role of Riluzole in human patients. Most convincingly shown in the SOD1 mutants, activation of caspases and apoptosis seems to be the common final pathway in ALS (Ishigaki, et al. (2002), *J Neurochem,* 82, 576-84, Li, et al. (2000), *Science,* 288, 335-9). Therefore, it seems that ALS also falls into the same general pathogenetic pattern that is also operative in other neurodegenerative diseases and stroke, e.g. glutamate involvement, oxidative stress, and programmed cell death.

Parkinson's disease is the most frequent movement disorder, with approximately 1 million patients in North America; about 1 percent of the population over the age of 65 years is affected. The core symptoms of the disease are rigor, tremor and akinesia (Adams et al., Principles of Neurology, 6$^{th}$ ed., New York, pp 1090-1095). The etiology of Parkinson's disease is not known. Nevertheless, a significant body of biochemical data from human brain autopsy studies and from animal models points to an ongoing process of oxidative stress in the substantia nigra, which could initiate dopaminergic neurodegeneration. Oxidative stress, as induced by the neurotoxins 6-hydroxydopamine and MPTP (N-methyl-4-phenyl-1,2,3,6-tetrahydropyridine), has been used in animal models to investigate the process of neurodegeneration. Although a symptomatic therapy exists (e.g. L-DOPA plus a decarboxylase inhibitor; bromocriptine, pergolide as dopamin agonists; and anticholinergic agents such as trihexyphenidyl (artane)), there is a clear need for a causative therapy, e.g. a neuroprotective therapy, that really halts the disease progress. These animal models have been used to test the efficacy of radical scavengers, iron chelators, dopamine agonists, nitric oxide synthase inhibitors and certain calcium channel antagonists. Apoptotic mechanisms are clearly operative in the animal models as well as in the patient (Mochizuki, et al. (2001), *Proc. Natl. Acad. Sci. USA,* 98, 10918-23, Xu et al. (2002), *Nat. Med.,* 8, 600-6, Viswanath, et al. (2001), *J. Neurosci.,* 21, 9519-28, Hartmann, et al. (2002), *Neurology,* 58, 308-10). This pathophysiology with involvement of oxidative stress and apoptosis also places Parkinson's disease amongst the other neurodegenerative disorders and stroke.

Cerebral ischemia may result from a variety of causes that impair cerebral blood flow (CBF) and lead to deprivation of both oxygen and glucose. Traumatic brain injury (TBI), on the other hand, involves a primary mechanical impact that usually causes skull fracture and abruptly disrupts the brain parenchyma with shearing and tearing of blood vessels and brain tissue. This, in turn, triggers a cascade of events characterized by activation of molecular and cellular responses that lead to secondary injury. The evolution of such secondary damage is an active process in which many biochemical pathways are involved (Leker and Shohami (2002), *Brain Res. Rev.,* 39, 55-73). Many similarities between the harmful pathways that lead to secondary cellular death in the penumbral ischemic zone and in the area exposed to secondary post-traumatic injury have been identified (e.g. excitotoxity by excess glutamate release, nitric oxide, reactive oxygen species, inflammation, and apoptosis (Leker and Shohami (2002), *Brain Res. Rev.,* 39, 55-73)). In addition, early ischemic episodes are reported to occur after traumatic brain injury, adding a component of ischemia to the primary mechanical damage.

Cardiovascular disease is the major cause of death in western industrialized nations. In the United States, there are approximately 1 million deaths each year with nearly 50% of them being sudden and occurring outside the hospital (Zheng, et al. (2001), *Circulation,* 104, 2158-63). Cardio-pulmonary resuscitation (CPR) is attempted in 40-90 of 100,000 inhabitants annually, and restoration of spontaneous circulation (ROSC) is achieved in 25-50% of these patients. However, the hospital discharge rate following successful ROSC is only 2-10% (Bottiger, et al. (1999), *Heart,* 82, 674-9). Therefore, the vast majority of the cardiac arrest victims annually in the United States is not treated successfully. The major reason for the low survival rates after successful CPR, i.e., for postarrest in-hospital mortality, is persistent brain damage. Brain damage following cardiocirculatory arrest is related both to the short period of tolerance to hypoxic stress and to specific reperfusion disorders (Safar (1986), *Circulation,* 74, IV138-53, Hossmann (1993), *Resuscitation,* 26, 225-35). Initially, a higher number of patients can be stabilized hemodynamically after cardiocirculatory arrest; many of them, however, die due to central nervous system injury. The personal, social, and economic consequences of brain damage following cardiac arrest are devastating. One of the most important issues in cardiac arrest and resuscitation ("whole body ischemia and reperfusion") research, therefore, is cerebral resuscitation and postarrest cerebral damage (Safar (1986), *Circulation,* 74, IV138-53, Safar, et al. (2002), *Crit Care Med,* 30, p. 140-4). Presently, it is not possible to decrease the primary damage to neurons that is caused by hypoxia during cardiac arrest by any post-arrest therapeutic measures. Major pathophysiological issues include hypoxia and subsequent necrosis, reperfusion injury with free radical formation and cellular calcium influx, release of excitatory amino acids, cerebral microcirculatory reperfusion disorders, and programmed neuronal death or apoptosis (Safar (1986), *Circulation,* 74, IV138-53, Safar et al. (2002), *Crit Care Med,* 30, 140-4).

Several clinical trials have attempted to improve neurological outcome after cardiac arrest without success. The therapeutic use of barbiturates (to enhance neuroprotection) or the use of calcium channel blockers (to reduce ischemia reperfusion damage) was tested (Group (1986), *Am. J. Emerg. Med.,* 4, 72-86, Group (1986), *N. Engl. J. Med.,* 314, 397-403, Group (1991), *Control Clin. Trials,* 12, 525-45, Group (1991), *N. Engl. J. Med.,* 324, 1225-31). To date no specific post-arrest treatment options are available to improve neurological outcome following cardiocirculatory arrest in the clinical setting (with the possible exception of mild hypothermia and thrombolysis where the results of large, randomized, and controlled clinical trials are eagerly awaited (Safar et al (2002), *Crit. Care Med.,* 30, 140-4)). Therefore, an innovative therapy to improve neurological outcome after cardiac arrest is crucial.

Multiple sclerosis is the prototype inflammatory autoimmune disorder of the central nervous system and, with a lifetime risk of one in 400, potentially the most common cause of neurological disability in young adults. Worldwide, there are about 2-5 million patients suffering from this disease (Compston and Coles (2002), *Lancet,* 359, 1221-31.). As with all complex traits, the disorder results from interplay between as yet unidentified environmental factors and susceptibility genes. Together, these factors trigger a cascade of events, involving engagement of the immune system, acute inflammatory injury of axons and glia, recovery of function and structural repair, post-inflammatory gliosis, and neurodegeneration. The sequential involvement of these processes underlies the clinical course characterized by episodes with recovery, episodes leaving persistent deficits, and secondary progression. The aim of treatment is to reduce the frequency, and limit the lasting effects of relapses, relieve symptoms, prevent disability arising from disease progression, and promote tissue repair.

Schizophrenia is one of the most common mental illnesses. About 1 of every 100 people (1% of the population) is affected by schizophrenia. This disorder is found throughout the world and in all races and cultures. Schizophrenia affects men and women in equal numbers, although on average, men appear to develop schizophrenia earlier than women. Generally, men show the first signs of schizophrenia in their mid 20s and women show the first signs in their late 20s. Schizophrenia has a tremendous cost to society, estimated at $32.5 billion per year in the US. Schizophrenia is characterized by several of the following symptoms: delusions, hallucinations, disorganized thinking and speech, negative symptoms (social withdrawal, absence of emotion and expression, reduced energy, motivation and activity), catatonia. The main therapy for schizophrenia is based on neuroleptics, such as chlorpromazine, haloperidol, olanzapine, clozapine, thioridazine, and others. However, neuroleptic treatment often does not reduce all of the symptoms of schizophrenia. Moreover, antipsychotic treatment can have severe side effects, such as tardive dyskinesias. The etiology of schizophrenia is not clear, although there seems to be a strong genetic influence. Recently, it has become clear that schizophrenia has at least some aspects of a neurodegenerative disease. In particular, MR studies have revealed rapid cortical grey matter loss in schizophrenic patients (Thompson, et al. (2001), *Proc Natl Acad Sci USA,* 98, 11650-5; Cannon, et al. (2002), *Proc Natl Acad Sci USA,* 99, 3228-33). Therefore, treatment of schizophrenics with neuroprotective medication such as GCSF or GMCSF or other hematopoetic factors is warranted.

In view of the above, there is a need for treating neurological and/or psychiatric conditions, such as neurological diseases that relate to the enhancement of plasticity and functional recovery, or cell-death in the nervous system. In particular, there is a need for treating neurological diseases by providing neuroprotection to the neural cells involved.

SUMMARY OF THE INVENTION

Accordingly, one object of the present invention is to provide a method of treating a neurological or a psychiatric condition in a mammal by administering to the mammal a hematopoietic factor such as GMCSF, a GMCSF derivative, GCSF, a GCSF derivative, and combinations thereof, or cells secreting GCSF or GMCSF or derivatives, to treat the condition.

Another object of the present invention is to provide a method of treating a neurological condition in a mammal, by conditioning a neural stem cell composition with a hematopoietic factor such as GMCSF, a GMCSF derivative, GCSF, a GCSF derivative, and combinations thereof; and subsequently administering the neural stem cells to a mammal for the treatment of the condition.

Another object of the present invention is to provide a method for identifying a compound that binds to the granulocyte colony stimulating factor receptor (GCSFR) on neuronal cells and which activates STAT in the neuronal cell by contacting the neuronal cell with the compound; and measuring an increase in STAT activation relative to STAT activation in a neuronal cell which has not been contacted with the compound and determining the activation relative to, for example, GCSF mediated STAT activation. Further, compounds obtained by this method as well as methods of using the compounds to treat neurological conditions are additional objects of the present invention.

Another object of the present invention is to provide a method for identifying a compound that binds to the granulocyte macrophage colony stimulating factor receptor (GMCSFR) on neuronal cells and/or which activates STAT gene expression in the neuronal cell by contacting the neuronal cell with the compound; and measuring an increase in STAT activation relative to STAT gene activation in a neuronal cell which has not been contacted with the compound. Further, compounds obtained by this method as well as methods of using the compounds to treat neurological conditions are additional objects of the present invention.

Another object of the present invention is to provide a method for identifying a GCSF receptor agonist with improved neuroprotective activity by contacting the compound with a neural cell having a GCSF receptor, measuring the neuroprotective effect of the compound to the neural cell, and comparing the effect of the compound to the effect of GCSF. Further, compounds obtained by this method as well as methods of using the compounds to treat neurological conditions are additional objects of the present invention.

Another object of the present invention is to provide a method for identifying a GMCSF receptor agonist with improved neuroprotective activity by contacting the compound with a neural cell having a GMCSF receptor, measuring the neuroprotective effect of the compound to the neural cell, and comparing the effect of the compound to the effect of GMCSF. Further, compounds obtained by this method as well as methods of using the compounds to treat neurological conditions are additional objects of the present invention.

Another object of the present invention is to provide a method for identifying a compound with improved GCSF receptor agonist activity by contacting the compound with a neural cell having a GCSF receptor, comparing the level of STAT gene expression in the neural cell to a second neural cell contacted with GCSF. Further, compounds obtained by this method as well as methods of using the compounds to treat neurological conditions are additional objects of the present invention.

Another object of the present invention is to provide a method for identifying a compound with improved GMCSF receptor agonist activity by contacting the compound with a neural cell having a GMCSF receptor, comparing the level of STAT gene expression in the neural cell to a second neural cell contacted with GMCSF. Further, compounds obtained by this method as well as methods of using the compounds to treat neurological conditions are additional objects of the present invention.

Another object of the present invention is to provide a method of stimulating GCSF or GMCSF expression and/or the release in endogenous neural cells by by agonizing a GCSF or GMCSF receptor present on the cell. In another embodiment, the cells are contacted with a substance that increases the expression and/or release of GCSF or GMCSF. Such methods can employ assays which detect the release or increased expression of GCSF and/or GMCSF in neural cells, e.g., neural cell cultures (for example, PCR and/or ELISA assays).

Another object of the present invention is to provide a method of treating a neurological condition in a mammal by agonizing a GMCSF receptor, a GCSF receptor, or both receptors to treat the neurological condition.

Another object of the present invention is to provide a method of enhancing the survival of a cell transplanted into a mammal, by introducing into the cell one or more polynucleotides which encode GMCSF, a GMCSF derivative, GCSF, a GCSF derivative, and/or combinations thereof prior to transplanting the cell into the mammal, whereby the cell expresses the hematopoietic factor in an amount sufficient to enhance the survival of the cell relative to the cell survival prior to the introduction of the polynucleotides.

Another object of the present invention is to provide a method of enhancing the viability of a neural cell culture by providing GMCSF, a GMCSF derivative, GCSF, a GCSF derivative, and/or combinations thereof to enhance the viability of the neural cell culture relative to the culture prior to providing the hematopoietic factor. In such a method, the hematopoietic factors can be used to contact the cells of the culture or may be provided using polynucleotides that encode and express the hematopoietic factors.

BRIEF DESCRIPTION OF THE DRAWINGS

FIG. 4 Immunohistochemistry showing the distribution of GCSF-receptor in different brain regions in the mouse (paraffin sections, 2 μm). a-d: localization of GCSF-R in the hippocampus. Note that the antibody predominantly stains neurons in the CA3 area (a,b), with a sharp boundary between the CA3 and CA2 region (c, arrow). GCSF-R is distributed over the soma, as well as processes of neurons (b, arrow). Note the presence of the receptor in the hilus and the basal cell layers of the dentate gyrus (d, arrow). GCSF-Receptor was also detected in cortical areas: piriform cortex (e), and perirhinal cortex (f) as examples. In the cerebellum, Purkinje cells are labeled (g, arrow). Also, some of the large mitral cells in the olfactory bulb are GCSF-R positive (h, arrow). Strong staining is exhibited by the anterior columns in the spinal cord (i, j), and higher magnification identifies the large motoneurons as GCSF-R positive (k,l). Note that the neuronal processes are strongly labeled. In the midbrain, neurons in the substantia nigra show GCSF-R positivity (m). Especially, all neurons in the pars compacta (SNC) are labeled (arrow in m, and n). Also, in the pars reticulata, several neurons express GCSF-R(O). Apart from neurons, oligodendrocytes in white matter tracts are stained, for example, in the anterior commissure (p, arrow). Surprisingly, the staining of the GCSF ligand (antibody sc13102, Santa Cruz) colocalizes with the expression of its receptor (antibody sc694, Santa Cruz) (FIG. 4$q$-$u$). This argues for a autocrine mechanism as a protective measure of neurons against noxious stimuli. In the hippocampus, the same subfield specificity is observed for the GCSF ligand (q: GCSFR, r: GCSF, arrows point to the border between subfields CA 2-3, ca3 and ca2 labels indicate the subfield). This specificity coincides with known differences in susceptibilities of these regions against ischemic damage, and argues again for a neuroprotective function of the GCSF system. Also, in the dentate gyrus, the same interesting pattern of expression in the hilus and the subgranular zone is observed (FIG. 4$s$, GCSF receptor; FIG. 4$t$, GCSF; arrows point to one neuron in the subgranular zone, labels: s: subgranular zone, h: hilus of the dentate gyrus), which underlines the importnace of the GCSF system for neurogenesis, and nicely parallels the expression of receptor and ligand on neurospheres (see FIG. 13). Interestingly, GCSF is also expressed in the large motoneurons of the spinal cord (FIG. 4$u$) where its receptor is also expressed (FIG. 4$i$-$l$).

FIG. 6: STAT3 immunohistochemistry. Note, that numerous neuronal nuclei are positively stained in the cortical penumbra of GCSF treated rats (b, arrows) compared to the cortical periinfarct area of a placebo treated animal (a, arrows; left: infarct; right: penumbra; original magnification×200). FIG. 7: Cortical neurons in the unaffected contralateral side (CL) and ipsilateral in the vicinity of the infarction (IL) were quantified in GCSF treated animals and controls. There was a significant activation of STAT3 in neurons adjacent to the infarction in the GCSF-treated group as quantified by counting neurons with nuclear translocation of STAT3 (*$p<0.05$, t-test).

FIG. 8 shows the effect of GCSF treatment in the photothrombotic bengal rose model of cerebral ischemia. A, rotarod performance; B, neurological score, including beam balance; C, D: adhesive tape removal test, measured on the ipsi- (C), as well as contralateral side (D). Legend: ischemia: group of ischemic rats, non-treated; ischemia+GCSF: group of ischemic rats treated with GCSF; sham+GCSF: sham-operated animals, treated with GCSF; sham: sham-operated animals, untreated. L: tape-removal test on the left paw; R: tape-removal test on the right paw. Note that there is an effect on both sides in the tape-removal test (C,D), probably caused by a predominant motor deficit when the tape is on the ipsilateral side, and a predominant sensor deficit, when the tape is on the contralateral side.

FIG. 9 shows the upregulation of the GCSF-Receptor in the bengal-rose model 48 h after induction of photothrombosis on the contralateral side to the ischemia. A, scheme of a coronal section of a rat brain, tissue samples 3 and 4 were used for the quantification of the GCSF receptor mRNA compared to the same tissue samples from sham-operated rats. B, quantification of GCSF receptor mRNA in the cortical penumbral samples (samples 3 and 4 from A). An initial upregulation at 6 h after ischemia induction on the ipsilateral side is followed by an upregulation on the contralateral side at 48 h after the infarct. This contralateral upregulation was also seen with the GMCSF receptor (see below).

FIG. 10 shows an alignment of the GCSF from different species using the ClustalW algorithm (SEQ ID NOS:28-33) (MEGALIGN™, Lasergene, Wis.).

FIG. 11 shows an alignment of GCSF receptors from mouse and human, and a fragment of rat using the ClustalW algorithm (SEQ ID NOS: 34-36) (MEGALIGN™, Lasergene, Wis.).

FIG. 14 demonstrates the rapid uptake of biotinylated GCSF after intraperitoneal injection into mice. A, Western blot of serum from mice sacrificed at 1, 2, 4, 6, 20, 28 h post injection of 7.5 ug GCSF/mouse. B, ELISA of Serum GCSF after i.p. injection. There is rapid uptake of GCSF from the peritoneum with serum peak levels at 2 hrs., demonstrating applicability of this administration route.

FIG. 15 shows the identification of the GMCSF-Receptor as an upregulated mRNA after induction of photothrombosis (bengal rose model) on the ipsilateral and contralateral side to the ischemia. A shows a schematic coronal section of a mouse brain and areas of interest are marked in grey; B shows a section of an RMDD-Gel, on which the transcript of the GMCSF-Receptor was identified as being regulated. The lanes represent RT-PCR-products on RNA samples of mouse brain. Samples were taken from cortex penumbra at different timepoints after the stroke (3 and 4 in A, respectively).

Figure 17:
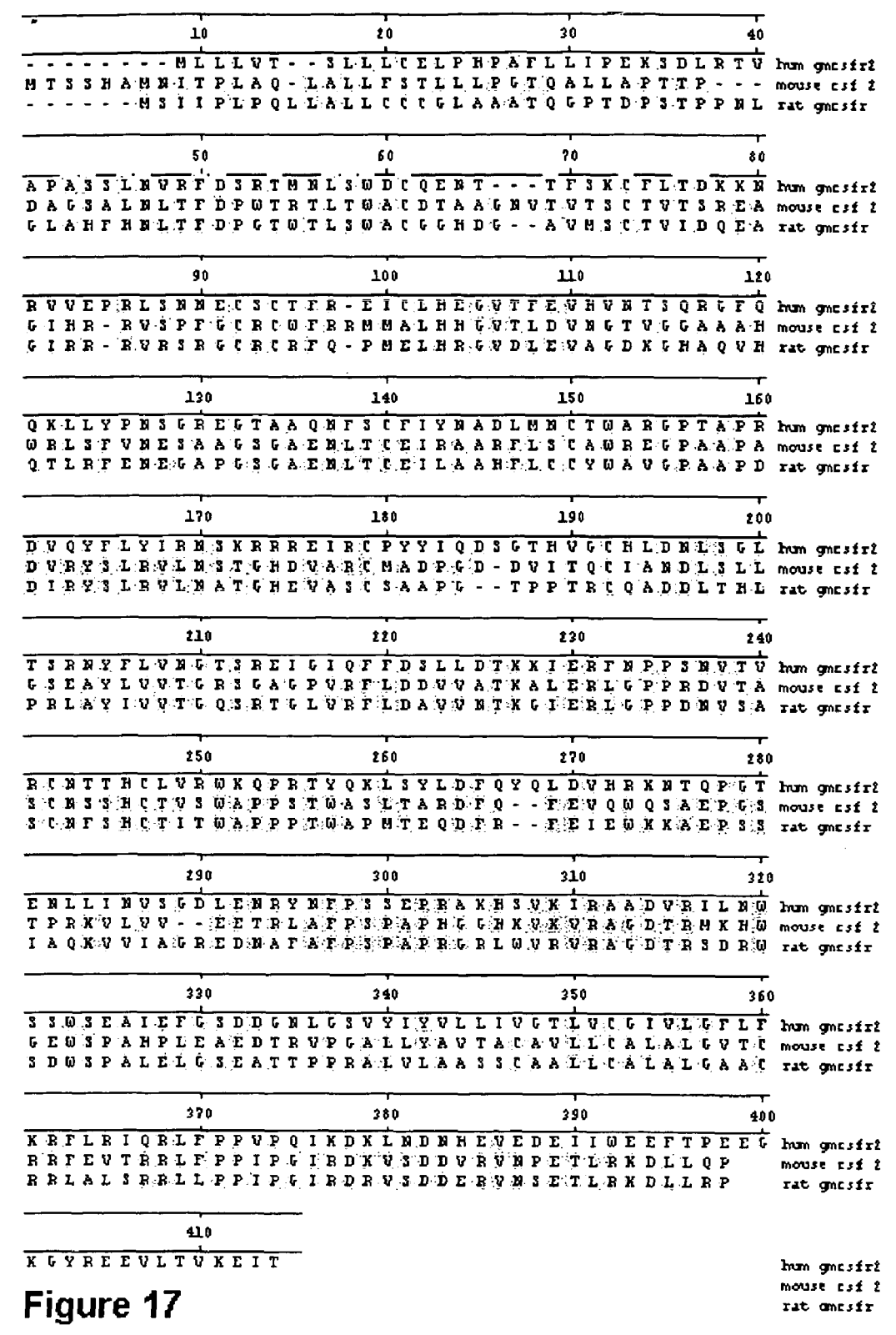

FIG. 17 shows an alignment of GMCSF receptors from human, mouse, and the sequence from rat identified as an upregulated transcript (SEQ ID NOS:22, 23 and 24) (ClustalW algorithm, MEGALIGN™, Lasergene, Wis.). It is concluded from this homology that the identified sequence is the rat GMCSF receptor.

FIG. 18 shows an alignment of GMCSF from human, mouse, and rat (SEQ ID NOS: 25, 26, and 27) (ClustalW algorithm, MEGALIGN™, Lasergene, Wis.).

FIG. 19 Immunohistochemistry showing the distribution of GMCSF-receptor alpha (a-d) and GMCSF (e-g) in different brain regions in the mouse (paraffin sections, 2 µm). a: In the cerebellum, Purkinje cells are labeled (arrow). b-d: localization of GMCSF-R alpha in the hippocampus. Note the presence of the receptor in the hilus of the dentate gyrus (b, arrow). The antibody predominantly stains neurons in the CA3 area (c) with a sharp boundary between the CA3 and CA2 region (c, arrow). GMCSF-R alpha is distributed over the soma (CA3), as well as processes of neurons (CA2). GMCSF-receptor was also detected in the entorhinal cortex (d). GMCSF shows similar distribution in comparison with GMCSF-receptor alpha. Note that the GMCSF antibody stains as well Purkinje cells (e, arrow), neurons in the CA3 area (f) with sharp boundary between CA3 and CA2 region (f, arrow), and neurons in the entorhinal cortex (g). FIG. 19*h-m*: Shown here is the surprising colocalization of the GMCSF receptor and its ligand in neurons. h, localization of the GMCSF receptor (antibody sc690, Santa Cruz) in neurons in hippocampal subfield CA3, arrow points to the sharp expression boundary to the adjacent CA2 region. i, the GMCSF ligand (antibody sc13101) shows the same subfield-specific expression, the arrow points to one neuron in the CA3 region. j, expression of the GMCSF receptor in the hilus and subgranular zone of the dentate gyrus. An arrow points to a neuron in the subgranular zone. k, expression of the GMCSF ligand in that region. Here, the ligand shows a slightly different expression compared to its receptor. There is clear expression in the CA3 region (arrow), but less in the dentate gyrus region. l,m: expression of the GMCSF receptor (l) and ligand (m) in the large motoneurons of the spinal cord. This surprising expression is a clear indication for the therapeutic applicability of the GMCSF system for motoneuron diseases, especially amyotrophic lateral sclerosis (ALS).

FIG. 22 demonstrates the presence of the GMCSF-receptor alpha on adult neuronal stem cells (nsc) by immunocytochemistry. Shown is one neurosphere that is stained with DAPI (A, stains all cell nuclei), and an antibody specific for the GMCSF receptor (B) (magnification 10×).

DETAILED DESCRIPTION OF THE INVENTION

GCSF

Figure 1:
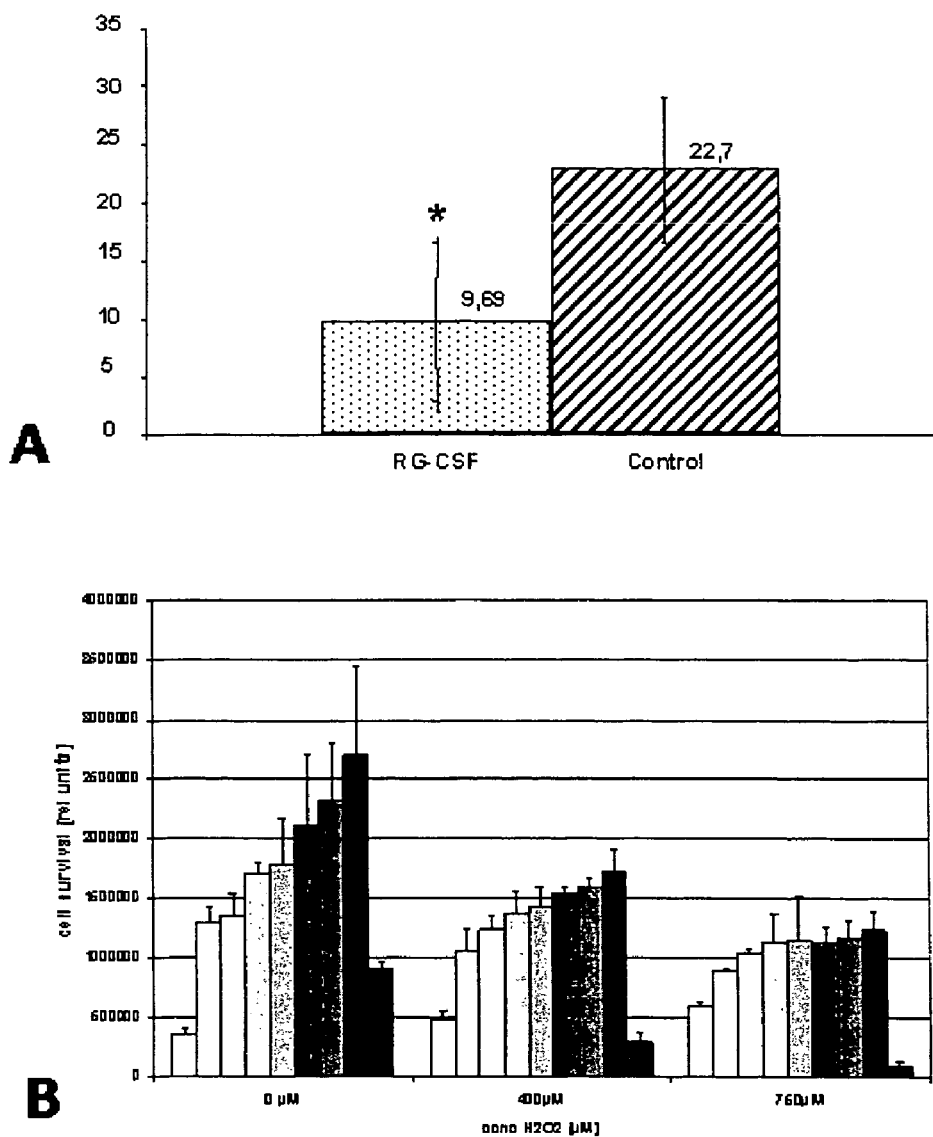
FIG. 1 demonstrates effective neuroprotection by GCSF in vivo and in vitro. A, the extent of neuroprotection of GCSF after focal cerebral ischemia (filament model; middle cerebral artery occlusion, MCAO) as measured by TTC-staining. The values of the y-axis relate to percent of infarction of the total hemisphere (data are mean±SD; T-test; $p<0.05$). B, cell survival assay in NGF-treated PC12 cells under increasing oxidative stress by $H_2O_2$ (0 uM, 400 uM, 750 uM). GCSF treatment produces dramatic increases in cell survival. In comparison, cell survival after treatment of the cells with Erythropoetin (EPO), a known neuroprotective substance, is given. Y-axis: Relative (Rel.) cell survival (light units of luciferase activity).

Granulocyte-colony stimulating factor (GCSF) is a well known growth factor. The GCSF that can be employed in the inventive methods described herein are those full length coding sequences, protein sequences, and the various functional variants, muteins, and mimetics that are known and available. In the discussion that follows these are referred to as GCSF derivatives.

The structure of both the coding DNA and protein are known as well as methods for recombinantly producing mammalian pluripotent granulocyte colony-stimulating factor (WO 87/01132; U.S. Pat. No. 4,810,643).

In one embodiment, the proteins that are at least 70%, preferably at least 80%, more preferably at least 90% identical to the full-length human GCSF amino acid sequences described herein can be employed in the present invention. In another embodiment, the GCSF that can be used are those that are encoded by polynucleotide sequence with at least 70%, preferably 80%, more preferably at least 90% identity to the wildtype full-length human GCSF coding sequence, these polynucleotides will hybridize under stringent conditions to the coding polynucleotide sequence of the wild-type full length human GCSF. The terms "stringent conditions" or "stringent hybridization conditions" includes reference to conditions under which a polynucleotide will hybridize to its target sequence, to a detectably greater degree than other sequences (e.g., at least 2-fold over background). Stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides), for example, high stringency conditions include hybridization in 50% formamide, 1 M NaCl, 1% SDS at 37° C., and a wash in 0.1×SSC at 60 to 65° C. (see Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995)). Amino acid and polynucleotide identity, homology and/or similarity can be determined using the ClustalW algorithm, MEGALIGN™, Lasergene, Wis.)

Examples of the various GCSF functional variants, muteins, and mimetics include functional fragments and variants (e.g., structurally and biologically similar to the wild-type protein and having at least one biologically equivalent domain), chemical derivatives of GCSF (e.g., containing additional chemical moieties, such as polyethyleneglycol and polyethyleneglycol derivatives thereof, and/or glycosylated forms such as Lenogastrim™), and peptidomimetics of GCSF (e.g., a low molecular weight compound that mimics a peptide in structure and/or function (see, e.g., Abell, *Advances in Amino Acid Mimetics and Peptidomimetics*, London: JAI Press (1997); Gante, *Peptidmimetica—massgeschneiderte Enzyminhibitoren Angew. Chem.* 106: 1780-1802 (1994); and Olson et al., *J. Med. Chem.* 36: 3039-3049 (1993)).

Additional examples of GCSF derivatives include a fusion protein of albumin and GCSF (Albugranin™), or other fusion modifications such as those disclosed in U.S. Pat. No. 6,261,250); PEG-GCSF conjugates; those described in WO 00/44785 and Viens et al., *J. of Clin. Oncology*, V1, Nr. 1, 2002: 24-36; norleucine analogues of GCSF, those described in U.S. Pat. No. 5,599,690; GCSF mimetics, such as those described in WO 99/61445, WO 99/61446, and Tian et al., *Science*, Vol. 281, 1998:257-259; GCSF muteins, where single or multiple amino acids have been modified, deleted or inserted, as described in U.S. Pat. Nos. 5,214,132 and 5,218,092; those GCSF derivatives described in U.S. Pat. No. 6,261,550 and U.S. Pat. No. 4,810,643; and chimeric molecules, which contain the full sequence or a portion of GCSF in combination with other sequence fragments, e.g. Leridistim—see, for example, Streeter, et al. (2001) *Exp. Hematol.*, 29, 41-50, Monahan, et al. (2001) *Exp. Hematol.*, 29, 416-24, Hood, et al. (2001) *Biochemistry*, 40, 13598-606, Farese et al. (2001) *Stem Cells*, 19, 514-21, Farese, et al. (2001) *Stem Cells*, 19, 522-33, MacVittie, et al. (2000) *Blood*, 95, 837-45. Additionally, the GCSF derivatives include those with the cysteines at positions 17, 36, 42, 64, and 74 (of the 174 amino acid species (SEQ ID NO:37) or of those having 175 amino acids, the additional amino acid being an N-terminal methionine (SEQ ID NO:38)) substituted with another amino acid, (such as serine) as described in U.S. Pat. No. 6,004,548, GCSF with an alanine in the first (N-terminal) position; the modification of at least one amino group in a polypeptide having GCSF activity as described in EP 0 335 423; GCSF derivatives having an amino acid substituted or deleted in the N-terminal region of the protein as described in EP 0 272 703; derivatives of naturally occurring GCSF having at least one of the biological properties of naturally occurring GCSF and a solution stability of at least 35% at 5 mg/ml in which the derivative has at least $Cys^{17}$ of the native sequence replaced by a $Ser^{17}$ residue and $Asp^{27}$ of the native sequence replaced by a $Ser^{27}$ residue as described in EP 0 459 630; a modified DNA sequence encoding GCSF where the N-terminus is modified for enhanced expression of protein in recombinant host cells, without changing the amino acid sequence of the protein as described in EP 0 459 630; a GCSF which is modified by inactivating at least one yeast KEX2 protease processing site for increased yield in recombinant production using yeast as described in EP 0 243 153; lysine altered proteins as described in U.S. Pat. No. 4,904,584; cysteine altered variants of proteins as described in WO/9012874 (U.S. Pat. No. 5,166,322); the addition of amino acids to either terminus of a GCSF molecule for the purpose of aiding in the folding of the molecule after prokaryotic expression as described in AU-A-10948/92; substituting the sequence Leu-Gly-His-Ser-Leu-Gly-Ile (SEQ ID NO:11) at position 50-56 of GCSF with 174 amino acids (SEQ ID NO:37), and position 53 to 59 of the GCSF with 177 amino acids (SEQ ID NO:39), or/and at least one of the four histadine residues at positions 43, 79, 156 and 170 of the mature GCSF with 174 amino acids (SEQ ID NO:37) or at positions 46, 82, 159, or 173 of the mature GCSF with 177 amino acids (SEQ ID NO:39) as described in AU-A-76380/91; and a synthetic GCSF-encoding nucleic acid sequence incorporating restriction sites to facilitate the cassette mutagenesis of selected regions and flanking restriction sites to facilitate the incorporation of the gene into a desired expression system as described in GB 2 213 821.

The various functional derivatives, variants, muteins and/or mimetics of GCSF preferably retain at least 20%, preferably 50%, more preferably at least 75% and/or most preferably at least 90% of the biological activity of wild-type mammalian GCSF activity—the amount of biological activity include 25%, 30%, 35%, 40%, 45%, 55%, 60%, 65%, 70%, 75%, 80%, 85%, 95%; and all values and subranges there between. Furthermore, the functional derivatives, variants, muteins and/or mimetics of GCSF can also have 100% or more of the biological activity relative to wild-type mammalian GCSF activity—the amount of biological activity including at least 105%, at least 110%, at least 125%, at least 150%, and at least 200%.

To measure the biological activity of GCSF, several known assays can be employed singularly or in combination. One example of determining GCSF function is illustrated in Example 1. Other methods for determining GCSF function are known and include a colony formation assay employing murine bone marrow cells; stimulation of proliferation of bone marrow cells induced by G-CSF; specific bioassays with cells lines that depend on G-CSF for growth or that respond to GCSF (e.g., AML-193; 32D; BaF3; GNFS-60; HL-60, M1; NFS-60; OCI/AML1a; and WEHI-3B). These and other assays are described in Braman et al. *Am. J. Hematology* 39: 194-201 (1992); Clogston C L et al *Anal Biochem* 202: 375-83 (1992); Hattori K et al *Blood* 75: 1228-33 (1990); Kuwabara T et al *Journal of Pharmacobiodyn* 15: 121-9 (1992); Motojima H et al *Journal of Immunological Methods* 118: 187-92 (1989); Sallerfors B and Olofsson *European Journal of Haematology* 49: 199-207 (1992); Shorter S C et al *Immunology* 75: 468-74 (1992); Tanaka H and Kaneko *Journal of Pharmacobiodyn.* 15: 359-66 (1992); Tie F et al *Journal of Immunological Methods* 149: 115-20 (1992); Watanabe M et al *Anal. Biochem.* 195: 38-44 (1991).

In one embodiment, the GCSF is modified or formulated, or is present as a GCSF mimetic that increases its ability to cross the blood-brain barrier, or shift its distribution coefficient towards brain tissue. An example of such a modification is the addition of PTD or TAT sequences (Cao et al. (2002) *J. Neurosci.* 22:5423-5431; Mi et al. (2000) *Mol. Ther.* 2:339-347; Morris et al. (2001) *Nat Biotechnol* 19:1173-1176; Park et al. (2002) *J Gen Virol* 83:1173-1181). These sequences can also be used in mutated forms, and added with additional amino acids at the amino- or carboxy-terminus of proteins. Also, adding bradykinin, or analogous substances to an intravenous application of any GCSF preparation will support its delivery to the brain, or spinal cord (Emerich et al. (2001) *Clin Pharmacokinet* 40:105-123; Siegal et al (2002) *Clin Pharmacokinet* 41:171-186).

GM-CSF

Granulocyte-macrophage colony stimulating factor (GMCSF) is a well known growth factor. The GMCSF that can be employed in the inventive methods described herein are those full length coding sequences, protein sequences, and the various functional variants, chimeric proteins, muteins, and mimetics that are known and available. The structure of both the coding DNA and protein are known as well as methods for recombinantly producing mammalian pluripotent granulocyte macrophage colony-stimulating factor (U.S. Pat. No. 5,641,663). The GMCSF receptor is also known and is described, for example, in U.S. Pat. No. 5,629,283.

In one embodiment, the proteins that are at least 70%, preferably at least 80%, more preferably at least 90% identical to the full-length human GMCSF amino acid sequences can be employed in the present invention. In another embodiment, the GMCSF that can be used are those that are encoded by polynucleotide sequence with at least 70%, preferably 80%, more preferably at least 90% identical to the wildtype full-length human GMCSF coding sequence, these polynucleotides will hybridize under stringent conditions to the coding polynucleotide sequence of the wild-type full length human GMCSF. The terms "stringent conditions" or "stringent hybridization conditions" includes reference to conditions under which a polynucleotide will hybridize to its target sequence, to a detectably greater degree than other sequences (e.g., at least 2-fold over background). Stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides), for example, high stringency conditions include hybridization in 50% formamide, 1 M NaCl, 1% SDS at 37° C., and a wash in 0.1×SSC at 60 to 65° C. (see Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995)). Amino acid and polynucleotide identity, homology and/or similarity can be determined using the ClustalW algorithm, MEGALIGN™, Lasergene, Wis.)

The various functional derivatives, variants, muteins and/or mimetics of GMCSF preferably retain at least 20%, preferably 50%, more preferably at least 75% and/or most preferably at least 90% of the biological activity of wild-type mammalian GMCSF activity—the amount of biological activity include 25%, 30%, 35%, 40%, 45%, 55%, 60%, 65%, 70%, 75%, 80%, 85%, 95%; and all values and subranges there between. Furthermore, the functional derivatives, variants, muteins and/or mimetics of GMCSF can also have 100% or more of the biological activity relative to wild-type mammalian GMCSF activity—the amount of biological activity including at least 105%, at least 110%, at least 125%, at least 150%, and at least 200%.

For practicing the present invention derivatives of GMCSF, more preferably GMCSF-mimetics, that retain their potential to protect neurons and that also have diminished action on leukocytes, thereby reducing potential adverse effects, are preferred. Derivatives of GMCSF, preferably GMCSF-mimetics, can be tested in an in vitro neuroprotective assay, such as described in Example 17. Substances demonstrating a positive neuroprotective effect in this assay can be further tested for their immune-modulatory activity.

To measure the biological activity of GMCSF, several known assays can be employed singularly or in combination. Those GMCSF functions include its known immunmodulatory functions and to one or more functions relating to its role in neuroprotection. Other methods for determining GMCSF function include, for example, in a colony formation assay by the development of colonies containing macrophages, neutrophils, eosinophils, and megakaryocytes; in specific Bioassays with cell lines that depend in their growth on the presence of GM-CSF or that respond to this factor (e.g., cell lines:

AML-193; B6SUt-A BAC1.2F5; BCL1; Da; FDCP1; GF-D8; GM/SO; IC-2; M07E; NFS-60; PT-18 TALL-103; TF-1; UT-7). These and other assays are described in Cebon J et al *Blood* 72: 1340-7 (1988); Katzen N A et al *European Cytokine Network* 3: 365-72 (1992); Lewis C E et al *Journal of Immunological Methods* 127: 51-9 (1990); Mortensen B T et al *Experimental Hematology* 21: 1366-70 (1993); Oez S et al *Experimental Hematology* 18: 1108-11 (1990); Roncaroli F et al *Journal of Immunological Methods* 158: 191-6 (1993); Sallerfors B and Olofsson *European Journal of Haematology* 49: 199-207 (1992); Zenke G et al *Journal of Immunoassay* 12: 185-206 (1991).

Also preferred are modifications or formulations of GMCSF, or mimetic substances that increase its ability to cross the blood-brain barrier, or shift its distribution coefficient towards brain tissue. An example for such a modification is the addition of Protein transduction domain (PTD) or TAT sequences (Cao G, et al (2002) *J. Neurosci.* 22:5423-5431; Mi Z et al (2000) *Mol. Ther.* 2:339-347; Morris et al (2001) *Nat Biotechnol* 19:1173-1176; Park et al (2002) *J Gen Virol* 83:1173-1181). These sequences can also be used in mutated forms, and added with additional amino acids at the amino- or carboxyterminus of proteins. Also, adding bradykinin, or analogous substances to an intravenous application of any GMCSF preparation will support its delivery to the brain, or spinal cord (Emerich et al (2001) *Clin Pharmacokinet* 40:105-123; Siegal et al (2002) *Clin Pharmacokinet* 41:171-186). Examples for different suitable forms and derivatives are sargramostim (Leukine®, Prokine®), Leucotropin® or molgramostim (Leucomax®).

GMCSFR mRNA has been detected in isolated microglia, astrocytes, oligodendrocytes and neurons (Sawada, et al. (1993), *Neurosci Lett,* 160, 131-4); Baldwin, et al. (1993), *Blood,* 82, 3279-82.). It has been shown that GMCSF stimulates the proliferation of astrocytes (Guillemin, et al. (1996), *Glia,* 16, 71-80). GMCSF also induces the release of interleukin 6 from microglia (Suzumura, et al. (1996), *Brain Res,* 713, 192-8). Recently, a publication showed that interleukin 1 increased GMCSF protein production in the neuronal cell line NT2 (Dame, et al. (2002), *Eur Cytokine Netw,* 13, 128-33). The presence of GMCSFR in the brain was shown on material from a human fetus on a systematic search for GMCSF receptor expression in the fetus (Dame, et al. (1999), *Pediatr Res,* 46, 358-66). Dame et al. conclude from their findings, that GMCSF may have a role in neural development in the fetus, and a role in immunosurveillance in the adult brain. Importantly, they do not mention any possible disease relevance, especially no involvement in neuroprotection. GMCSF augments choline acetyltransferase activity in vitro (SN6.10.2.2 cell line and cultured mouse septal neurons) and in vivo increases survival of lesioned rat cholinergic septal neurons after fimbria-fomix transections (Kamegai, et al. (1990), *Brain Res,* 532, 323-5.) (Konishi, et al. (1993), *Brain Res,* 609, 29-35). Importantly, this finding only pertains to a certain subtype of neurons, and has not been generalized by the authors to other neuronal or neural cell types. They have not derived a general neuroprotective property of GMCSF from these data, nor have they mentioned any possible therapeutic applicability. GMCSF is upregulated in astrocytes upon addition of advanced glycosylation end products (AGEs) (Li et al. (1998), *Mol Med,* 4, 46-60). GMCSF has been shown to promote microglia proliferation in vitro (Lee, et al. (1994), *Glia,* 12, 309-18). Recently, it has been found that GMCSF level were elevated in the cerebrospinal fluid (csf) of patients with Alzheimer's disease (Tarkowski et al. (2001), *Acta Neurol Scand,* 103, 166-74). GMCSF has also been studied in the CSF of stroke patients (Tarkowski, et al. (1999), Stroke, 30, 321-7.). In the latter study, the level of the FAS ligand, a proapoptotic protein, correlates positively with GMCSF levels in the cerebrospinal fluid of stroke patients at day 21-26 and later than 3 months. However, there is no conclusion drawn to any therapeutic usefulness of this finding in stroke patients, and no mentioning of any possible neuroprotective role of GMCSF. A release of GMCSF after stroke per se can have many reasons, and does not allow any functional prediction to be made. GMCSF crosses the blood-brain-barrier (McLay, et al. (1997), *Brain,* 120, 2083-91.). This study has not been performed with the purpose of showing any therapeutic applicability of GMCSF to neurological diseases, and there is no contextual mentioning of a possible usefulness of GMCSF in neurodegenerative diseases or stroke.

In summary, the above mentioned references in the literature provide evidence for presence of the GMCSF receptor and ligand in the nervous system, but do not show any general neuroprotective property of GMCSF. These studies certainly do not imply use of GMCSF for the treatment of neurodegenerative and ischemic disorders such as stroke.

Other Hematopoeitic Growth Factors

In other embodiments of the present invention combinations of GCSF and/or GMCSF preparations that support its therapeutic actions, preferably its neuroprotective action can be used. The effect exerted by these combinations can be cumulative or superadditive/synergistic. In a one embodiment, various GCSF and/or GMCSF derivatives are used in combination with each other. Likewise, GCSF and/or GMCSF can be used in combination with one or more additional hematopoietic growth factors such as Erythropoietin, and derivatives thereof, which has recently been shown to mediate strong neuroprotective properties (e.g., Brines et al (2000) *Proc Natl Acad Sci USA* 97:10526-10531; Cerami et al (2002) *Nephrol Dial Transplant* 17:8-12; Siren A L, Ehrenreich H (2001) *Eur Arch Psychiatry Clin Neurosci* 251:179-184.). In addition, GMCSF and/or GCSF can be used in combination with, for example, various colony stimulating factors (such as M-CSF), SCF (stem cell factor), SCPF (stem cell proliferation factor), various Interleukins (IL1, IL3, IL4, IL5, IL6, IL11, IL12), LIF, TGF-β, MIP-1-α, TNF-α, and also many other low molecular weight factors.

In another embodiment, the various hematopoietic growth factors with the exception of Erythropoetin may be used alone in the absence of GMCSF and/or GCSF. In another embodiment, for example, in the context of stroke, GCSF and/or GMCSF can be combined with substances that have thrombolytic activities, e.g., tissue-plasminogen activator (TPA), streptokinase, urokinase, and/or Ancrod. GCSF and/or GMCSF can also be combined with either acetylsalicylic acid (Aspirin) or Heparin; with Melatonin; and/or substances that interfere with apoptotic signaling (e.g. inhibitors of caspases). Also, especially in, but not limited to, the treatment of amyotrophic lateral sclerosis (ALS) combinations of GCSF and/or GMCSF with Riluzole (Rilutek®), vitamins such as vitamin E, Q10, or antioxidative substances are possible. For treating Parkinson's disease, combinations of GCSF and/or GMCSF with known drugs used in the treatment of Parkinson's disease, such as Trihexyphenidyl, Selegiline, L-DOPA, Pergolide, and others may be employed.

Neurological Conditions

Neurological conditions that are to be treated according to the present invention can be generally classified into three classes: those disease with ischemic or hypoxic mechanisms; neurodegenerative diseases (see Adams et al, Principles of Neurology, 1997, 6th Ed., New York, pp 1048 ff); and neurological and psychiatric diseases associated with neural cell death. Other neurological conditions that can be treated according to the present invention also include enhancing cognitive ability and the treatment of brain tumors, such as glioblastomas, astrocytomas, meningiomas, and neurinomas.

Diseases with ischemic or hypoxic mechanisms can be further subclassified into general diseases and cerebral ischemia. Examples of such general diseases involving ischemic or hypoxic mechanisms include myocardial infarction, cardiac insufficiency, cardiac failure, congestive heart failure, myocarditis, pericarditis, perimyocarditis, coronary heart disease (stenosis of coronary arteries), angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, and pulmonary edema. Examples of cerebral ischemia disease include stroke (as well as hemorrhagic stroke), cerebral microangiopathy (small vessel disease), intrapartal cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, and diabetic retinopathy.

Examples of neurodegenerative diseases include amyotrophic lateral sclerosis (ALS), Parkinson's disease, Huntington's disease, Wilson's disease, multi-system atrophy, Alzheimer's disease, Pick's disease, Lewy-body disease, Hallervorden-Spatz disease, torsion dystonia, hereditary sensorimotor neuropathies (HMSN), Gerstmann-Straussler-Schanker disease, Creutzfeld-Jakob-disease, Machado-Joseph disease, Friedreich ataxia, Non-Friedreich ataxias, Gilles de la Tourette syndrome, familial tremors, olivopontocerebellar degenerations, paraneoplastic cerebral syndromes, hereditary spastic paraplegias, hereditary optic neuropathy (Leber), retinitis pigmentosa, Stargardt disease, and Kearns-Sayre syndrome.

Examples of neurological and psychiatric diseases associated with neural cell death include septic shock, intracerebral bleeding, subarachnoidal hemorrhage, multiinfarct dementia, inflammatory diseases (such as vasculitis, multiple sclerosis, and Guillain-Barre-syndrome), neurotrauma (such as spinal cord trauma, and brain trauma), peripheral neuropathies, polyneuropathies, epilepsies, schizophrenia, metabolic encephalopathies, and infections of the central nervous system (viral, bacterial, fungal).

By "treating" is meant the slowing, interrupting, arresting or stopping of the progression of the disease or condition and does not necessarily require the complete elimination of all disease symptoms and signs. "Preventing" is intended to include the prophylaxis of the neurological disease, wherein "prophylaxis" is understood to be any degree of inhibition of the time of onset or severity of signs or symptoms of the disease or condition, including, but not limited to, the complete prevention of the disease or condition.

Since strong expression of the GCSF receptor, and the GMCSF receptor on the large motor neurons in the spinal cord was found (see FIG. 4*i-l*), and GCSF is effective in focal cerebral ischemia (see FIG. 1), where the same basic pathogenetic mechanisms are operative like in ALS and other neurodegenerative diseases, such as glutamate involvement, oxidative stress, and programmed cell death GCSF is especially suited for long-term therapy in a chronic condition such as ALS, since it is well-tolerated in humans when given chronically (Ozer et al. (2000), *J. Clin. Oncol.*, 18, 3558-85). Accordingly, in one embodiment of the present invention, the hematopoeitic growth factors such as GCSF and GMCSF alone, in combination with each other, and/or in combination with one or more additional factors can be used to treat ALS.

The pathophysiology associated with Parkinson's disease, such as the involvement of oxidative stress and apoptosis also places Parkinson's disease amongst the other neurodegenerative disorders and stroke. GCSF is strongly neuroprotective in $H_2O_2$-invoked cell death in the cell line PC12 (FIG. 1*b*). $PCl_2$ cells display features of dopaminergic cells, for example presence of a functional dopamine transporter (Maruyama, et al. (2001), *Arch Toxicol*, 75, 209-13), and are used as in vitro models for important aspects of Parkinson's disease, for example toxicity by the MPTP metabolite MPP+ (Bai, et al. (2002), *Neurosci Lett*, 321, 81-4). $H_2O_2$ is a noxious stimulus for PC12 cells that clearly models some aspects of Parkinson's disease in PC12 cells. For example, $H_2O_2$ is one of the intermediates of MPTP-evoked cellular events (Fabre et al 1999 *J Physiol Biochem* 55(4):325-31). There is a remarkable overlap in the cascade of cellular events and signaling mechanisms involved in MPTP- and $H_2O_2$-mediated cell death in dopaminergic neurons (Chun, H S, et al., *J Neuro chem* 2001 February; 76(4):1010-21; Lai et al., *Biochem Pharmacol* 1993 Feb. 24; 45(4):927-33). $H_2O_2$ acts by producing reactive oxygen species (ROS) that lead to oxidative stress and apoptosis. Damage by oxygen radicals is one of the main pathophysiological events in Parkinson's disease (Bonnet and Houeto (1999), *Biomed Pharmacother*, 53, 117-21, Beal (2001), *Nat Rev Neurosci*, 2, 325-34), and antioxidant therapy is effective in patients (Beal (2002), *Free Radic Res*, 36, 455-60, Shults, et al. (2002), *Arch Neurol*, 59, 1541-50). Therefore, efficacy of GCSF in $H_2O_2$ evoked cell death in PC12 cells, a model for the important pathophysiological mechanisms of oxidative stress and apoptosis predicts efficacy in Parkinson's disease (PD): Surprisingly, the expression of the GCSF receptor in the area affected by Parkinson's disease, the substantia nigra (SN), in particular the substantia nigra pars compacta (SNC) (see FIG. 4*m-o*) was demonstrated. Efficacy in a cellular model, in vivo localization of receptors, and overlap of pathophysiological mechanisms with cerebral ischemia (oxygen radicals/apoptosis) provides compelling evidence that GCSF and/or other growth factors, for example, GMCSF, can be used to treat Parkinson's disease. Efficacy testing in rodent models can be performed as exemplified in Example 5. Accordingly, in another embodiment of the present invention, the hematopoeitic growth factors such as GCSF and GMCSF alone, in combination with each other, and/or in combination with one or more additional factors can be used to treat Parkinson's disease.

The similar neurochemical milieu around the ischemic core and the site of trauma, along with similarly altered gene transcription suggest that similar neuroprotective strategies, aimed at interference with harmful mechanisms should be effective in cerebral ischemia and traumatic brain injury. The goal of such therapy in both types of injuries is to minimize activating toxic pathways and to enhance activity of endogenous neuroprotective mechanisms as the balance between these pathways will eventually determine the fate of the tissue at risk. Indeed, most neuroprotectants found to be effective in models of experimental stroke are also effective in models of experimental traumatic brain injury (TBI).

In light of the common pathological and protective processes active in cerebral ischemia and traumatic brain injury, as well as, a common response to neuroprotective strategies indicates that GCSF therapy will be effective in traumatic brain injury. There has been one study that examined GCSF under conditions of traumatic brain injury (Heard, et al. (1998), *Crit. Care Med.*, 26, 748-54). However this study did not aim at any neuroprotective effects of GCSF (filgrastim), but merely reducing infection parameters (primary endpoints of the study: increase in absolute neutrophil count, safety of filgrastim, and frequency of nosocomial infections (pneumonia, bacteremia, and urinary tract infection)). There was no improvement of mortality in that study. In the context of clinical safety, this study demonstrated that GCSF administration is safe for TBI, confirming the safe practicability of GCSF treatment for neuroprotection according to the present invention. Accordingly, in another embodiment of the present invention, the hematopoeitic growth factors, for example GCSF and GMCSF, alone, in combination with each other, and/or in combination with one or more additional factors can be used to treat cerebral ischemia and traumatic brain injury, for example, by providing a prophylactic way of protecting neuronal cells in those patients with the injury.

Since the basic pathophysiological mechanisms operative in cerebral ischemia due to cardiac failure and resuscitation are comparable to those occurring under cerebral ischemia due to occlusion of blood vessels (see Example 1), GCSF therapy will also be effective under conditions of cardiac problems for neuroprotection. Therefore, in another embodiment of the present invention, the hematopoeitic growth factors, for example, GCSF and GMCSF, alone, in combination with each other, and/or in combination with one or more additional factors can be used to treat ischemia as a result of cardiac problems/diseases and/or provide prophylactic neuroprotective therapy. Therapy can be started as soon as emergency resuscitation is started. Alternatively, in patients belonging to known risk groups for cardiac problems (prior myocardial infarction, high blood cholesterol levels, high blood pressure, diabetes, smoking), a prophylactic continued therapy with the hematopoietic growth factors, for example, GCSF, can also be performed, e.g. using a slow release form of the factor(s).

Likewise, these above considerations apply to the large group of patients that undergo surgery with subsequent cerebral ischemia. In particular, cardiac surgery (Hogue et al. (1999), *Circulation*, 100, 642-7), and surgery on the large blood vessels supplying the brain (e.g. carotid endarterectomies) have a high risk of neurological complications associated with them. An objective, retrospective review of 358 carotid endarterectomies performed in the neurosurgical teaching units of the University of Toronto in the year 1982 demonstrated a perioperative stroke rate of 3.9% and a death rate of 1.5%. Most (82%) surgical neurological complications occurred after the immediate post-operative period (24 hours). This high incidence of delayed stroke suggests that most perioperative strokes are embolic rather than hemodynamic. A 5-6% combined morbidity and mortality should be expected in carotid endarterectomy (Group (1986), *Stroke*, 17, 848-52). These and other data demonstrate a clear need for a prophylactic neuroprotective therapy in these procedures. Therefore, in another embodiment of the present invention, the hematopoeitic growth factors, for example, GCSF and GMCSF, alone, in combination with each other, and/or in combination with one or more additional factors can be used to treat ischemia as a result of surgically induced cerebral ischemia and/or provide prophylactic neuroprotective therapy. In one embodiment, the treatment is started in the at risk patients prior to a major surgical procedure.

In another embodiment of the present invention, the hematopoeitic growth factors, for example, such as GCSF and GMCSF, alone, in combination with each other, and/or in combination with one or more additional factors can be used to treat multiple sclerosis (MS) and/or provide prophylactic neuroprotective therapy in multiple sclerosis patients. This method is based on the presence of the GCSF receptor on oligodendrocytes, supporting a direct efficacy of GCSF on the primary target cells of the MS. In addition, the GCSF receptor is present on nerve cells and their processes, which are compromised at later stages of the disease, and could correlate with lasting disabilities (Cid et al. (2002), *J Neurol Sci*, 193, 103-9). Furthermore, pathophysiological mechanisms in multiple sclerosis overlap with important mechanisms in cerebral ischemia, e.g. the involvement of nitric oxide (Smith, et al. (2001), *Ann Neurol*, 49, 470-6), and involvement of glutamate excitotoxicity (Pitt et al. (2000), *Nat Med*, 6, 67-70). In light of this information, the hematopoeitic growth factors such as GCSF and GMCSF are a novel treatment option for multiple sclerosis and inflammatory brain disorders.

Another embodiment of the present invention relates to the neuroprotective treatment of schizophrenia. There has been surprising evidence in the recent years of progressive grey matter loss in schizophrenics. This evidence has been primarily provided by novel magnetic resonance imaging techniques. Although neurodegenerative processes in schizophrenia are not understood at the molecular level, neuroprotective treatment in schizophrenia with GCSF and/or GMCSF is a novel approach to this disease.

To test the efficacy of hematopoietic growth factors, such as GCSF, in the protection of primary neurons can be prepared as follows. 10-12 rat cortices can be prepared from embryos of the stage E18 (embryonic day 18). Tissue can be dissociated using trypsin [10 mg/ml]/EDTA/DNase [5 mg/ml] (Roche diagnostics, Mannheim, Germany) in HBSS (Hanks balanced salt solution, BioWithakker). The digest can be stopped using 4 parts medium (neurobasalmedium+1 ml 50×B-27 supplement (Invitrogen)+0.5 mM L-glutamine+25 µM glutamate) and can be centrifuged at room temperature for 5 min at 800 g. The pellet can be dissolved in 5 ml medium and cell number determined by counting (Neubauer slide). The cells can be plated at a density of 250 000 cells per well of a 24-well-plate on cover slips which can be coated with poly-L-lysine. These neurons can then be treated with combinations of a protective stimulus (GCSF) and a noxious stimulus (glutamate, 100 µM). GCSF is applied 30 min prior to treatment of cultures with glutamate. Control groups are treated with either no GCSF (just saline) or no glutamate. After 24 h, neuronal cell death can be determined using the LDH assay (Roche Diagnostics, Mannheim, Germany), following the manufacturers recommendations. Alternatively, other noxious stimuli known for inducing cell death can be used, e.g., NMDA and glycine, 3-nitropropionic acid (3-NPA), $H_2O_2$, staurosporine, hypoxia/glucose deprivation, potassium withdrawal, MPP+, Interleukin-1beta, TNFalpha, FAS ligand or others known to be harmful to cells and neurons. Different assays can also be used for assessing cell death or relative cell survival, e.g. the cell-death ELISA (Roche Diagnostics), Annexin/propidium iodide staining followed by a laser-scanning cytometry analysis (Kamentsky (2001), *Methods Cell Biol*, 63, 51-87), Compucyte, Cambridge, Mass.), counting of cell nuclei with apoptotic features following DAPI or HOECHST33342 staining (condensation, fragmentation), counting of cells positive for activated caspase 3 after immunostaining with a cleavage-specific antibody (e.g., Promega caspase 3 antibody), or an assay for caspase3 activity in cell lysates (e.g., ApoOne Assay, Promega; Western blots, Elisas), or any other assay suited for measuring cell survival or apoptotic features. Alternatively, other cells can be used, for example differentiated PC12 cells, HN33 cells, SHSY5 cells, primary hippocampal neurons, primary motor neurons, primary sensory ganglia cells, primary mesencephalic cultures, neuronal stem cells, differentiated ES cells, or other neuron-like cells known in the art, or cells exhibiting one or more neuronal phenotypes. Times and concentrations exemplified here can also be varied, for example, GCSF can be applied concomitantly with a stimulus, or before or after the stimulus. Varying concentrations of GCSF can also be used, e.g. 0.1-100 μg/ml. In principal, this assay can also be adapted for the use in brain slice cultures.

To test the effectiveness of hematopoietic growth factors, such as GCSF, in a model of brain trauma (controlled cortical impact) the following can be performed. Experimental protocols can be approved by the local ethics committee. Twenty male Wistar rats (Charles River, Germany) weighing 280 to 320 g can be randomly assigned to the following groups: A (Control group, n=10, traumatic brain injury (TBI), treatment with 2 ml saline 0.9% for 90 min beginning 30 min TBI); B (GCSF group, n=10, ischemia for 90 min, treatment with 60 μg/kg body weight of recombinant G-CSF, Neupogen®, Amgen, Europe B.V., Netherlands, soluted in 2 ml saline 0.9% for 90 min beginning 30 min TBI); C (sham-operated GCSF-treated control group, n=10, sham operation, treatment with 60 μg/kg body weight of recombinant G-CSF, Neupogen®, Amgen, Europe B.V., Netherlands, soluted in 2 ml saline 0.9% for 90 min beginning 30 min after TBI).

Animals can be anesthetized with an intraperitoneal injection of 100 mg/kg body weight ketaminehydrochloride (WDT, Garbsen, Germany). Anesthesia can be maintained with 50 mg/kg body weight, if necessary. A PE-50 polyethylene tube can be inserted into the right femoral artery for continuous monitoring of mean arterial blood pressure, blood gases, hematocrit, leukocyte count and blood glucose levels. The right femoral vein can be cannulated by a PE-50 tube for treatment infusion. During the experiment, rectal temperature can be monitored and maintained at 37° C. by a thermostatically controlled heating pad (Föhr Medical Instruments, Germany).

For TBI the skin then can be cut around the probe and the skull exposed and cleaned. TBI can be inflicted using a weight-drop device with indirect impact, modified for compatibility with microdialysis (a weight of 150 g dropped from 40 cm onto a PVC cylinder with a Teflon point of 2.0 mm diameter). Sham operated controls can be identically prepared to rats that received TBI, without the trauma.

In all animals outcome can be measured by mortality, as well as, Neurological Severity Scores (NSS), performed daily for 1 week after traumatic brain injury by an investigator blinded to the experimental groups. Neurological function can be graded on a scale of 0 to 16 (normal score, 0; maximal deficit score, 16). NSS is a composite of motor, sensory, and reflex tests and includes the beam balance test. In the severity scores of injury, 1 score point is awarded for the inability to perform the test or for the lack of a tested reflex; thus, the higher score, the more severe is the injury.

One week after TBI, the rats can be anesthetized with ketamine 150 mg/kg body weight and decapitated. The brains can be removed, and fixed with 4% paraformaldehyde in 0.1 mol/l phosphate buffer for 24 hrs. After paraffin-embedding, 1-μm-thick sections can be cut and used for H&E staining, Nissl staining and immunohistochemical analysis.

Immunohistochemical study can be performed with antisera against myeloperoxidase (DAKO, USA), and G-CSFR (Santa Cruz Biotechnology Inc., USA). Antisera can be generated in rabbits immunized with the isolated human protein (anti-myeloperoxidase) or with a synthetic peptide mapping the carboxy terminus of G-CSFR of mouse origin, respectively. For antigen retrieval, sections provided for G-CSFR immunohistochemistry can be heated for 20 min in a 10 mM citrate buffer at 99° C. Sections can be then incubated in normal swine serum (10% in phosphate-buffered saline) for 30 min and then in the primary antisera overnight at 4° C. The primary antibodies can be diluted 1:150 (myeloperoxidase) 1:400 (G-CSFR). Immunoreactivity can be visualized by the avidin biotin complex method. (Vectastain, Vector Laboratories, USA). Sections can be developed in 0.02% diaminobenzidine (DAB) with 0.02% hydrogen peroxide. The reaction product can be intensified by the addition of 0.02% cobalt chloride and nickel ammonium sulfate. Neuronal survival after TBI can be measured by quantifying neurons under the microscope (magnification×40) in the hippocampus of G-CSF treated animals and controls. Invasion of neutrophilic granulocytes (NG) can be measured semiquantitatively on a four point scale (0=MPO negative, 1=low MPO expression, 2=moderate MPO expression, 3-strong MPO expression).

Statistical Analysis

Values are displayed as means±SD. After acquiring all the data, the randomization code can be broken. ANOVA and subsequent post hoc Fisher protected least significant difference test can be used to determine the statistical significance of differences in continuous variables such as physiological parameters. The t-test can be used for comparison of neuronal damage and immunohistochemical data. The Mann-Whitney U test can be performed for nonparametric data such as the mortality rate and MPO immunohistochemistry. A p value <0.05 is considered statistically significant.

Based on the effect of hematopoietic factors, such as GMCSF and GCSF, and the effects of agonizing the cognate receptors on neuronal cells, another embodiment of the present invention is to treat brain tumors or other neurological cancers by antagonizing the GMCSF and/or GCSF receptors on the cancerous cells.

Neuronal Stem Cells

Recently, the importance of forming new nerve cells (neurogenesis) for treating neurological disease has been recognized. Unlike many other tissues, the mature brain has limited regenerative capacity, and its unusual degree of cellular specialization restricts the extent to which residual healthy tissue can assume the function of damaged brain. However, cerebral neurons are derived from precursor cells that persist in the adult brain, so stimulation of endogenous neural precursors in the adult brain could have therapeutic potential.

Neurogenesis occurs in discrete regions of the adult brain, including the rostral subventricular zone (SVZ) of the lateral ventricles and the subgranular zone (SGZ) of the dentate gyrus (DG). Neurogenesis occurs in the adult animal especially after a particular neurological paradigm (e.g. cerebral ischemia (Jin, et al. (2001), *Proc. Natl. Acad. Sci. USA,* 98, 4710-5, Jiang, et al. (2001), *Stroke,* 32, 1201-7, Kee et al. (2001), *Exp. Brain. Res.,* 136, 313-20, Perfilieva, et al. (2001), *J. Cereb. Blood Flow Metab.,* 21, 211-7)). Neurogenesis has also been demonstrated in humans (Eriksson et al. (1998), *Nat Med,* 4, 1313-7.), and indeed leads to functional neurons (van Praag, et al. (2002), *Nature,* 415, 1030-4). In particular, the subgranular zone of the dentate gyrus, and the hilus has the potential to generate new neurons during adult life (Gage, et al. (1998), *J Neurobiol,* 36, 249-66). It is striking that the GCSF Receptor is expressed in this area (FIG. 4*a,d*). Together with the surprising data demonstrating improvement of functional outcome after GCSF treatment (FIG. 8), and the fact that GCSF is a stem cell factor in another system (hematopoesis), it is expected that GCSF exerts part of its actions, especially the long-term effects observed (FIG. 8) via its stimulating function on adult stem cells at least in the dentate gyrus.

Figure 12:
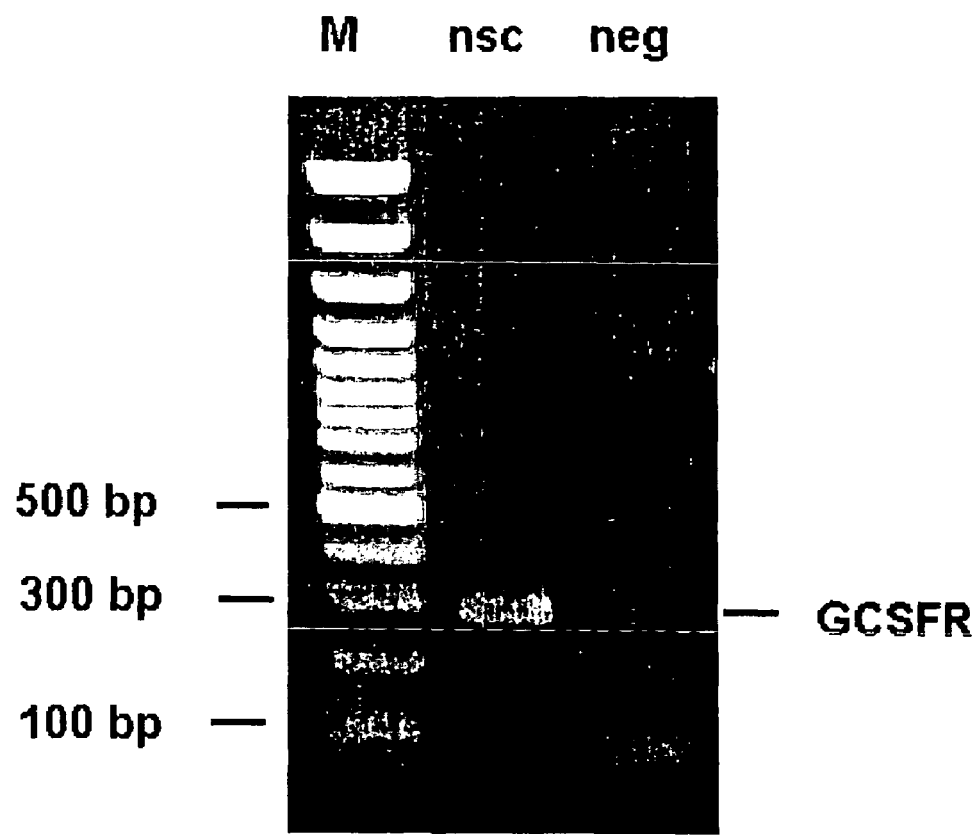
FIG. 12 demonstrates the presence of the GCSF receptor on adult neuronal stem cells (nsc) by RT-PCR (reverse transcription PCR). Shown is an agarose gel. Lane 1: size marker; lane 2: PCR products from neuronal stem cells (nsc), visible is the rat GCSFR-specific band (279 bp); lane 3: negative control.
Figure 13:
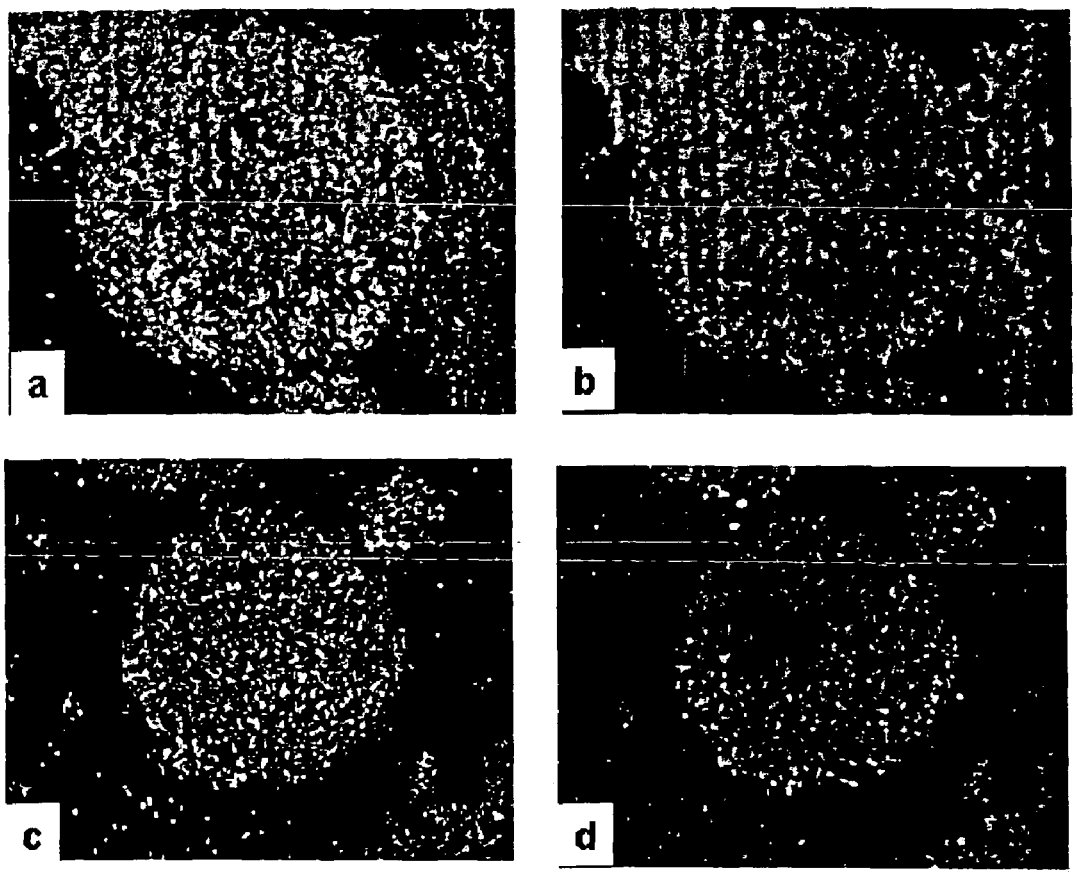
FIG. 13 demonstrates the presence of the GCSF-Receptor and GCSF on neural stem cells. A. DAPI stain of a neurosphere for visualization of all cells, B, the same neurosphere stained with an antibody directed against the GCSF receptor. C,D neurosphere stained with DAPI (C) and an antibody for GCSF (D).
Figure 16:
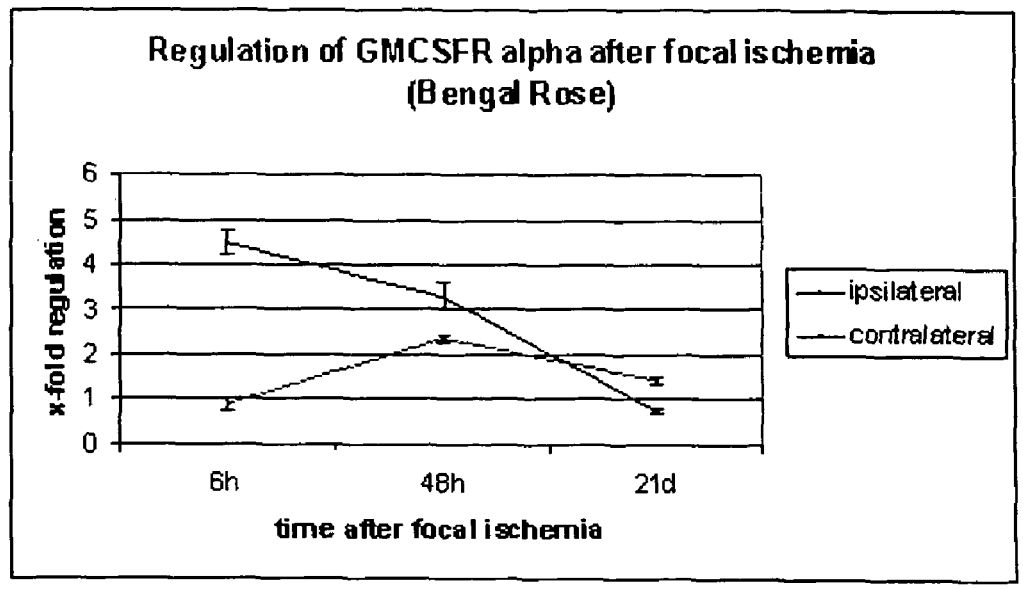
FIG. 16 shows the verification of the upregulation of the GMCSF-Receptor in the bengal-rose model at 48 h by quantitative RT-PCR by applying the LightCycler-System. Samples were taken at 6 h, 48 h and 21 d after induction of photothrombosis and induction levels were compared to sham-operated animals. On the ipsilateral hemisphere the upregulation of the GMCSF receptor is maximal early after the cortical ischemia and drops steadily until day 21. On the corresponding contralateral cortex-sample, the upregulation is seen most clearly at 2 days after the infarct, and is still moderately upregulated at day 21. This regulation pattern on the contralateral side is reminiscent of the GCSF receptor (see above).
Figure 20:
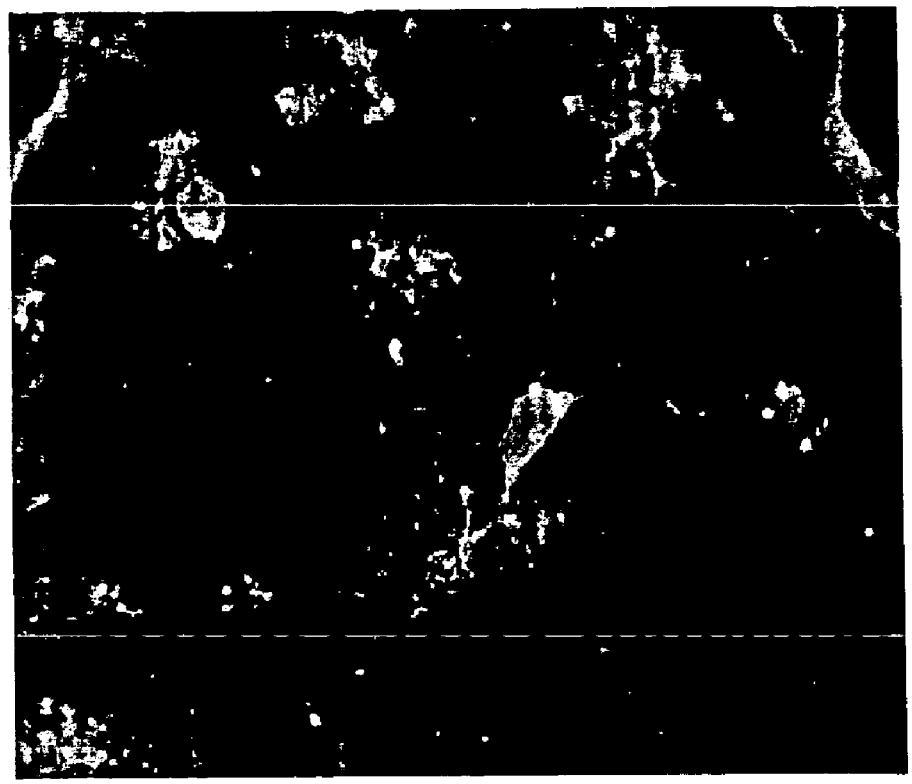
FIG. 20 shows a staining for the GMCSFR alpha on cortical neuronal cultures. The receptor is both present on the somata and processes of the neurons (verified by double labeling with an antibody directed against the nuclear epitope NeuN, and an antibody for synaptophysin, which is not included in the Figure). Preincubation of the antibody with the respective peptide, or omission of the primary antibody did not result in specific staining (not shown).
Figure 21:
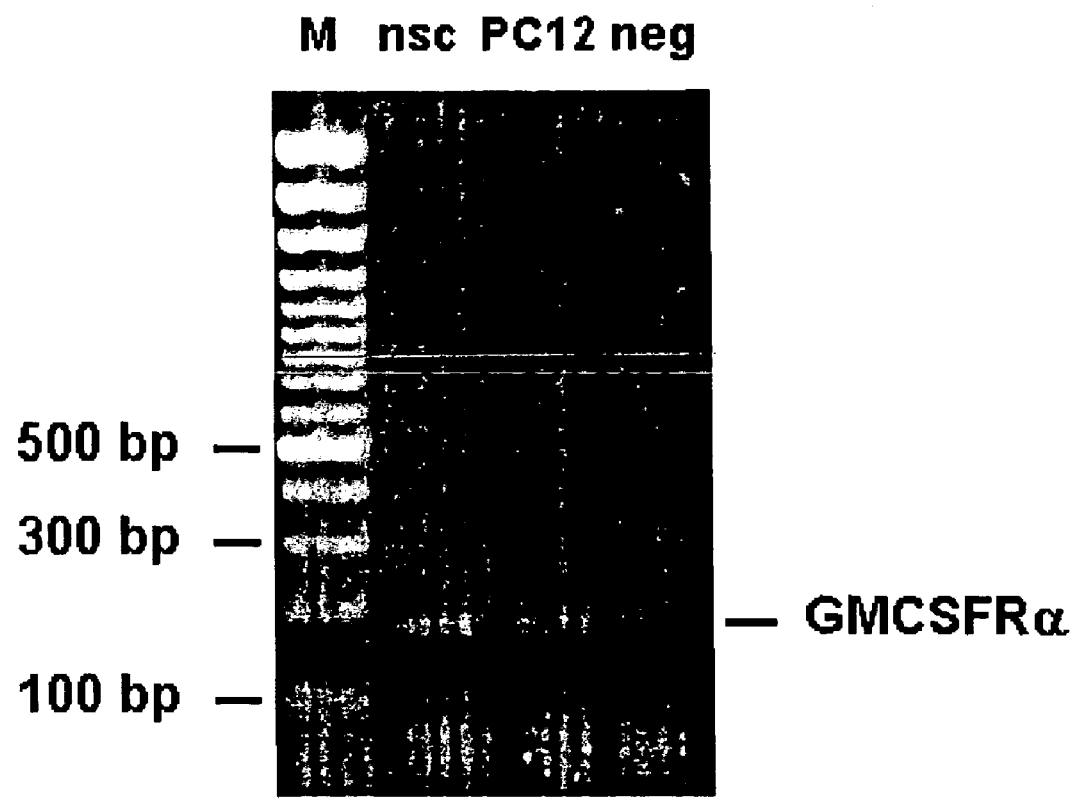
FIG. 21 demonstrates the presence of the GMCSF-receptor alpha on adult neuronal stem cells (nsc) and on PC 12 cells (PC 12) by RT-PCR. Shown is an agarose gel. Lane 1: size marker (M); lane 2: PCR on neuronal stem cells (nsc); lane 3: PCR on PC12 cells (PC12); lane 4: negative control (neg). The rat GM-CSFR alpha-specific band (176 bp) is visible in lanes 2 and 3.

This is confirmed in the present application by demonstrating the presence of the GCSF receptor on adult neuronal stem cells, isolated from hippocampal region encompassing the dentate gyrus from rat (FIGS. 12 and 13). The importance in neurogenesis provides another reason for the applicability and usefulness of GCSF treatment in all facets of neurodegenerative disease, and all conditions where neurons die. In contrast to acting on endogenous stem cells in the brain for the treatment of neurological conditions, GCSF can be applied to in vitro manipulations of stem cells, for example differentiation and proliferation. Stem cell therapy in humans is presently being explored for a number of diseases, in particular Parkinson's disease and stroke. It is desirable to differentiate stem cells in culture to particular types of neural cells, e.g., dopaminergic cells for the treatment of Parkinson's disease. Differentiated, or otherwise adapted cells to the new environment, are then administered via different routes to the organism. In Parkinson's disease, for example, stem cells have been injected directly into the brain to substitute for the loss of dopaminergic neurons in the substantia nigra ("replacement therapy")(Arenas (2002), Brain Res. Bull, 57, 795-808, Barker (2002), Mov. Disord., 17, 233-41).

Therefore, one embodiment of the present invention is to stimulate the growth and differentiation of neuronal stem cells or precondition neuronal stem cells prior to implantation into a mammal using the hematopoietic growth factors and derivatives thereof. A further embodiment of this method is to utilize these neuronal stem cells in methods for treating neurological disease as described herein, preferably in methods which provide a neuroprotective effect when the neuronal stem cells are administered to the individual.

In one embodiment, the stem cells can be administered intravenously or intra-arterially. It has been shown, for example, in cerebral ischemia or traumatic brain injury, that bone marrow stromal cells injected i.v. find their way to target areas in the brain (Mahmood, et al. (2001), Neurosurgery, 49, 1196-203; discussion 1203-4, Lu, et al. (2001), J Neurotrauma, 18, 813-9, Lu, et al. (2002), Cell Transplant, 11, 275-81, Li et al. (2002), Neurology, 59, 514-23). Stem cells may thus be treated by GCSF or GMCSF, or other hematopoetic factors in vitro, and then injected via different routes to patients with any of the diseases described herein.

In one embodiment of the present invention, the stem cells that are transplanted are genetically engineered to express factors that are secreted, and enhance the survival of neighboring cells, or lead to increase proliferation and/or differentiation of adult endogenous stem cells. For example, stem cells may be engineered to stably express GCSF, GMCSF, and/or one or more additional hematopoietic factors; and then be delivered to the central nervous system to constantly secrete GCSF or GMCSF, or other hematopoetic factors to the local environment.

Stem cells can be treated with GCSF, GMCSF, and/or other hematopoetic factor receptor agonists. Stem cells that can be used include immortalized stem cells (e.g., oncogene immortalized), neurospheres, and embryonic stem cell (ES)-derived neural cells (Gottlieb (2002), Annu Rev Neurosci, 25, 381-407), but can also include cells like bone marrow stromal cells, or umbilical cord cells (Lu, et al (2002), Cell Transplant, 11, 275-81 Li et al (2002), Neurology, 59, 514-23.) Transplantation of stem cells of variable types is a therapeutic possibility in a variety of neurological diseases, including Parkinsons disease (Isacson (2002), Brain Res Bull, 57, 839-46) and stroke (Kondziolka, et al. (2002), J Clin Neurosci, 9, 225-30.).

The stem cells, e.g., human neuronal stem cells, can be treated with factors to condition them prior to transplantation. One example of those conditioning factors is growth factors. One example of conditioning is differentiating them in the direction of desired cells, e.g. neurons. (Svendsen, et al. (1999), Brain Pathol, 9, 499-513). The presence of the GCSF receptor on stem cells indicates the importance of agonists for this receptor for conditioning these cells. Adult neuronal stem cells can be treated with different concentrations of GCSF, or other GCSF receptor agonists, and assayed for increased differentiation potential by a quantitative PCR approach, e.g., by quantifying the ratio of neuronal markers (Map2, NSE (neuron-specific enolase), neurofilament, NeuN) compared to markers of neuronal stem cells (nestin). An increased ratio after treatment signals an increased differentiation of stem cells towards the neuronal lineage. A suited concentration and time window can be used to treat stem cells prior to transplantation for neurological disease.

In another embodiment of the invention, GCSF, GMCSF, derivatives thereof as well as GCSF and GMCSF receptor agonists can be used to facilitate culturing of neural cell, such as, for example, neural stem cells. In this method, the GCSF, GMCSF, derivatives thereof as well as GCSF and GMCSF receptor agonists can be added to the media and premixed before adding to the cells or can be added into the media in which the cells are being cultured. In another embodiment of this method, the neural cells are transfected with a polynucleotide which encoded GCSF, GMCSF, and derivatives thereof, which when transfected express the respective factors in the cell.

Administration/Formulation/Dosage

The mammal to be treated can be, for example, a guinea pig, dog, cat, rat, mouse, horse, cow, sheep, monkey or chimpanzee. In one embodiment, the mammal is a human. Likewise, in one embodiment the hematopoietic factors, such as GCSF and GMCSF used for therapy or prophylaxis is a human factor or derived from a human source.

A therapeutically effective amount of the hematopoeitic factors for use in the methods of treating neurological disease when the factors are used either singularly or in combination should be used in an amount that results in a neuroprotective effect. Such an amount can range from about 100 ng to about 10 mg/kg body weight per factor or as a combination and can be determined based on age, race, sex, and other factors based on the individual patient. For example, an amount of GCSF for use in the present methods would be from about 5 to about 60 µg/kg and for GMCSF from about 5 to about 750 µg/kg body weight. When the factors are administered in combination, they may be premixed prior to administration, administered simultaneously, or administered singly in series. The route of administration can include the typical routes including, for example, orally, subcutaneously, transdermally, rectally, intravenously, intraarterially, by direct injection to the brain, and parenterally. Based on the mode of administration, and under consideration of the relevant pharmokinetics involved, the dose may be further modified, e.g., for a direct injection into the brain the dose would be lower, and the amount would be specified in absolute doses, based on local availability of GCSF, GMCSF or their derivative (e.g., 5 µg total dose). Preferably, GCSF, GMCSF and the other hematopoietic factors and derivatives thereof are administered intravenously, subcutaneously, or by direct intracerebral injection, which may be performed with an osmotic pump.

In another embodiment, GCSF, GMCSF and the other hematopoietic factors and derivatives thereof can be provided to the individual by administrating one or more nucleic acids that encodes these factors. The coding sequence nucleic acid is preferably administered in the form of a recombinant vector, such as a viral vector. The selection of a suitable vector and expression control sequences as well as vector construction is known. Examples, of viral vectors include an adenovirus (Acsadi et al., *Hum. Gene Ther.* 7(2): 129-140 (1996); Quantin et al., *PNAS USA* 89(7): 2581-2584 (1992); and Ragot et al., *Nature* 361 (6413): 647-650 (1993)), an adeno-associated viral vector (Rabinowitz et al., *Curr. Opin. Biotechnol.* 9(5): 470-475 (1998)), a retroviral vector (Federico, *Curr. Opin. Biotechnol.* 10(5): 448-453 (1999)), a *Herpes simplex* viral vector (Latchman, *Gene* 264(1): 1-9 (2001)), a lentiviral vector, a Sindbis viral vector, or a Semliki forest viral vector. Suitable vectors are also liposomes containing proteins that will attach to neural cells, e.g., virus epitopes, and contain either nucleic acid encoding GCSF or GMCSF, or protein, or oligonucleotides. An example of such a transfer system is the HVJ-liposome (Kaneda, et al. (2002), *Mol Ther,* 6, 219-26. Kaneda (1999), *Mol Membr Biol,* 16, 119-22.). Preferably, the isolated and purified nucleic acid encoding and expressing the protein or polypeptide is operably linked to a promoter that is suitable for expression in neural cells. These and other suitable vectors are reviewed in Kay et al., *Nature Medicine* 7: 33-40 (2001); Somia et al., *Nature Reviews* 1: 91-99 (2000); and van Deutekom et al., *Neuromuscular Disorders* 8: 135-148 (1998).

Suitable promoters for operable linkage to the isolated and purified nucleic acid are known in the art. Preferably, the isolated and purified nucleic acid encoding the polypeptide is operably linked to a promoter selected from the group consisting of the muscle creatine kinase (MCK) promoter (Jaynes et al., *Mol. Cell Biol.* 6: 2855-2864 (1986)), the cytomegalovirus (CMV) promoter, a tetracycline/doxycycline-regulatable promoter (Gossen et al., *PNAS USA* 89: 5547-5551 (1992)).

Generally, to ensure effective transfer of the vectors of the present invention, about 1 to about 5,000 copies of the vector are employed per cell to be contacted, based on an approximate number of cells to be contacted in view of the given route of administration, and it is even more preferred that about 3 to about 300 pfu enter each cell. These viral quantities can be varied according to the need and use whether in vitro or in vivo. The actual dose and schedule can also vary depending on whether the composition is administered in combination with other compositions, e.g., pharmaceutical compositions, or depending on individual differences in pharmacokinetics, drug disposition, and metabolism. Similarly, amounts can vary in in vitro applications depending on the particular type of cell or the means by which the vector is transferred.

The above-described proteins or derivatives thereof, substances or nucleic acids can be formulated for medical purposes according to standard procedures available in the art, e.g., a pharmaceutically acceptable carrier (or excipient) can be added. A carrier or excipient can be a solid, semi-solid or liquid material which can serve as a vehicle or medium for the active ingredient. The proper form and mode of administration can be selected depending on the particular characteristics of the product selected, the disease, or condition to be treated, the stage of the disease or condition, and other relevant circumstances (*Remington's Pharmaceutical Sciences,* Mack Publishing Co. (1990)). The proportion and nature of the pharmaceutically acceptable carrier or excipient are determined by the solubility and chemical properties of the substance selected the chosen route of administration, and standard pharmaceutical practice. The pharmaceutical preparation may be adapted for oral, parenteral or topical use and may be administered to the patient in the form of tablets, capsules, suppositories, solution, suspensions, or the like.

The growth factors, derivatives thereof, a nucleic acid coding sequence thereof of the present invention, while effective themselves, can be formulated and administered as pharmaceutically acceptable salts, such as acid addition salts or base addition salts, for purposes of stability, convenience of crystallization, increased solubility, and the like.

For some neurological diseases, especially in ischemic diseases it is crucial for an effective therapy not to delay the onset of the therapy. In a preferred embodiment, the present invention relates to a method, wherein GCSF, GMCSF, or a derivative thereof or a substance activating STAT proteins or an agonist to the GCSF or GMCSF receptors is administered within 24, preferably within 10, most preferably within 3 to 6 hours after the occlusion of a blood vessel, or the onset of neurological symptoms, or an otherwise detected onset of an ischemic event. As GCSF and GMCSF also have beneficial effects for long-term functional improvement, treatment begins at considerable time after the ischemic insult is also possible (e.g., 1 day to 7 days after the insult). Treatment may be continued for several days and weeks after the ischemic event, as a means to improve functional recovery of the patient in analogy to the functional improvement seen in our long-term cortical infarct model (see FIG. 8). Treatment may consist of several doses per day (e.g. short i.v. infusions) to reach steady-state trough levels of GCSF, GMCSF or related factors. Treatment may also include continuous slow infusion of the described substances (e.g., by a perfusor unit) to guarantee steady serum levels.

In the case of chronic neurodegenerative processes, such as Parkinson's disease, or amyotrophic lateral sclerosis, treatment will more likely consist in one daily dose of GCSF or related factors, or preferably use slow-release formulations, or more stable derivatives of GCSF or related factors.

Screening for Neuroprotective Substances which Bind to a GCSF or GMCSF Receptor on Neural Cells For practicing the present invention, derivatives of GCSF, GMCSF (e.g., GCSF- or GMCSF-mimetics), and/or other hemotopoietic factors that retain their potential to protect neurons and that also have diminished action on leukocytes, thereby reducing potential adverse effects, are preferred. Therefore, one embodiment of the present invention is to screen for compounds that bind to the GCSF or GM-CSF receptor on neural cells and which stimulate the neuroprotective effect observed with GM-CSF or GCSF as described in this application.

Derivatives of GCSF, e.g., GCSF-mimetics, can be tested in an in vitro neuroprotective assay such as exemplified in Example 10. This neuroprotective assay can be varied without changing the basic principle of the test by adapting for, for example, (i) other damaging stimuli like Interleukin-1, oxygen deprivation, A4 peptides, FAS ligand, or (ii) other cells, e.g. neuronal-like cells like SH-SY5Y cells, or PC12 cells, or (iii) other readouts for cell-viability or cell-death such as e.g. DNA-fragmentation, nuclear condensation, activity of co-transfected beta-galactosidase, detection of a fluorigenic substrate of caspases etc. All these numerous adaptations are known and may also be used in high-throughput systems. High throughput screening technology is commonly used to define the rapid processing of cells on a large scale. Substances demonstrating a positive neuroprotective effect in this assay can be further tested for their granulopoetic activity as, for example, described in Tian et al., *Science* 281, 257-259. Selection of GCSF derivatives is preferably based on the comparison of these two specific effects elicited by the test substances with those effects elicited by known forms of GCSF. Likewise, derivatives of GMCSF, e.g., GMCSF-mimetics can be tested in an in vitro neuroprotective assay as described for GCSF.

Further neuroprotective substances can be obtained by measuring the presence of activated transcription factors such as STAT-proteins, including STAT-3 and STAT-5 in neuronal or neuron-like cells (for example, PC12, SH-SY5Y, hNT, NT2, hn33) after exposure of these cells to a test substance. Therefore, in another embodiment of the present invention, the ability of a particular substance or compound to act as an agonist to the GCSF or GMCSF receptor can be assessed by the activation of the STAT proteins, e.g., STAT3 and/or STAT5, in neuron-like cells as described herein and using conventional gene expression assays, such as quantitative PCR by LightCycler™ or Taqman™ analysis.

Activated STAT proteins are phosphorylated (pSTAT) and can be detected by a commercially available pSTAT-specific antibody (Santa Cruz Biotechnology) in Western Blot or in immunohistochemical studies, or ELISAs.

Alternatively, STAT activity can be measured using a reporter construct which includes a STAT-responsive promoter element (for example, a multimerized STAT-binding element, such as a multimerized STAT-3 or STAT-5-binding element) linked to a reporter gene, such as luciferase, SEAP (secreted alkaline phosphatase), chloramphenicol transferase (CAT), green fluorescent protein (GFP), or other common gene expression reporters. After transfecting cells with reporter construct, the cell is contacted with the test substance and the amount of the reporter expression can be identified. This method of measuring STAT activity can be adapted to a high-throughput format.

A typical reporter assay can be conducted using, for example, commercially available assay systems (Mercury Pathway Profiling System from Clontech; Path Detect-System from Stratagene). An example of a protocol that can be performed is as follows.

Cells are cultured in a multiwell plate, e.g. 20.000 cells per well in a 96 well plate. Two days after seeding the cells culture medium is exchanged to an serum-free medium (40 µl per well) and cells can be transfected with a reporter plasmid, encoding the STAT-binding element and the reporter protein (STAT-3_firefly-luciferase plasmid; 50 ng/well), and a transfection control plasmid (renilla-luciferase expression plasmid; 10-20 ng/well) under optimized conditions referring to each cell type (for example: PC-12 cells can be transfected by lipofection using LIPOFECTAMINE2000™, Invitrogen, as recommended). 48-72 h after transfection the assay can be run. Cells are stimulated with the testing substance in multiple concentrations which should cover a broad range of concentrations. Multiple assaying time points starting within 5 minutes of stimulation should be chosen. When using a Luciferase assay, the readout can be assessed in a Luminometer, plate format (Berthold, Germany), measuring stepwise the activity of renilla and firefly luciferase. The detection of the two luciferase-activities is done by the use of commercially available detection kits (Dual luciferase reporter assay kit, Promega; Luciferase reporter assay kit, Clonetech). Values of firefly luciferase are then normalized to renilla luciferase values and relative induction of reporter gene can be calculated.

In an alternative example of a screening method, the agonist activity on the GCSF or GMCSF receptor on neuronal cells can be utilized and measured. For example, the homodimerization upon ligand binding can be assayed by using fluorescence resonance energy transfer measurements (FRET, or BRET (bioluminescence resonance energy transfer) (Siegel R M et al *Sci STKE* (2000) 2000 (38):L1; Xu Y et al *Proc Natl Acad Sci USA* (1999) 96(1):151-6), or reporter systems for dimerization events, e.g. the double switch system (DE 10211063.8), the beta-gal reporter system (Rossi F et al *Proc Natl Acad Sci USA* (1997) 94 (16):8405-10), or the split-ubiquitin system (WO 954/29195, U.S. Pat. No. 5,585, 245, or Johnsson, N. and Varshavsky, *Proc Natl Acad Sci USA* (1994) 91 (22):10340-4).

Having generally described this invention, a further understanding can be obtained by reference to certain specific examples which are provided herein for purposes of illustration only and are not intended to be limiting unless otherwise specified.

EXAMPLES

The experiments underlying the present invention demonstrate that GCSF is neuroprotective in vitro, and that GCSF displays significant infarct reducing effects after transient focal cerebral ischemia. Neurons in the periphery of the infarction but also on the contralateral side exhibited specific binding of anti GCSFR-antibody, indicative for a GCSF receptor. The presence of GCSFR on neurons is novel and was verified by Western blot, RT-PCR, and a detailed immunohistochemistry in the brain, and by PCR and immunocytochemistry in cultured primary neurons. Furthermore, STAT3 activation as judged by nuclear translocation of STAT3 was significantly increased in neurons of the penumbra of GCSF treated animals compared to controls suggesting a GCSFR/STAT mediated mechanism of action. In the in vivo ischemic experiment (middle cerebral artery occlusion, MCAO) there was no effect on cerebral blood flow as measured by laser Doppler flowmetry (ldf) when comparing both groups. There were no significant differences in physiological parameters and weight decline between both groups during the MCAO experiment. Mortality rate was significantly improved in animals treated with GCSF compared to controls in the MCAO experiment. Neutrophilic blood count (NGC) was significantly increased after 24 hours in GCSF treated animals compared to controls. Myeloperoxidase (MPO)-staining as a measure of invading neutrophilic granulocytes (NGs) into the ischemic hemisphere was not significantly different between GCSF treated animals and controls.

The dose of the i.v. delivered GCSF (60 µg/kg/body weight) used in the experiments was comparable to the doses used for other experimental conditions. It had been tested for safety in an earlier pilot project before and consequently no significant side effects were observed. This dose (60 µg/kg/body weight) is six times higher than the approved dose for the treatment of human myelodysblastic and other diseases, and has shown no appreciable side effects in the rat model.

An infarct reducing effect of 50% achieved with GCSF is comparable with that of other growth factors such as bFGF, or IGF after systemic application (Fisher M, et al., *J. Cereb. Blood Flow Metab.*, 1995; 15:953-9; Schäbitz W R, et al., *Stroke* 2001; 32:1226-33). It seems that glucose deprivation and excitotoxicity with subsequent $Ca^{2+}$ overload of cells as well as apoptosis, reactive oxygen species, and decreased energy reserve in the face of increased requirements (e.g., from spreading depression) are the main causes of neuronal cell death following ischemia (Lee J M, et al., *Nature* 1999; 399(Suppl):A7-14). As demonstrated in the examples, GCSF protects in vitro neuronal-like cells (NGF-differentiated PC12 cells) against $H_2O_2$ induced cell death. $H_2O_2$ elicits oxidative stress by the production of reactive oxygen species (ROS), which invokes cell death. $H_2O_2$-mediated cellular stress in mammalian cells is well-characterized in terms of cellular phenotype, dosage, time-course and signaling pathways involved. The wide-spread usage of $H_2O_2$ in a multitude of studies supports apoptotic mechanisms as effects of $H_2O_2$ in cells (see for example *FASEB J.* 2002 January; 16(1):111-3; *J Cell Biochem* 2001; 82(3):437-44). For example, roles of the pro-apoptotic Kinase ASK1 and the FasLigand have been convincingly demonstrated in $H_2O_2$-mediated cell-death (Tobiume K, *EMBO Rep* 2001 March; 2(3):222-8; Kwon, D., *J Neuroimmunol.* 2001 Feb. 1; 113(1):1-9; Facchinetti, F., *J Neurosci Res.* 2002 Jul. 15; 69(2):178-88.). Therefore, it is likely that GCSF interferes with apoptotic mechanisms invoked in cerebral ischemia. GCSF's action is probably mediated by binding to the high-affinity receptor GCSFR. Interaction with this receptor activates the Janus family kinases (JAKs) and STATs (Darnell J E Jr., *Science* 1997; 277:1630-5). JAK are non-receptor-type tyrosine protein kinases that become activated upon ligand-induced receptor dimerization. GCSF induced activation of JAKs phophorylate STATs on a conserved tyrosine residue, which induces STAT dimerization (Quelle F W, et al., *Mol. Cell Biol.* 1994; 14:4335-41). Furthermore, STATs translocate to the nucleus and subsequently regulate gene expression (Shuai K, et al., *Nature* 1993; 366:580-3; Shuai K., *Oncogene* 2000; 19:2638-44). STAT3 is the principal STAT protein activated by GCSFR (Shuai K., *Oncogene* 2000; 19:2638-44). STAT3 mediates antiapoptotic function by activating bcl-2 and induces proliferation and differentiation of granulocytes by upregulating the c-myc gene (Fukada T, *Immunity* 1996; 5:449-60; Shimozaki K, *J. Biol. Chem.* 1997; 272:25184-9). As shown here by using immunohistochemistry, RT-PCR, and Western-Blot GCSFR exists not only on hematopoetic cells but also on neurons, glial cells, neuronal-like cells, and neuronal stem cells. Furthermore, GCSF induced STAT3 upregulation in neurons of the penumbra may mediate antiapoptotic effects such as bcl-2 upregulation as shown for BDNF or bFGF, (Schäbitz W R et al., *Stroke* 2001; 32:1226-33) and provide trophic support of neurons to survive. Dense nuclear labeling of STAT3 in the penumbra of the infarction could reflect membrane receptor-mediated translocation of STAT3 from the cytoplasm to the nucleus which was already shown for activated microglia after cerebral ischemia (Planas A M, et al., *Eur. J. Neurosci.* 1996; 8:2612-8). GCSF is known to stimulate release, enhancement of effector function, and extension of lifetime by delaying apoptotic cell death of neutrophilic granulocytes (NGCs), the body's first line of defense against all kinds of infections (Hartung T., *Curr Opin Hematol* 1998; 5:221-5). Neutrophils could occlude microvessels, subsequent invasion of leukocytes triggers the release of proteolytic enzymes, oxygen free radicals, interleukines, and TNF-α—effects known to deteriorate infarct size and outcome after cerebral ischemia (Del Zoppo G J, *Stroke* 1991; 22:1276-83; Jean W C, et al., *Neurosurgery* 1998; 43:1382-96; Matsuo Y, et al., *Brain Res.* 1994; 656:344-52). In contrast, GCSF has significant anti-inflammatory effects: GCSF reduces in models of peripheral infections TNF-α, IL-1β, IL-2, IL-6 and IL-8 and elevates IL-1β receptor-antagonists (Gorgen I, et al., *J Immunol* 1992; 149:918-24; Heard S O, et al., *Crit. Care Med.* 1999; 27:1019-21; Heard S O, et al., *Crit. Care Med.* 1998; 26:748-54; Hebert J C, et al., *Arch. Surg.* 1990; 125:1075-8; Lundblad R, et al., *Crit. Care Med.* 1996; 24:820-6.; Squadrito F, et al., *Br J Pharmacol* 1997; 120:333-9.). GCSF decreased TNF-α release in vitro and in vivo in healthy volunteers and elevated levels of antagonists for TNF, IL-6, IL-8, and IL-1β (Hartung T. *Curr Opin Hematol* 1998; 5:221-5; Gorgen I, et al., *J. Immunol.* 1992; 149:918-24; Heard S O. et al., *Crit Care Med* 1999; 27:1019-21). Moreover, reduced neutrophil infiltration in lung and ileum was observed in a model of splanchnic ischemia and reperfusion 15 minutes after administration of GCSF and reperfusion of the small bowel (Squadrito F, et al., *Br J Pharmacol* 1997; 120:333-9.). Consistent with these findings an increase of neutrophil infiltration into the ischemic hemisphere was not found although total neutrophilic granulocytes (NGCs) increased after GCSF treatment.

Another possible mechanism of action of growth factors in particular bFGF includes effects on cerebral blood flow. bFGF treatment dilates collaterals in the peri-ischemic zone even at doses not promoting systemic hypotension, thus increasing the blood flow to the penumbral regions (Tanaka R, et al., *Stroke* 1995; 26:2154-8; discussion 2158-9). However, as shown here, GCSF treatment did not reduce systemic blood pressure or change cerebral blood flow compared with the control group as measured by LDF.

In the photothrombotic bengal rose model, postischemic intravenous GCSF treatment clearly improved sensory motor functional outcome six weeks after photothrombotic stroke, further supporting the hypothesis that growth factors induce recovery and regeneration after traumatic brain lesions in vivo. Two other compounds, basic fibroblast growth factor (bFGF) and osteogenic protein-1 (OP-1) were reported before to improve sensorimotor function and to induce neuronal sprouting after focal cerebral ischemia (Kawamata et al *Proc Natl Acad Sci USA* 1997; 94:8179-84; Kawamata et al *Neuroreport* 1998; 9:1441-5; Ren et al *Neuropharmacology* 2000; 39:860-5). In most of these studies growth factors were administered into the cerebral ventricles which is clinically not relevant. Only Ramirez et al. (Ramirez, et al. (1999), *Neuroreport*, 10, 1201-4.) reported that intravenous administration of bFGF supports lesion-induced hippocampal sprouting, but the authors did not study functional outcome measures. The results presented here indicate that a clinically relevant dose protocol of GCSF administration induces functional recovery after cerebral ischemia. The capacity for enhancement of plasticity is clearly not limited to ischemic brain damage, but also relevant for neurodegenerative diseases such as Parkinson's disease and amyotrophic lateral sclerosis (ALS), the trinucleotide repeat diseases, cerebral ischemias due to resuscitation or intrapartal problems, probably also to dementias such as Alzheimer's disease, and to the neurodegenerative aspects of schizophrenia.

Overview of the Methods for the Experiments on Cerebral Ischemia

Ischemia was induced by using the suture occlusion model of the middle cerebral artery (90 min) in the rat. 30 min after induction of ischemia, animals (n=12 per group) received 60 μg/kg body weight of GCSF intravenously for 90 min or vehicle. Infarct volume was calculated based on TTC (2,3,5-triphenyltetrazolium chloride)-staining 24 hours after ischemia. Expression of the GCSFR was studied by immunohistochemistry, verified by RT-PCR and immunoblotting. Expression of STAT3 was studied by immunohistochemistry. Efficacy of GCSF in functional recovery was studied in the Bengal rose photothrombotic model.

Statistical Analyses

The values presented in this study are means±SD. After acquiring all the data, the randomization code was broken. ANOVA and subsequent post hoc Fisher protected least significant difference test or Bonferroni correction were used to determine the statistical significance of differences for in vitro data and physiological parameters, or functional outcome in test batteries. The t-test was used for comparison of postmortem infarct volumes, MPO, and STAT3 immunohistochemistry. The Chi-Square test was performed for mortality data. A p value <0.05 was considered statistically significant.

Results

GCSF reduced infarct volume to 131.96 mm$^3$±112.7 mm$^3$ vs 278.9 mm$^3$±91.56 mm$^3$ (p<0.05) in the control group. Immunohistochemistry, Western blotting, and RT-PCR revealed the existence of GCSF receptors in neurons and glial cells. GCSF significantly activated STAT3 in the periphery of the infarction compared to controls (p<0.05). GCSF is effective in improving functional recovery after ischemia in the model of Bengal rose photothrombosis.

It has therefore been demonstrated that GCSF has a significant neuroprotective effect in cell culture and after focal cerebral ischemia. This effect seems to be mediated by interaction with GCSFR and activation of STAT3.

Example 1

Focal Cerebral Ischemia

Procedure for Inducing Focal Cerebral Ischemia (MCAO, Middle Cerebral Artery Occlusion)

Experimental protocols were approved by the local ethics committee. Twenty-four male Wistar rats (Charles River, Germany) weighing 280 to 320 g were randomly assigned to the following groups: A (Control group, n=12, ischemia for 90 min, treatment with 2 ml saline 0.9% for 90 min beginning 30 min after vessel occlusion); B (GCSF group, n=12, ischemia for 90 min, treatment with 60 µg/kg body weight of recombinant human GCSF, Neupogen®, Amgen, Europe B.V., Netherlands, soluted in 2 ml saline 0.9% for 90 min beginning 30 min after vessel occlusion. Alternatively, any GCSF or derivative or formulation of other source (another manufacturer (e.g. Lenogastrim™ by Roche or Granocyte™ by Chugai or Albugranin™ by HGS or Neulasta™ by Roche/Amgen) can be used here.

Animals then were anesthetized with an intraperitoneal injection of 100 mg/kg body weight ketamine hydrochloride (WDT, Garbsen, Germany). Anesthesia was maintained with 50 mg/kg body weight if necessary. A PE-50 polyethylene tube was inserted into the right femoral artery for continuous monitoring of mean arterial blood pressure, blood gases, hematocrit, leukocyte count, and blood glucose levels. The right femoral vein was cannulated by a PE-50 tube for treatment infusion. During the experiment rectal temperature was monitored and maintained at 37° C. by a thermostatically controlled heating pad (Föhr Medical Intruments, Germany). Transient focal cerebral ischemia was induced by using the suture occlusion model as described in detail by Zea Longa et al. (*Stroke* 1989; 20:84-91). Briefly, the right common carotid artery and the right external carotid artery were exposed through a midline neck incision. A 4-0 monofilament nylon suture (Ethicon, Germany) coated with silicon (Bayer, Germany) was inserted through an arteriectomy in the common carotid artery, gently advanced into the internal carotid artery and positioned approximately 17 mm from the carotid bifurcation. Using this technique, the tip of the suture occludes unilaterally the proximal anterior cerebral artery, the origins of the MCA and the posterior communicating artery. A large infarct in the territory of the MCA is typically produced. Reperfusion was performed by withdrawal of the occluder filament 90 minutes after vessel occlusion. Sham-operated animals underwent the same experimental procedures as described above but the nylon filament was not advanced beyond the common carotid artery, so that no infarction occurred. After surgery, the catheters were removed, and the animals were allowed to recover from the anesthesia and given food and water ad libitum.

Measurement of Regional Cerebral Blood Flow

Laser-Doppler flowmetry (LDF) (Periflux 4001 Master, Perimed AB, Sweden) was used to monitor cerebral blood flow (CBF) before, during and after occlusion of the MCA. After placing the animal into a stereotactic frame, the animal's skull was exposed and a hole of 1.5 mm in diameter was drilled under the microscope on the right side 4 mm lateral and 2 mm caudal to the bregma. The dura was left intact and the LDF probe (1.4 mm in diameter) was placed into the burr hole. The area selected for CBF monitoring corresponded to the ischemic penumbra of the MCA occlusion model in rats.

Infarct Volume Calculation 24 hours after MCA occlusion, the rats were anesthetized with ketamine 150 mg/kg body weight and decapitated. The brains were dissected and cut into 5 coronal slices of 2 mm thickness, incubated in a 2% solution of 2,3,5-triphenyltetrazolium chloride (TTC) at 37° C. for 30 min and fixed by immersion in a 10% buffered formalin solution. TTC-stained sections were photographed using a charge coupled device camera (EDH-1000HR Computer Camera, Electrim Corporation, Princetown, N.J., USA). A blinded investigator measured the infarct sizes with a computerized image analyzer (Bio Scan Optimas, Edmonds, Wash.). To compensate for the effect of brain edema the corrected infarct volume was calculated as previously described in detail: Corrected infarct area equals left hemisphere area minus (right hemisphere area minus infarct area) (Schäbitz W R, et al., *Stroke* 2001; 32:1226-33). Infarct volumes were expressed as a percentage of the contralateral hemisphere.

Ischemia Experiment

GCSF achieved a potent neuroprotective effect after focal cerebral ischemia. Mean infarct volume in intraperitoneal GCSF treated animals was 131,96 mm$^3$±112,7 mm$^3$ versus 278.9 mm$^3$±91.56 mm$^3$ in the control group or 9.96±8.31% (n=12) versus 22.7±6.69% of the total hemisphere (p<0.05; FIG. 1).

GCSF treatment significantly reduced mortality: Four animals in the control group and one in the GCSF-treated group died within the 24-hour reperfusion period (p<0.05). No statistical differences were observed between the control and GCSF-treated group for rectal temperature, pH, pCO$_2$, pO$_2$, hematocrit (hct), blood glucose, heart rate, mean arterial pressure, and body weight for all animals (Table 1). Leukocyte count in the peripheral blood was significantly increased 24 hours after ischemia in GCSF treated animals compared to controls (p<0.05, Table 1).

TABLE 1

| Time | Group (n = 1) | rectal Temp | pH | pCO2 (mm Hg) | pO2 (mm Hg) | Hct (%) | Gluc (mg/dL) | MABP (mm Hg) | HR (Beats/min) | Leukocytes (× 10$^9$/L) | Body Weight (g) |
|---|---|---|---|---|---|---|---|---|---|---|---|
| Pre-ischemia | Control | 37 ± 0.2 | 7.38 ± 0.03 | 39 ± 7 | 89 ± 7 | 47.4 ± 3.6 | 263 ± 25 | 98 ± 12 | 358 ± 13 | 1.9 ± 0.3 | 314 ± 25 |
| | rGCSF | 37 ± 0.3 | 7.35 ± 0.02 | 38 ± 5 | 91 ± 7 | 46 ± 0.9 | 251 ± 31 | 102 ± 15 | 350 ± 24 | 1.8 ± 0.4 | 318 ± 29 |
| 1 h | Control | 37 ± 0.1 | 7.38 ± 0.02 | 41 ± 6 | 88 ± 5 | 45.3 ± 0.8 | 160 ± 13 | 112 ± 21 | 384 ± 16 | 6.5 ± 0.6 | |
| | rGCSF | 37 ± 0.2 | 7.37 ± 0.03 | 39 ± 4 | 89 ± 8 | 44.3 ± 0.7 | 172 ± 17 | 109 ± 19 | 371 ± 27 | 6.8 ± 0.3 | |

TABLE 1-continued

| Time | Group (n = 1) | rectal Temp | pH | pCO2 (mm Hg) | pO2 (mm Hg) | Hct (%) | Gluc (mg/dL) | MABP (mm Hg) | HR (Beats/min) | Leukocytes (× $10^9$/L) | Body Weight (g) |
|---|---|---|---|---|---|---|---|---|---|---|---|
| 2 h | Control | 37 ± 0.3 | 7.39 ± 0.03 | 37 ± 3 | 87 ± 8 | 44.6 ± 0.8 | 149 ± 12 | 101 ± 14 | 368 ± 13 | 8.2 ± 0.4 | |
|  | rGCSF | 37 ± 0.2 | 7.4 ± 0.04 | 39 ± 6 | 89 ± 5 | 44.2 ± 0.4 | 152 ± 14 | 99 ± 8 | 372 ± 9 | 8.5 ± 0.3 | |
| 3 h | Control | 37 ± 0.2 | 7.38 ± 0.02 | 38 ± 5 | 91 ± 5 | 43.3 ± 0.9 | 133 ± 7 | 102 ± 16 | 366 ± 17 | 9.7 ± 0.8 | |
|  | rGCSF | 37 ± 0.1 | 7.37 ± 0.03 | 37 ± 4 | 94 ± 10 | 43.1 ± 1.2 | 141 ± 10 | 99 ± 12 | 384 ± 13 | 10.6 ± 0.5 | |
| 4 h | Control | 37 ± 0.2 | 7.36 ± 0.02 | 37 ± 6 | 87 ± 5 | 42.1 ± 0.9 | 168 ± 13 | 113 ± 24 | 373 ± 21 | 13.2 ± 0.6 | |
|  | rGCSF | 37 ± 0.3 | 7.38 ± 0.03 | 39 ± 7 | 89 ± 9 | 42.8 ± 1.1 | 174 ± 16 | 120 ± 17 | 361 ± 12 | 13.7 ± 0.6 | |
| 24 h | Control | 37 ± 0.2 | 7.37 ± 0.03 | 38 ± 4 | 86 ± 6 | 46.7 ± 1.5 | 198 ± 13 | 115 ± 17 | 365 ± 10 | *3.8 ± 0.8 | 285 ± 24 |
|  | rGCSF | 37 ± 0.2 | 7.37 ± 0.04 | 41 ± 5 | 87 ± 8 | 47 ± 0.5 | 204 ± 16 | 117 ± 21 | 359 ± 15 | 9.7 ± 0.4 | 293 ± 16 |

Table 1 lists physiological parameters of GCSF treated animals and controls.
Values are given as mean ± SD ($p < 0.05$; ANOVA; F-test).

LDF-monitoring revealed no statistical differences between the two treatment groups (data not shown).

Example 2

Immunohistochemistry in the Context of Focal Cerebral Ischemia

Immunohistochemical Methods Used

For morphological analysis of STAT3 activation (FIG. 6) and GCSFR distribution in infarcted brains, and counts of neutrophilic granulocytes, a 2-mm-thick brain slice of GCSF-treated animals and controls was immersion fixed in 4% paraformaldehyde in 0.1 mol/l phosphate buffer for 24 hrs (n=5 per group). After paraffin-embedding, 1-µm-thick sections were cut and used for H&E staining, Nissl staining and immunohistochemical analysis.

Immunohistochemical studies were performed with antisera against myeloperoxidase (DAKO, Carpinteria, Calif., USA), glial fibrillary acidic protein (GFAP) (DAKO, Carpinteria, Calif., USA), GCSFR (Santa Cruz Biotechnology Inc., Santa Cruz, Calif., USA) and STAT3 (Santa Cruz Biotechnology Inc., Santa Cruz, Calif., USA). For antigen retrieval, sections provided for GCSFR and STAT3 immunohistochemistry were heated for 20 min in a 10 mM citrate buffer at 99° C. Sections were then incubated in normal swine serum (10% in phosphate-buffered saline) for 30 min and then in the primary antisera overnight at 4° C. The primary antibodies were diluted 1:150 (myeloperoxidase), 1:400 (GFAP), 1:400 (GCSFR) and 1:100 (STAT3), respectively. Immunoreactivity was visualized by the avidin biotin complex method (Vectastain, Vector Laboratories, USA). Sections were developed in 0.02% diaminobenzidine (DAB) with 0.02% hydrogen peroxide. The reaction product was intensified by the addition of 0.02% cobalt chloride and nickel ammonium sulfate. In a subset of control slides preabsorption of the GCSFR antiserum with the respective peptide did not produce immunostaining (not shown). When omitting the primary antisera, no immunostaining was produced either (not shown).

Invasion of neutrophilic granulocytes (NG) was quantitatively measured by counting NGs per infarcted hemisphere. STAT3 protein expression was quantified in 2 overlapping fields rostro-caudal in the vincinity of the infarction of the parietal cortex and the corresponding contralateral side (magnification×400). To this end, neurons with nuclear translocation were counted, given as percent of STAT3 positive neurons from all neurons.

Results of the Immunohistochemical Experiments in Focal Cerebral Ischemia

Myeloperoxidase (MPO) staining detected no neutrophilic granulocytes (NGs) in the non-ischemic hemispheres of both groups. MPO staining was not significantly different between GCSF treated animals and controls based on quantified MPO positive cells in the ischemic hemisphere (14±17.6 versus 14.3±12.5, n.s.).

GFAP immunoreactivity (1R) was present in scattered astrocytic processes throughout the cortex, striatum and white matter of the non-infarcted hemisphere. No difference in the pattern and intensity of GFAP staining was detectable in the cortical peri-infarct zone both in untreated and GCSF treated rats. In particular, GFAP IR was not increased in the cortical penumbra, neither in the placebo group, nor in the GCSF group (not shown). Within the infarct core, scattered GFAP immunoreactive astrocytes were detectable (not shown).

Immunohistochemically, staining for GCSFR was detectable in scattered cortical neurons and neurites (not shown) both in untreated and GCSF treated animals. Glial cells were also stained with the GCSF-R antibody (not shown). In the infarct core, no GCSF-R immunreactive cells were seen. No difference in the pattern and intensity of GCSF-R IR was evident between the two experimental groups.

Figure 6:
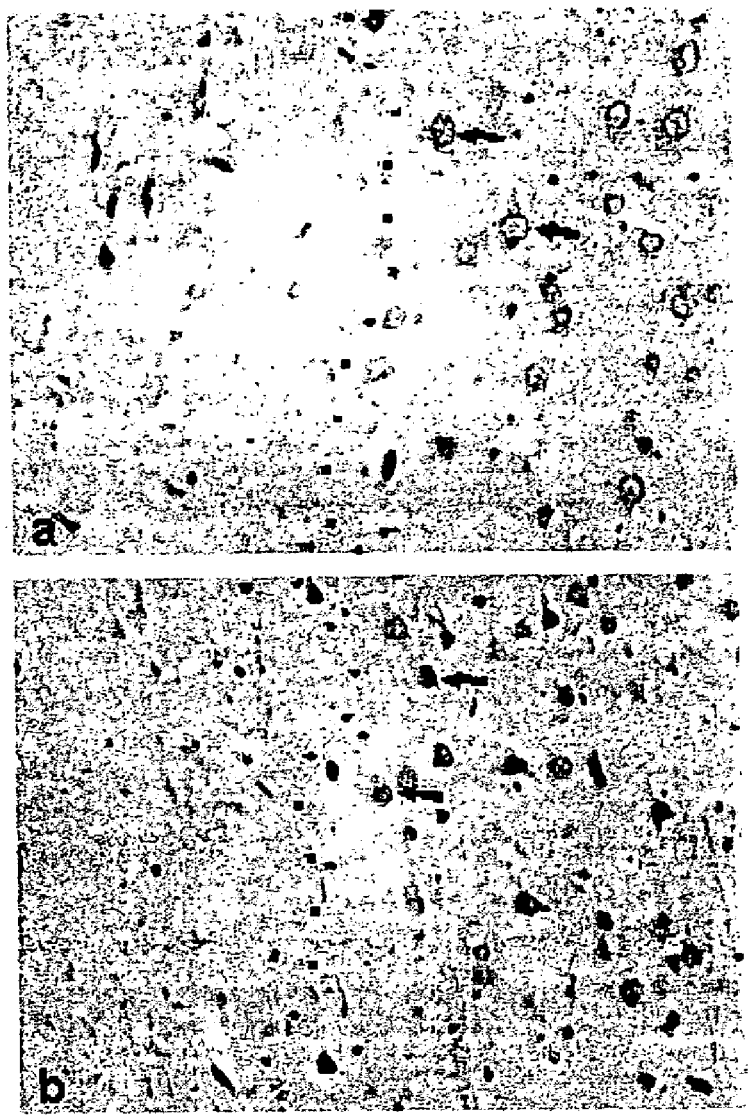
FIGS. 6 and 7 show the immunohistochemical results obtained with an antibody against STAT3.
Figure 7:
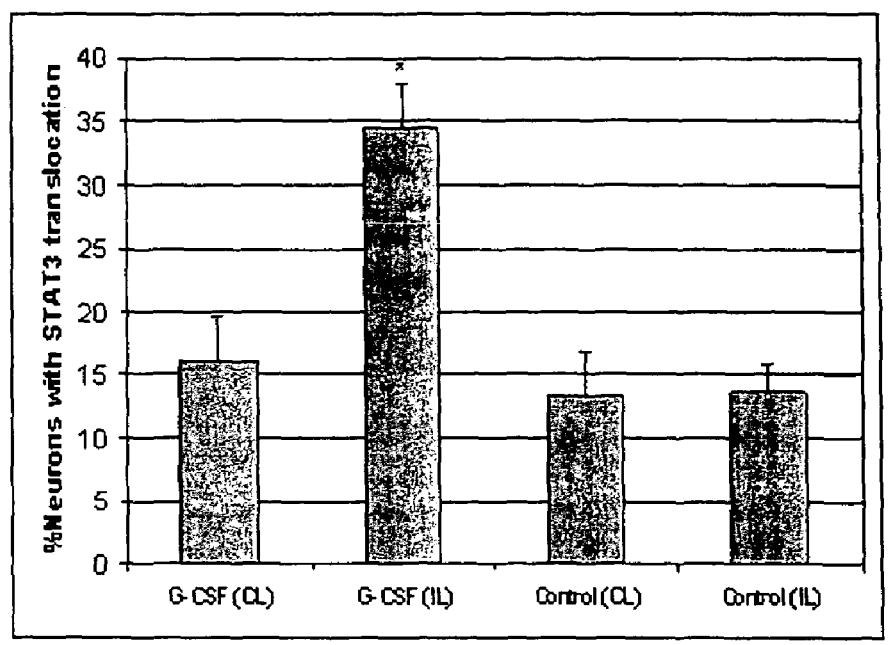

STAT3 IR was seen in scattered nuclei of neurons and glial cells within the uninfarcted hemisphere of both placebo and GCSF treated rats. Some cytoplasmic staining was also present in a few scattered neurons. STAT3 protein expression was significantly increased after GCSF treatment in the penumbra of the infarction compared to untreated controls (34.4±7.05 versus 13.7±4.4; $p<0.0003$)(FIG. 6, 7). No difference occurred on the contralateral side (16.2±6.9 versus 13.3±6.9; n.s.).

Example 3

Western Blots and PCR in the Context of Focal Cerebral Ischemia

Figure 3:
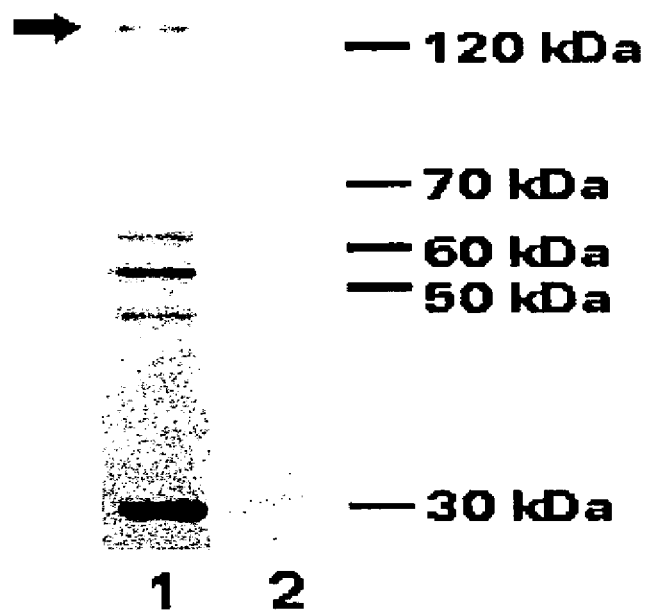
FIG. 3 Representative immunoblots of GCSF-R. Using the GCSF-R antiserum a band at about 130 kDa is detectable in tissue of the rat cortex (lane 1). Additional bands of lower molecular weight most probably reflect break down products. After preabsorption of the antiserum with the respective peptide, no bands are yet detectable (lane 2).
Figure 5:
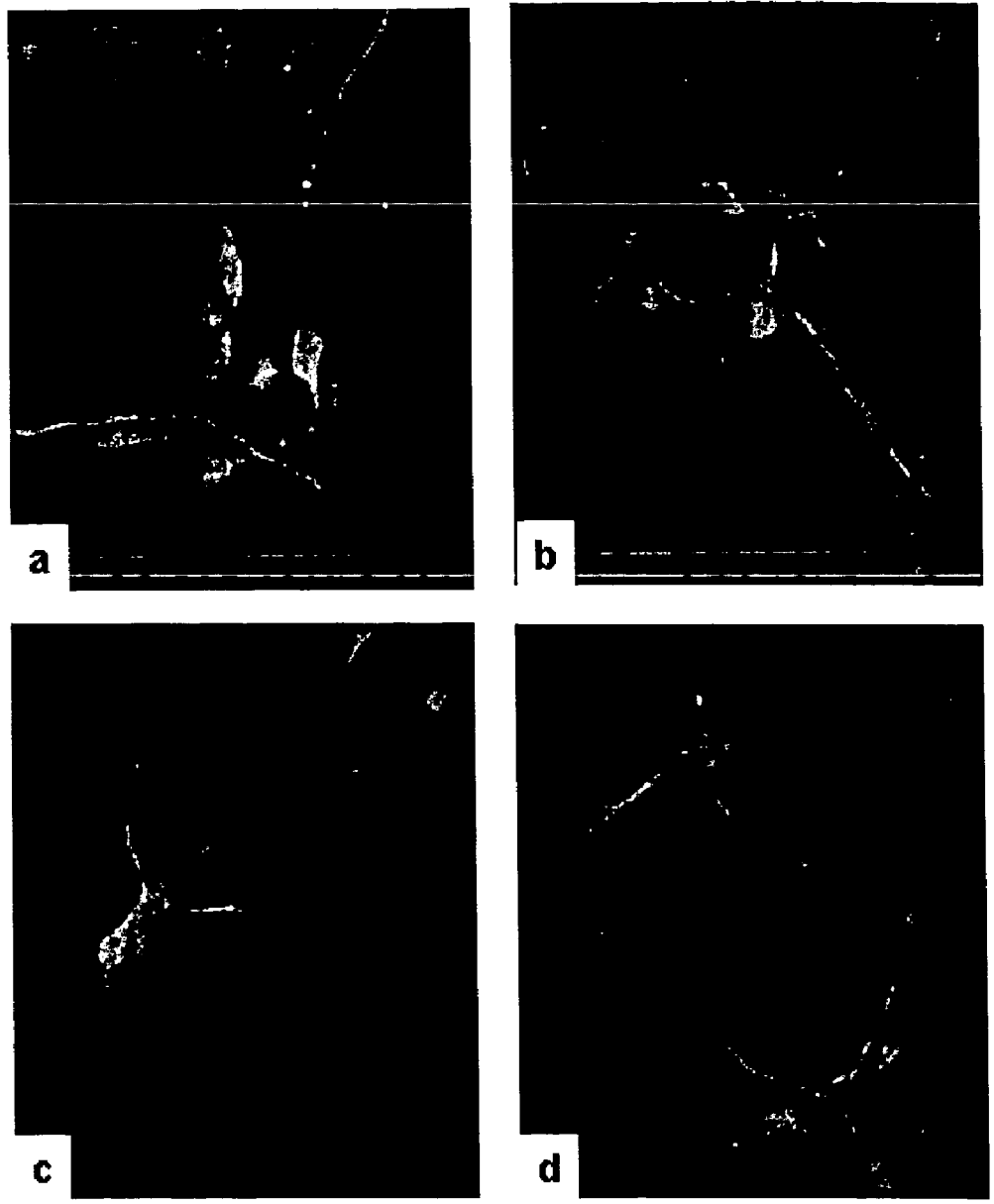
FIG. 5 shows a staining for the GCSFR on cortical (a, b) and hippocampal cultured neurons (c,d). The receptor is both present on the somata and processes of the neurons. Not all neurons on the slide were labelled. Preincubation of the antibody with the respective peptide, or omission of the primary antibody did not result in specific staining (not shown).

Western Blots (FIG. 3)

For immunoblotting, brain tissue (transient ischemia of 2 hours) was lysed in 20 volumes (w/v) of homogenization buffer (320 mM sucrose, 0.1 mM phenylmethylsulfonyl fluoride, and 2 µg/ml Pepstatin) at 4° C. Homogenates were centrifuged at 9,200 G for 15 min at 4° C. After resuspending pellets in ⅒ of the homogenization volume, aliquots for protein determination (Bio-Rad protein-assay, Munich, Germany) were separated and samples were rapidly frozen in nitric oxide and stored at −70° C. Per lane 15 µg protein were loaded on a 8% SDS polyacrylamide gel containing 4 M urea and electrophoresed under standard conditions. Proteins were electrophoretically transferred to Immobilon-P™ membranes (Millipore Corp., Eschborn, Germany) by semi-dry blotting. After blocking in 3% nonfat dry milk in TBST (20 mM Tris base, pH 7.6, 137 mM NaCl and 0.05% Tween-20) for 1 hour at room temperature (RT), membranes were incubated with the primary GCSFR antibody (1:500) overnight at 4° C. After washing in TBST the membranes were incubated for 1 hour at RT with 1:2,000 dilutions of the appropriate horseradish peroxidase-conjugated secondary antibody. Immunoreactive bands were visualized in the linear range with enhanced chemoluminescence (Amersham Intl., Braunschweig, Germany).

In immunoblotting experiments with cortical extracts (FIG. 3), the GCSF-R antiserum detected a protein band of approximately 130 kD, consistent with the deduced molecular weight (Fukunaga R, et al., *J Biol Chem* 1990; 265:14008-15). In addition, a few bands of lower molecular weight were seen, probably reflecting breakdown products. After preabsorption of the GCSFR antiserum with the respective peptide the bands disappeared (FIG. 3).

PCR for the GCSF Receptor in Brain (FIG. 2A)

After rats were deeply anesthetized and perfused transcardially, brains were rapidly dissected. RNA was extracted from brains by the RNA-clean kit (AGS, Heidelberg, Germany), according to the manufacturer's instructions. A total of 10 µg RNA was reverse transcribed with MMLV reverse transcriptase and random hexamers. For PCR, the following primers from exons 5 and 7 of the murine GCSFR were used: sense, 5'-CCC CTC AAA CCT ATC CTG CCT C-3' (SEQ ID NO:5); and antisense, 5'-TCC AGG CAG AGA TCA GCG AAT G-3' (SEQ ID NO:6). (Ashihara E, et al., *J Cell Physiol* 1997; 171:343-56). PCR was performed according to the following protocol: 3 min 94° C., 1 min 94° C., 1 min 58° C., and 1 min 72° C. (40 cycles). The product was analyzed on a 2% agarose gel.

Figure 2:
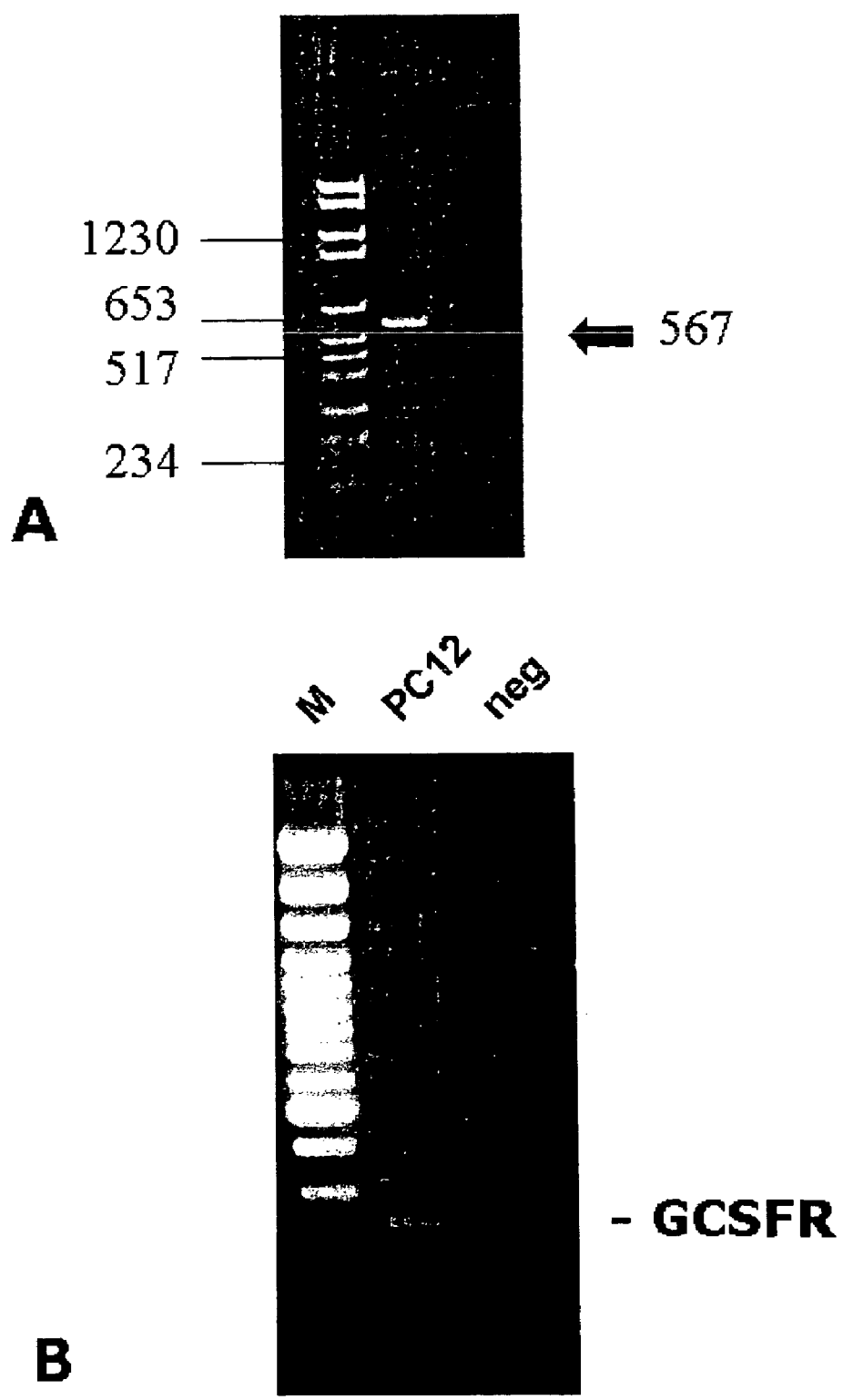
FIG. 2A shows a RT-PCR specific for the mouse GCSFR. GCSF-R RNA was detected in the brain tissue with the expected size of 567 bp. The identity was verified by sequencing the PCR product.
FIG. 2B shows G-CSF receptor is present on PC12 cells.

Using a RT-PCR specific for the mouse GCSFR, GCSF-R mRNA was detected in the brain tissue (FIG. 2A). The PCR product had the expected size of 567 bp. The identity was verified by sequencing the PCR product (FIG. 2).

Example 4

GCSF Efficacy in ALS Models

Survival Test in ALS Mouse Models

Previous experiments have demonstrated that SOD1 mouse models of ALS are predictive of the success of therapy in humans (Cleveland and Rothstein (2001), *Nat Rev Neurosci*, 2, 806-19). Primary endpoints in such analyses are both onset of motor signs, and mortality. For example, the onset of motor signs can be defined as the first day that a mouse can not remain on the rotarod for 7 min at a speed of 20 rpm (Li, et al (2000), *Science*, 288, 335-9). Mortality is scored as the day of death, or the day where deficits are so severe that the mouse has to be sacrificed (e.g. apathy and unability to right itself). Additional parameters are determined by the measurement of motor strength by grip strength tests, counts of motor neurons in the spinal cord, nerve thickness (e.g. sciatic nerve, phrenic nerve), and the presence of apoptotic stainings in spinal cord motor neurons. GCSF can be infused via an osmotic pump into the cerebral ventricles at a pre-determined dose, e.g. at 60 ug/kg body weight/day. Alternatively, GCSF is given via i.v. or i.p. injection at a dose of 60 ug/kg body weight per day, or higher doses. Alternatively, a slow-release form of GCSF is administered, such as a PEG formulation (see above), or an albumin formulation (see above), or other slow-release formulations. Alternatively, any GCSF or derivative or formulation of other source (another manufacturer (e.g. LENOGASTRIM™ from Roche, GRANOCYTE™ from Chugai Pharma, Co. Ltd., ALBUGRANIN™ from Human Genome Sciences, or NEULASTA™ from Roche/Amgen) is used.

Treatment is started at day 60 in the late presymptomatic stage of the SOD1 G93A mutant. In nontreated familial ALS mice, motor impairments appear at 12-14 weeks of age, whereas paralysis is not observed before 20 weeks of age. Life expectancy is 140-170 days. Effective treatment should prolong life as compared to the control group by more than 15% (Cleveland and Rothstein (2001), *Nat. Rev. Neurosci.*, 2, 806-19). As a control group for treatment, both vehicle and zVADfmk (a potent caspase inhibitor that has shown efficacy in this model) treated animals will be used. Each group comprises 10 animals each.

Example 5

GCSF Efficacy in Parkinson Models

There are various rodent models of Parkinson's disease available, that are suitable for efficacy studies of GCSF (Grunblatt et al. (2000), *J Neurol*, 247 Suppl 2, II95-102.). One well-characterized model is the use of 1-methyl-4-phenyl-1,2,3,6-tetrahydropyridine (MPTP). 4 doses of MPTP-HCl (15 mg/kg per dose) can be given to eight-week-old male mice (n=20) via i.p. injection at 2 hr intervals. Sham-treated animals receive saline. 20 animals receive both the MPTP treatment, and a daily dose of GCSF (i.v., 60 ug/kg bodyweight) seven days after the last MPTP treatment mice are sacrificed. Until that time, mice are analyzed both for motor parameters (rotarod performance, free locomotion). The brains of 10 mice each are processed for immunohistochemistry to assay the total number of neurons in the substantia nigra that are positive for tyrosine hydroxylase or the dopamine transporter (using commercially available antibodies), the number of apoptosis-positive neurons (TUNEL staining, caspase-3 staining). Remaining dopaminergic neurons after MPTP treatment are compared to those receiving MPTP plus GCSF, and to the sham group.

The remaining 10 animals in each group will be perfused transcardially with saline, sacrificed, and the striatum dissected out. The striatum will be homogenized on ice, and the dopamine content measured by HPLC with electrochemical detection. Comparison of the three groups will provide a good measure of dopamine depletion due to loss of cells in the substantia nigra.

This experiment can also be performed using different dosing schemes for MPTP (i.e. 40 mg/kg body weight once; 30 mg/kg body weight twice, etc.).

Example 6

GCSF Improves Sensory-Motor Function after Photothrombotic Cerebral Ischemia (FIG. 8)

Experimental Groups

Experimental protocols were approved by the local ethics committee. Male Wistar rats (Charles River, Germany) weighing 280 to 320 g were randomly assigned to the following groups: A (Control group, n=6), ischemia, treatment with 0.5 ml saline 0.9% as i.v. bolus infusion beginning 1 h after ischemia); B (GCSF group, n=6), ischemia, treatment with 5 µg GCSF (Amgen) soluted in 0.5 ml saline 0.9% as i.v. bolus beginning 1 h after ischemia. Alternatively, any GCSF or derivative or formulation of other source (another manufacturer (e.g. Lenogastrim™ by Roche or Granocyte™ by Chugai or Albugranin™ by HGS or Neulasta™ by Roche/Amgen) can be used here. Repetitive i.v. bolus infusions via the tail vene followed at day 1 to 5. C (sham operated group, n=6), sham operation, no ischemia, treatment with 0.5 ml saline 0.9% as i.v. bolus infusion beginning 1 h after ischemia.

Focal Cerebral Ischemia by Photothrombosis

Animals were anesthetized with an intramuscular injection of 100 mg/kg body weight ketaminehydrochloride (WDT, Garbsen, Germany). Anesthesia was maintained with 50 mg/kg body weight if necessary. A PE-50 polyethylene tube was inserted into the right femoral artery for continuous monitoring of mean arterial blood pressure, and blood gases. The right femoral vein was cannulated by a PE-50 tube for treatment infusion. During the experiment rectal temperature was monitored and maintained at 37° C. by a thermostatically controlled heating pad (Föhr Medical Intruments, Germany).

Photothrombotic ischemia was induced in the right rat parietal cortex according to the method of Watson et al. (Watson B D, Dietrich W D, Busto R, Wachtel M S, Ginsberg M D. Induction of reproducible brain infarction by photochemically initiated thrombosis. *Ann Neurol*. 1985; 17:497-504.). Animals were anesthetized with ketaminehydrochloride and placed in a stereotaxic frame, and the scalp was incised for exposure of the skull surface. For illumination, a fiber-optic bundle with a 1.5-mm aperture was placed stereotaxically onto the skull 4 mm posterior to the bregma and 4 mm lateral from the midline. The skull was illuminated with a cold, white light beam (150 W) for 20 minutes. During the first 2 minutes of illumination, the dye rose bengal (0.133 mL/kg body wt, 10 mg/mL saline) was injected intravenously. Sham-operated animals underwent the same experimental procedures as described above without infusion of rose bengal and illumination. After surgery, the catheters were removed, and the animals were allowed to recover from the anesthesia and given food and water ad libitum.

Behavioural Testing

In all animals a battery of behavioral tests was performed before ischemia and at baseline, 2, 3, 4, 5, and 6 weeks after ischemia by an investigator who was blinded to the experimental groups. For the rotarod test, rats were placed on an accelerating rotarod cylinder, and the time the animals remained on the rotarod was measured (Hamm et al, *J Neurotrauma* 1994 April; 11(2): 187-96, Chen J, Li Y, Wang L, Zhang Z, Lu D, Lu M, Chopp M. Therapeutic Benefit of Intravenous Administration of Bone Marrow Stromal Cells After Cerebral Ischemia in Rats. Stroke. 2001; 32:1005.). The speed was slowly increased from 4 to 40 rpm within 5 minutes. The trial ended if the animal fell off the rungs or gripped the device and spun around for 2 consecutive revolutions without attempting to walk on the rungs. An arbitrary limit of time was set for the rats at 500 seconds on the rotarod cylinder in training as well as in testing procedures. The animals were trained 3 days before ischemia. The mean duration (in seconds) on the device was recorded with 3 rotarod measurements 1 day before surgery. Motor test data are presented as percentage of mean duration (3 trials) on the rotarod compared with the internal baseline control (before surgery).

For the adhesive-removal test, somatosensory deficit was measured both before and after ischemia (Schallert T, Kozlowski D A, Humm J L, Cocke R R. Use-dependent structural events in recovery of function. Adv Neurol. 1997; 73:229-238.; Chen J, Li Y, Wang L, Zhang Z, Lu D, Lu M, Chopp M. Therapeutic Benefit of Intravenous Administration of Bone Marrow Stromal Cells After Cerebral Ischemia in Rats. Stroke. 2001; 32:1005.). All rats were familiarized with the testing environment. In the initial test, 2 small pieces of adhesive-backed paper dots (of equal size, 113.1 mm$^2$) were used as bilateral tactile stimuli occupying the distal-radial region on the wrist of each forelimb. The rat was then returned to its cage. The time to remove each stimulus from forelimbs was recorded on 5 trials per day for each forepaw. Individual trials were separated by at least 5 minutes. Before surgery, the animals were trained for 3 days. Once the rats were able to remove the dots within 10 seconds, they were subjected to ischemia.

Neurological Severity Scores (NSS) were modified according to Chen J, Li Y, Wang L, Zhang Z, Lu D, Lu M, Chopp M. Therapeutic Benefit of Intravenous Administration of Bone Marrow Stromal Cells After Cerebral Ischemia in Rats. Stroke. 2001; 32:1005., and Schallert T, Kozlowski D A, Humm J L, Cocke R R. Use-dependent structural events in recovery of function. Adv Neurol. 1997; 73:229-238. Neurological function was graded on a scale of 0 to 16 (normal score, 0; maximal deficit score, 16). NSS is a composite of motor, sensory, reflex, and balance tests (Chen J, Li Y, Wang L, Zhang Z, Lu D, Lu M, Chopp M. Therapeutic Benefit of Intravenous Administration of Bone Marrow Stromal Cells After Cerebral Ischemia in Rats. Stroke. 2001; 32:1005., Germano A F, Dixon C E, d'Avella D, Hayes R L, Tomasello F. Behavioral deficits following experimental subarachnoid hemorrhage in the rat. J Neurotrauma. 1994; 11:345-353.). In the severity scores of injury, 1 score point is awarded for the inability to perform the test or for the lack of a tested reflex; thus, the higher score, the more severe is the injury.

Results

No statistical differences were observed between the groups for rectal temperature, pH, $pCO_2$, $pO_2$, hematocrit (hct), blood glucose, heart rate, mean arterial pressure, body weight, and mortality for all animals (data not shown).

Functional recovery in GCSF treated animals was remarkably better over time compared with all other groups. GCSF treated animals had significantly lower NSS scores including Beam-Balance during the experiment compared to the control group (p<0.001, FIG. 8*b*), and resulted in significantly better rotarod performance compared to controls (P<0.05, FIG. 8*a*). Sensorimotor function as measured by adhesive tape removal was also better in GCSF treated animals on the contralateral forepaw over time compared to controls as well as on the ipsilateral forepaw at week 6 (see FIG. 8*c,d*).

Example 7

GCSF Receptor is Upregulated in the Photothrombotic Model of Cerebral Ischemia

RNA was isolated according to standard protocols (Chomczynski and Sacchi (1987), *Anal. Biochem.*, 162, 156-159), followed by Qiagen RNeasy™ mini kit purification from rat cortical penumbral samples, ipsi- and contralateral to the lesion side (see FIG. 9*a* for localization of the tissue samples; here: 3 vs. 4). cDNA was synthesized from 1 µg total RNA using oligodT primers, superscript II reverse transcriptase (Gibco) using standard conditions. Quantitative PCR was performed using the Lightcycler® system (Roche Diagnostics, Mannheim, Germany) with SYBR-green staining of DNA doublestrands. Cycling conditions were as follows: 5 min 95° C., 5 sec 95° C., 7 sec 66° C., 30 sec 72° C.; 9 sec 84° C. for 55 cycles. Melting curves were done with the following parameters: 95° C. cooling to 50° C.; ramping to 99° C. at 0.2° C./sec. The following primer pairs were used: "rat GCSFR-frag-32s" CCATTGTCCATCTTGGGGATC (SEQ ID NO:7), and "rat GCSFR-frag-265 as" CCTGGAAGCTGT-TGTTCCATG (SEQ ID NO:8). The Lightcycler® PCR was performed using the SYBR green master mix, following the manufacturer's recommendations (Roche Diagnostics). Specificity of product was ensured by melting point analysis and agarose gel electrophoresis. cDNA content of samples was normalized to the expression level of Cyclophilin (primers: "cyc5" ACCCCACCGTGTTCTTCGAC (SEQ ID NO:9); "acyc300" CATTTGCCATGGACAAGATG (SEQ ID NO:10)). Relative regulation levels were derived after normalization to cyclophilin, and comparison to the sham-operated animals. FIG. 9b shows upregulation of the GCSFR after 48 h on the contralateral side, error bars indicate standard deviations, these are calculated from 3-fold serially diluted cDNA-samples, and reflect reliability of measurements.

Example 8

GCSF Receptor is Present on Neuronal Cells in Primary Cultures: Immunocytochemistry Preparation of Neurons 10-12 Cortices were prepared from embryos of the stage E18 (embryonal day 18). Tissue was dissociated using trypsin [10 mg/ml]/EDTA/DNase [5 mg/ml] (Roche Diagnostics) in HBSS (Hanks balanced salt solution, BioWithakker). The digest was stopped using 4 parts medium (neurobasalmedium+1 ml 50×B-27 supplement (Invitrogen)+0.5 mM L-glutamin+25 µM glutamate) and centrifuged at room temperature for 5 min at 800 g. The pellet was dissolved in 5 ml medium and cell number determined by counting (Neubauer slide). The cells were plated at a density of 250 000 cells per well of a 24-well-plate on cover slips which were coated with poly-L-lysine.

Immunocytochemistry 14 days after preparation neurons were washed with PBS (Gibco) (37° C.) and fixed with 2% paraformaldehyde for 10 min on ice. Then, cells were washed with PBS (4° C.) and stored at 4° C. Cells were incubated for 10 min in 50 mM glycine in PBS, and then washed with PBS. Cells were permeabilised on ice using 0.2% TritonX-100 (Sigma) in PBS, and incubated with blocking solution (0.2% Triton-X100, 4% normal goat serum (NGS) (Jackson Immunoresearch Laboratories) in PBS) at room temperature. The primary antibody (rabbit-anti-GCSF-Rezeptor-antibody directed against the C-terminus of mouse GCSFR, M-20; sc-694; SantaCruz Biotechnology, Inc.) was used in a dilution of 1:800 (in 0.1% Triton-X100/2% NGS), and incubated overnight at 4° C. Cells were then washed with 1% NGS/PBS, and incubated for 30 min with the secondary antibody (anti-rabbit-FITC, 1:400; dianova) at room temperature. Cells were then washed briefly in 1% NGS/PBS, and stained with Hoechst 33342 (Molecular Probes) (1:10000 in PBS) for counterstaining the nuclei. Finally, cover slips were washed briefly twice in 1% NGS/PBS, twice in PBS, and once for 10 min in 10M Tris/HCl, pH 7.6. The cover slips were embedded using Aquamount (Polyscience).

Pictures were taken digitally with an Olympus IX81 microscope, and the "Analysis" software package (Soft Imaging Systems, Stuttgart, Germany).

Example 9

GCSF Receptor is Present on Neuronal Stem Cells: PCR and Immunocytochemistry (FIG. 12,13); GCSF Receptor is Present on PC12 Cells: PCR (FIG. 2B)

Generation of Neural Stem Cells

Neural stem cells were isolated from the brain areas with known spontaneous neurogenesis, i.e., hippocampus, olfactory bulb, and subventricular zone, of 4-6 week old male Wistar rats as described. (Ray J et al (1993), *Proc Natl Acad Sci USA* 90: 3602-6.). Protocols are concordant with the policy on the use of animals, as endorsed by the National Research Council of the U.S.A., and fulfill the requirements of German law. Briefly, animals were anesthesized with 1% (v/v) isoflurane, 70% N2O, 29% oxygen and sacrificed by decapitation. The brains were removed and washed in 50 mL ice-cold Dulbecco's Phosphate Buffered Saline (DPBS) supplemented with 4.5 g/L glucose (DPBS/Glc). Hippocampus, olfactory bulb, and subventricular zone from 6 animals were dissected, washed in 10 mL DPBS/Glc and centrifuged for 5 min at 1600×g at 4° C. After removal of the supernatant, the tissue was homogenized with scissors and scalpels. The tissue pieces were washed with DPBS/Glc medium for 5 min at 800 g, and the three pellets were resuspended in 0.01% (w/v) papain, 0.1% (w/v) dispase II (neutral protease), 0.01% (w/v) DNase I, and 12.4 mM manganese sulfate in Hank's Balanced Salt Solution (HBSS). The tissue was triturated with plastic pipet tips and incubated for 40 min at room temperature, but every 10 min the solution was mixed well. The suspension was centrifuged at 800×g for 5 min at 4° C. and pellets were washed three times in 10 mL DMEM-Ham's F-12 medium supplemented with 2 mM L-glutamine, 100 units/mL penicillin and 100 units/mL strepotomycin. Then, the cell pellets were resuspended in 1 mL Neurobasal medium supplemented with B27 (Invitrogen, Carlsbad, Calif., USA), 2 mM L-glutamine, 100 units/mL penicillin and 100 units/mL strepotomycin, 20 ng/mL EGF, 20 ng/mL FGF-2, and 2 µg/mL heparin. Cells were plated under sterile conditions in 6-well dishes in a concentration of 25,000-100,000 cells/mL. The dishes were incubated at 37° C. in 5% CO2. Cell culture media were changed once a week, where about two thirds of the media were replaced. (Ray J et al (1993), *Proc Natl Acad Sci U SA* 90: 3602-6.)

RT-PCR Protocol:

RNA was isolated according to standard protocols from hippocampal stem cells (FIG. 12) that were propagated 3 weeks in culture after thawing them from frozen stocks, following the manufacturer's recommendations (RNeasy kit, Qiagen). cDNA was synthesized using oligodT primers, Superscript II reverse transcriptase (Gibco) using standard conditions. Polymerase chain reaction (PCR) was performed with the following cycling conditions: 3 min 94°, 30 sec 94°, 30 sec 60°, 1 min 72°; for 32 cycles, using the primer pairs "rat GCSFR-frag-8s" GCGGGCAAATCAGGATCTCAC (SEQ ID NO:2), and "rat GCSFR-frag-287 as" CGAAGCT-CAGCTTGATCCAGG (SEQ ID NO:3). The primers were derived from a fragment of rat GCSFR identified from rat genomic databases by TBLASTX searches (see FIG. 1). Reaction conditions: 2 mM MgCl2, 200 uM dNTP, 200 nM each primer, 1 unit Taq Polymerase (Invitrogen)/25 µl. The PCR product was resolved on a 1.5% agarose gel. The specific PCR product length was 279 bp, with the following sequence (SEQ ID NO:4) (primer sequences are underlined):

```
gcgggcaaatcaggatctcaccccccattgtccatcttggggatcctgtcctggcctcctgcaccatcagcccaaactgcagcaaact ggaccgacagccaaagatcctatggagactgcaagatgaaccaaaccagcctggggacagacagcatcacctgcctgacgggtcccag gagtccatcatcactctgcctcatctgaactacactcaggccttcctcttctgcttggtgccatggaacaacagcttccaggtcctgg atcaagctgagcttcg.
```

For PCR on PC 12 cells (FIG. 2B), the above protocol was followed.

Immunocytochemistry of Neurospheres:

Neurospheres consisting of the neural stem cells were pipetted onto the glass slide, coverslip was put onto the cells, and the slide was put at −80° C. for at least 30 min. The coverslip was removed, and put into 4% PFA (paraformaldehyde) in 0.1 M Phosphatpuffer, pH 7.4 immediately. Cells were fixed for 20 min. Cells were washed 3×5 min in PBS (pH 7.4) with 1% FCS and 0.02% NaN$_3$. Cells were permeabilised for 10 min in PBS containing 0.5% TX-100. Antigens were blocked for 60 min in PBS (pH 7.4) containing 1% FCS and 0.02% NaN$_3$. Cells were stained for 12 min with the nuclear dye DAPI at a concentration of 0.001 mg/ml in PBS. Cells were then washed 2×5 min with PBS (pH 7.4) containing 1% FCS and 0.02% NaN$_3$. The first antibody was applied for 2 h diluted in PBS (pH 7.4) containing 1% FCS and 0.02% NaN$_3$, at concentrations of: anti-G-GSF 1:1000, anti-G-CSF-R 1:1000, anti-GM-CSF-R 1:1000 (Santa Cruz), respectively. Cells were washed for 3×5 min with PBS (pH 7.4) containing 1% FCS and 0.02% NaN$_3$. The second antibody (goat anti-rabbit IgG-FITC, (DAKO)) was then applied for 60 min in PBS (pH 7.4) containing 1% FCS and 0.02% NaN$_3$, at a concentration of 1:30. Cells were washed for 3×5 min in PBS (pH 7.4) containing 1% FCS and 0.02% NaN$_3$. Cells were finally mounted with Aquamount and coverslips.

Example 10

GMCSFR Alpha is Upregulated in the Phototrombotic Model of Cerebral Ischemia (Discovery by RMDD)

Experimental protocols were approved by the local ethics committee. Male Wistar rats (Charles River, Germany) weighing 280 to 320 g were assigned to the following treatments: a) ischemia for various timepoints (6 h, 48 h, and 21 d); b) sham operation, no ischemia, for accordant timepoints (6 h, 48 h, and 21 d), with n=2 for each timepoint and treatment.

Focal Cerebral Ischemia by Photothrombosis

Animals were anesthetized with an intramuscular injection of 20 mg/kg body weight ketaminehydrochloride (WDT, Garbsen, Germany). Anesthesia was maintained with 50 mg/kg body weight if necessary. A PE-50 polyethylene tube was inserted into the right femoral artery for continuous monitoring of mean arterial blood pressure, and blood gases. The right femoral vein was cannulated by a PE-50 tube for treatment infusion. During the experiment rectal temperature was monitored and maintained at 37° C. by a thermostatically controlled heating pad (Föhr Medical Intruments, Germany).

Photothrombotic ischemia was induced in the right rat parietal cortex according to the method of Watson B D, Dietrich W D, Busto R, Wachtel M S, Ginsberg M D. Induction of reproducible brain infarction by photochemically initiated thrombosis. Ann Neurol. 1985; 17:497-504. Animals were anesthetized with ketaminehydrochloride and placed in a stereotaxic frame, and the scalp was incised for exposure of the skull surface. For illumination, a fiber-optic bundle with a 1.5-mm aperture was placed stereotaxically onto the skull 4 mm posterior to the bregma and 4 mm lateral from the midline. The skull was illuminated with a cold, white light beam (150 W) for 20 minutes. During the first 2 minutes of illumination, the dye rose bengal (0.133 mL/kg body wt, 10 mg/mL saline) was injected intravenously. Sham-operated animals underwent the same experimental procedures as described above without infusion of rose bengal and illumination. After surgery, the catheters were removed, and the animals were allowed to recover from the anesthesia and given food and water ad libitum. Animals were killed according to the various timepoints (6 h, 48 h, and 21 d after ischemia and sham operation, respectively) and the preparation of the penumbral cortex both ipsi- and contralateral is known to those skilled in the art.

RNA Isolation and RMDD

RNA was isolated according to standard protocols (Chomczynski and Sacchi (*Anal Biochem* (1987), 162, 156-9), followed by Qiagen RNeasy mini kit purification) from rat cortical penumbral samples, ipsi- and contralateral to the lesion side (see FIG. 13a for localization of the tissue samples; here: 3 vs. 4). cDNA synthesis was performed from 1 µg total RNA according to the RMDD (restriction mediated differential display)-protocol as described in EP 0 743 367 A2 und U.S. Pat. No. 5,876,932. Following first strand and second strand synthesis, and MboI digestion an adaptor ligation was done. Two PCR reactions with subsets of primer combinations were performed. Subsequently the PCR reactions were loaded on a denaturing gel and blotted on a nylon membrane (GATC Biotech AG, Konstanz, Germany). Biotin-labeled bands were visualised with a common streptavidin-peroxidase reaction. PCR samples from the cortical penumbra were loaded on the gel in the following order: ipsilateral: naive (untreated), sham 6 h, sham 48 h, sham 21 d, and 6 h, 48 h and 21 d photothrombosis; contralateral: sham 6 h, sham 48 h, sham 21 d, and 6 h, 48 h and 21 d photothrombosis. Bands having different intensity in the ipsi- and contralateral region were cut out of the nylon membrane and reamplification of the according PCR product was performed. Amplified products were cloned in the pCR-BluntII-TOPO vector (Invitrogen GmbH, Karlsruhe, Germany) and sequenced with T7 and M13rev primers (ABI 3700). Obtained sequences were compared with the EMBL-database. A sequence upregulated after 48 h both in ipsi- and contralateral cortical penumbra was identified (FIG. 14). The identified EST-sequence was extended with BLASTN-searches in EST-databases and a mouse homologous sequence coding for the mouse GM-CSFR alpha was identified in EST- and genomic databases (ensembl; www.ensembl.org) by using screening programs (BLAST, TBLASTN (Altschul, et al. (1997), Nucleic Acids Res, 25, 3389-402.)).

Screens were performed in rat cDNA libraries with the PCR cloning method of Shepard ((1997) *Nucleic Acids Res* 25:3183-3185) to confirm the obtained rat sequence. This method is based on hybridization of cDNA molecules derived from a plasmid library to a biotin-coupled oligonucleotide sequence. Following plasmid extraction with streptavidin-coupled magnetic beads the result was ensured by diagnostic PCR and two fold replication of the steps following retransformation of the obtained plasmids until recovering the single clone. The following primer combinations were used:

```
5'block-2.clb4-4-4:   CGGGATCCGGGACCGCGTATCTGATGACGAGCGTGTCAA     (SEQ ID NO:12)

25bio-2.clb4-4-4:     CTCGGAGACGCTGAGGAAGGACCTG                   (SEQ ID NO:13)

3'block-2.clb4-4-4:   CTGCGGCCCTAGACCACGCCCACCGCTCCCCGTGACGTCG    (SEQ ID NO:14)
```

(The ORF was determined for the single clone and the sequence is shown as SEQ ID NO:40, the corresponding amino acid sequence is shown as SEQ ID NO:41).

Example 11

GMCSF Receptor Alpha is Upregulated in the Photothrombotic Model of Cerebral Ischemia (Verification by Quantitative PCR)

RNA was isolated according to standard protocols (Chomczynski and Sacchi (Anal Biochem (1987), 162, 156-9), followed by Qiagen RNeasy mini kit purification), from rat cortical penumbral samples, ipsi- and contralateral to the lesion side (see FIG. 13a for localization of the tissue samples; here: 3 vs. 4). cDNA was synthesized from 1 µg total RNA using oligodT primers, Superscript II reverse transcriptase (Gibco) using standard conditions. Quantitative PCR was performed using the Lightcycler system (Roche Diagnostics, Mannheim, Germany) with SYBR-green staining of DNA doublestrands. Cycling conditions were as follows: 5 min 95° C., 5 sec 95° C., 7 sec 62° C., 30 sec 72° C.; 9 sec 80° C. for 50 cycles. Melting curves were done with the following parameters: 95° C. cooling to 50° C.; ramping to 99° C. at 0.2° C./sec. The following primer pairs were used: "rat BR4-4s96" ACGTCGTTGGCTCAGTTATGTC (SEQ ID NO:15), and "rat BR4-4 as272" ATTTATGTCAGAGATGGAGGATGG (SEQ ID NO:16). The Lightcycler™ PCR was performed using the SYBR green master mix, following the manufacturer's recommendations (Roche diagnostics). Specificity of product was ensured by melting point analysis and agarose gel electrophoresis. cDNA content of samples was normalized to the expression level of Cyclophilin (primers: "cyc5" ACCCCACCGTGTTCTTCGAC (SEQ ID NO:17); "acyc300" CATTTGCCATGGACAAGATG (SEQ ID NO:18)). Relative regulation levels were derived after normalization to cyclophilin, and comparison to the sham-operated animals. FIG. 14a shows upregulation of the GMCSFR alpha after 48 h on the ipsi- and contralateral side. There is no significant regulation detectable 21 d after induction of photothrombosis (FIG. 14b). Error bars indicate standard deviations, these are calculated from 3-fold serially diluted cDNA-samples, and reflect reliability of measurements.

Example 12

GMCSF-Receptor Alpha is Present on Neuronal Cells in Primary Cortical Cultures: Preparation of Neurons 10-12 Cortices were prepared from embryos of the stage E18 (embryonal day 18). Tissue was dissociated using trypsin [10 mg/ml]/EDTA/DNase [5 mg/ml] (Roche diagnostics) in HBSS (Hanks balanced salt solution, BioWithakker). The digest was stopped using 4 parts medium (neurobasalmedium+1 ml 50×B-27 supplement (Invitrogen)+0.5 mM L-glutamin+25 µM glutamate) and centrifuged at room temperature for 5 min at 800×g. The pellet was dissolved in 5 ml medium and cell number determined by counting (Neubauer slide). The cells were plated at a density of 250 000 cells per well of a 24-well-plate on cover slips which were coated with poly-L-lysine.

Immunocytochemistry 1 week after preparation neurons were washed with PBS (Gibco) (37° C.) and fixed with 2% paraformaldehyde for 10 min on ice. Then, cells were washed with PBS (4° C.) and then incubated for 10 min in 50 mM glycine in PBS, then washed with PBS. Cells were permeabilized on ice using 0.2% TritonX-100 (Sigma) in PBS, and incubated with blocking solution (0.2% Triton-X100, 4% normal goat serum (NGS) (Jackson Immunoresearch Laboratories) in PBS) at room temperature. The primary antibody (rabbit-anti-GM-CSF-Receptor-antibody directed against the C-terminus of mouse GMCSFR, M-20; sc-691; SantaCruz) was used in a dilution of 1:300 (in 0.1% Triton-X100/2% NGS), and incubated overnight at 4° C. Cells were then washed with 1% NGS/PBS, and incubated for 30 min with the secondary antibody (anti-rabbit-FITC, 1:400; dianova) at room temperature. Cells were then washed briefly in 1% NGS/PBS, and stained with Hoechst 33342 (Molecular Probes) (1:10.000 in PBS) for counterstaining the nuclei. Finally, cover slips were washed briefly twice in 1% NGS/PBS, twice in PBS, and once for 10 min in 10 mM Tris/HCl, pH 7.6. The cover slips were embedded using Aquamount (Polyscience).

Pictures were taken digitally with an Olympus IX81 microscope, and the "Analysis" software package (Soft Imaging Systems, Stuttgart, Germany).

Example 13

GMCSF Receptor is Present on Neural Stem Cells: Generation of Neural Stem Cells (FIG. 13)

Neural stem cells were isolated from the brain areas with known spontaneous neurogenesis, i.e. hippocampus, olfactory bulb, and subventricular zone, of 4-6 week old male Wistar rats as described (Ray J et al (1993) Proc Natl Acad Sci USA 90: 3602-6.). Protocols are concordant with the policy on the use of animals, as endorsed by the National Research Council of the U.S.A., and fulfill the requirements of German law. Briefly, animals were anesthesized with 1% (v/v) isoflurane, 70% N2O, 29% oxygen and sacrificed by decapitation. The brains were removed and washed in 50 mL ice-cold Dulbecco's Phosphate Buffered Saline (DPBS) supplemented with 4.5 g/L glucose (DPBS/Glc). Hippocampus, olfactory bulb, and subventricular zone from 6 animals were dissected, washed in 10 mL DPBS/Glc and centrifuged for 5 min at 1600×g at 4° C. After removal of the supernatant, the tissue was homogenized with scissors and scalpels. The tissue pieces were washed with DPBS/Glc medium for 5 min at 800 g, and the three pellets were resuspended in 0.01% (w/v) papain, 0.1% (w/v) dispase II (neutral protease), 0.01% (w/v) DNase I, and 12.4 mM manganese sulfate in Hank's Balanced Salt Solution (HBSS). The tissue was triturated with plastic pipet tips and incubated for 40 min at room temperature, but every 10 min the solution was mixed well. The suspension was centrifuged at 800×g for 5 min at 4° C. and pellets were washed three times in 10 mL DMEM-Ham's F-12 medium supplemented with 2 mM L-glutamine, 100 units/mL penicillin and 100 units/mL strepotomycin. Then, the cell pellets were resuspended in 1 mL Neurobasal medium supplemented with B27 (Invitrogen, Carlsbad, Calif., USA), 2 mM L-glutamine, 100 units/mL penicillin and 100 units/nL strepotomycin, 20 ng/mL EGF, 20 ng/mL FGF-2, and 2 µg/mL heparin. Cells were plated under sterile conditions in 6-well dishes in a concentration of 25,000-100,000 cells/mL. The dishes were incubated at 37° C. in 5% CO2. Cell culture media were changed once a week, where about two thirds of the media were replaced. (Ray J et al (1993) *Proc Natl Acad Sci U SA* 90: 3602-6.)

RT-PCR Protocol

RNA was isolated according to standard protocols from hippocampal stem cells that were propagated 3 weeks in culture after thawing them from frozen stocks, following the manufacturers recommendations (RNeasy kit, Qiagen). cDNA was synthesized using oligodT primers, superscript II reverse transcriptase (Gibco) using standard conditions. Polymerase chain reaction (PCR) was performed with the following cycling conditions: 3 min 94°, 30 sec 94°, 30 sec 60°, 1 min 720; for 32 cycles, using the primer pairs "rat BR4-4s96" ACGTCGTTGGCTCAGTTATGTC (SEQ ID NO:19), and "rat BR4-4 as272" ATTTATGTCAGAGATG-GAGGATGG (SEQ ID NO:20). Reaction conditions: 2 mM MgCl2, 200 uM dNTP, 200 nM each primer, 1 unit Taq Polymerase (Invitrogen)/25 µl. PCR was resolved on a 1.5% agarose gel. The specific PCR product length was 176 bp with the following sequence (primer sequences are underlined):

<u>ACGTCGTTGGCTCAGTTATGTC</u>AGACAGGAAATCTCACCATCCCACAATGATTGAC    (SEQ ID NO:21)

AGCTCTCACAGGGAATCCCGCCTCCGCTGGGACCAATTGACATCACGGACAGGAAT

ACCCGCCCCTGTGGCCCTGATGGGCAGGTCCTGCCTGGCTC<u>CCATCCTCCATCTCT</u>

<u>GACATAAAT</u>

Example 14

Assay for Determining the Serum Half-Life and Passage of GCSF/GM-CSF through the Blood Brain Barrier It is desirable to know whether GCSF and GMCSF pass the blood-brain barrier. GCSF/GM-CSF are biotinylated to make use of the highly sensitive avidin-biotin-interaction for detection of the chemokines in brain tissue. G-CSF (Neupogen, Amgen) was biotinylated using Biotin-XX-SE (Molecular Probes B 1606). G-CSF was diluted into 20 mM sodium carbonate buffer pH 8 with 250 mM sorbitol and 0.004% Tween-80 and Biotin-XX-SE added. After 1 h at room temperature, Tris-buffer pH 8 was added to 50 mM concentration to quench unreacted labeling reagent. The sample was spun 30 min at 45000 rpm in a TLA 110 rotor (Beckman Instruments) to remove aggregates.

7.5 µg biotinylated G-CSF was injected into mice intraperitoneally at time zero (in 200 µl 20 mM sodium carbonate buffer pH 8 with 250 mM sorbitol and 0.004% Tween-80). Mice were anesthesized with chloralhydrate at times indicated and blood samples (approx 200 µl) were taken from the right heart chamber. EDTA was added to 5 mM and the sample centrifuged for 10 min at 1000 g to obtain serum. 4x sample buffer was added to serum, proteins denatured by heating to 95° C. for 5 min and 20 µl applied to a minigel. Proteins were transfered to nitrocellulose, blocked and incubated with Streptavidin-HRP (Amersham) in TBST. After washing, signals were detected using Pierce Supersignal chemiluminiscence reagent.

For Elisa analysis serum samples were diluted 1:20 in assay buffer and the assay performed according to the manufacturer's instructions (IBL, Hamburg, Germany).

This assay can be adapted accordingly to cerebrospinal fluid (csf) or brain homogenate to determine the transition of GCSF across the blood-brain-barrier.

Example 15

Assay for Neuroprotective Action of GCSF, GMCSF (FIG. 1b)

The neuroprotective action of GCSF/GMCSF was determined in vitro on NGF-treated PC12 cells. PC12 cells were seeded into 96 well plates coated with poly-1-lysine (0.01% final concentration) at a density of 40.000 cells/well. Cells were kept in DMEM medium containing 1000 mg glucose/l and 10% HS (horse serum) 5% FCS (fetal calf serum), 1% Penicillin/Streptomycin. Cells were then transfected with pSV40-RL (encoding the renilla luciferase gene) using the Lipofectamine2000® transfection agent (Gibco BRL) (0.2 ug DNA/well), following the manufacturers recommendations. Immediately after transfection, NGF (nerve growth factor) was added at a concentration of 40 ng/ml to induce differentiation of PC12 cells. At 24 h after treatment, PC12 cells develop a neuron-like morphology with extended processes. Cells were then treated with $H_2O_2$ at varying concentrations (FIG. 1b), and GCSF at varying concentrations (1-100 ng/ml). EPO was added as a positive control for a substance with known neuroprotective potency in vitro (Cerami, et al. (2002), Nephrol Dial Transplant, 17, 8-12., Kawakami, et al. (2001), J Biol Chem, 276, 39469-75., Sinor and Greenberg (2000), Neurosci Lett, 290, 213-5., Chong, et al. (2002), J Cereb Blood Flow Metab, 22, 503-14.) at concentrations of 0.01 U/ml to 1 U/ml. After 24 h, medium supernatant was discarded, and cells were lysed using the passive lysis buffer (Promega). Renilla luciferase activity was then recorded in a luminometer (Mithras, Berthold), and readings expressed as relative light units. This assay measures cell survival as the amount luciferase detectable. Therefore, the higher the relative light units, the more cells have survived. In this assay, GCSF showed a dose-dependent neuroprotection of PC12 cells, that was more potent than Erythropoetin.

Example 16

GCSF Receptor is Expressed in Various Brain Regions Important for Neurological Diseases (FIG. 4); GMCSF is Expressed in Various Important Brain Regions (FIG. 19)

To systematically assess the distribution of the GCSF receptor in the normal mouse brain, C57/b16 mice (2-3 months old) were anesthesized using an i.p. injection of Rompun® and Ketanest®. Mice were then transcardially perfused with 20 ml hanks balanced salt solution (HBSS), followed by 20 ml of 4% paraformaldehyde (PFA) in PBS (pH 7.4). The brain was dissected out, and stored overnight in 2% PFA solution. Paraffin-embedded tissues were sectioned (2 em), mounted on pre-treated slides (DAKO, Glostrup, Denmark), air-dried overnight and subsequently deparaffinized. After microwave treatment (citrate buffer; 500 W, 10 min), the anti-GCSFR antibody (1:400) was applicated and tissues were incubated for 1 h at room temperature in a moist chamber. Antibody labeling was visualized using the routine ABC technique and DAB as a chromogen following manufacturers recommendations (DAKO, Glostrup, Denmark). Negative controls included similarly processed sections in which the primary antibody had been totally omitted as well as sections where the appropriate normal serum was used (Dianova, Hamburg, Germany). Localization of GCSF-R was seen in the hippocampus (FIGS. 4a-d) with predominant staining of neurons in the CA3 area (FIG. 4a,b), with a sharp boundary between the CA3 and CA2 region (FIG. 4c, arrow). GCSF-R is distributed over the soma, as well as processes of neurons (FIG. 4b, arrow). The receptor is present in the hilus and the basal cell layers of the dentate gyrus (FIG. 4d, arrow). GCSF-Receptor was also detected in cortical areas: piriform cortex (FIG. 4e), and perirhinal cortex (f) as examples. In the cerebellum, Purkinje cells were labeled (FIG. 4g, arrow). Also, some of the large mitral cells in the olfactory bulb are GCSF-R positive (FIG. 4h, arrow). Strong staining is exhibited by the anterior columns in the spinal cord (FIG. 4i, j), and higher magnification identifies the large motoneurons as GCSF-R positive (FIG. 4k,l). Note that the neuronal processes are strongly labeled. In the midbrain, neurons in the substantia nigra show GCSF-R positivity (FIG. 4m,n,o). Apart from neurons, oligodendrocytes in white matter tracts are stained, for example, in the anterior commissure (FIG. 4, p, arrow).

The same example applies for the localization of the GMC-SFR (FIG. 19). Here, staining was seen in the hippocampus, in the cortex, in the cerebellum, and in the choroid plexus. Midbrain and spinal cord were not examined so far.

Example 17

Figure 23:
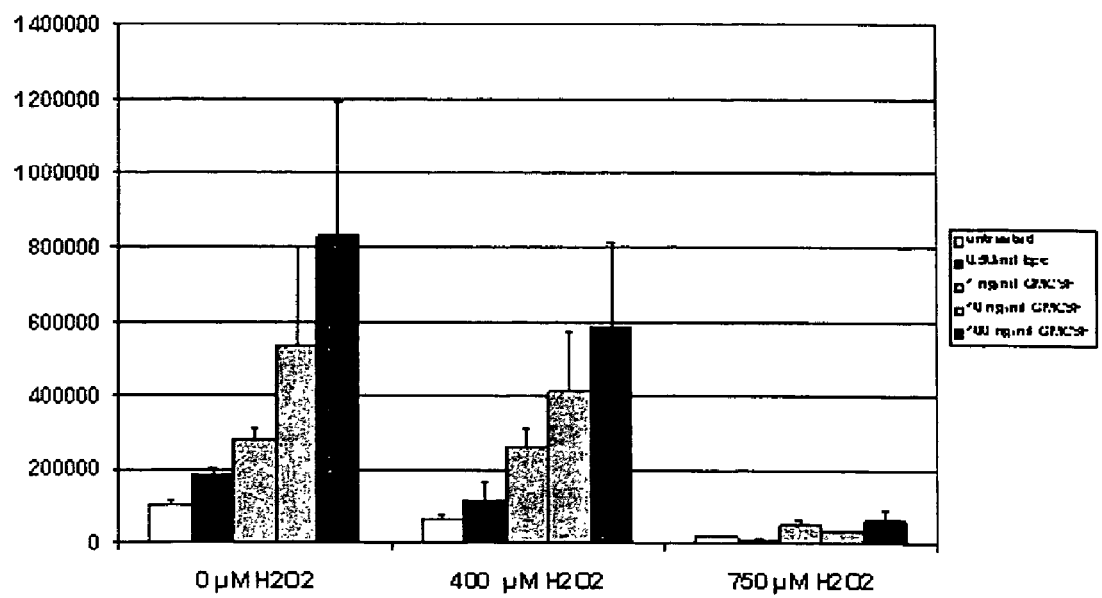
FIG. 23 demonstrates effective neuroprotection by GMCSF in vitro. Cell survival assay in NGF-treated PC12 cells under increasing oxidative stress by $H_2O_2$ (0 uM, 400 uM, 750 uM). GMCSF treatment produces dramatic increases in cell survival. In comparison, cell survival after treatment of the cells with Erythropoetin (EPO; 0.5 U/ml), a known neuroprotective substance, is given. Y-axis: Rel. cell survival (light units of luciferase activity).

Assay for Neuroprotective Action of GCSF, GMCSF (FIG. 1b, FIG. 23)

The neuroprotective action of GCSF/GMCSF was determined in vitro on NGF-treated PC12 cells. PC12 cells were seeded into 96 well plates coated with poly-1-lysine (0.01% final concentration) at a density of 40,000 cells/well. Cells were kept in DMEM medium containing 1000 mg glucose/1 and 10% HS (horse serum) 5% FCS (fetal calf serum), 1% Penicillin/Streptomycin. Cells were then transfected with pSV40-RL (encoding the renilla luciferase gene) using the Lipofectamine2000 transfection agent (Gibco BRL) (0.2 ug DNA/well), following the manufacturers recommendations. Immediately after transfection, NGF (nerve growth factor) was added at a concentration of 40 ng/ml to induce differentiation of PC12 cells. At 24 h after treatment, PC12 cells develop a neuron-like morphology with extended processes. Cells were then treated with $H_2O_2$ at varying concentrations (FIG. 1b, FIG. 23), and GCSF and GMCSF at varying concentrations (1-100 ng/ml). EPO was added as a positive control for a substance with known neuroprotective potency in vitro (Cerami et al. (2002), *Nephrol Dial Transplant*, 17, 8-12., Kawakami, et al. (2001), *J Biol Chem*, 276, 39469-75., Sinor and Greenberg (2000), *Neurosci Lett*, 290, 213-5., Chong, et al. (2002), *J Cereb Blood Flow Metab*, 22, 503-14.) at concentrations of 0.01 U/ml to 1 U/ml (FIG. 1b), or 0.5 U/ml (FIG. 23). After 24 h, medium supernatant was discarded, and cells were lysed using the passive lysis buffer (Promega). Renilla luciferase activity was then recorded in a luminometer (Mithras, Berthold), and readings expressed as relative light units. This assay measures cell survival as the amount luciferase detectable. Therefore, the higher the relative light units, the more cells have survived. In this assay, GCSF as well as GMCSF showed a dose-dependent neuroprotection of PC12 cells that was more potent than Erythropoetin.

Example 18

Thrombembolic Cerebral Ischemia

Experimental protocols will be approved by the local ethics committee. Forty male Wistar rats (Charles River, Germany) weighing 280 to 320 g will be randomly assigned to the following groups: A) early thrombolysis with 10 mg rt-PA/kg body weight for 1 hour, 1 hour after thrombembolic vessel occlusion; B late thrombolysis with 10 mg rt-PA/kg body weight for 1 hour, 3 hour after thrombembolic vessel occlusion; C) no thrombolysis, but treatment with 60 μg Ikg body weight of recombinant G-CSF (Neupogen®, Amgen, Europe B.V., Netherlands) in 2 ml saline 0.9% for 90 min beginning 30 min after thrombembolic ischemia; D) treatment with 60 μg/kg body weight of recombinant G-CSF (Neupogen®, Amgen, Europe B.V., Netherlands) in 2 ml saline 0.9% for 90 min beginning 30 min after thrombembolic ischemia combined with late thrombolysis with 10 mg rt-PA/kg body weight for 1 hour, 3 hour after thrombembolic vessel occlusion.

Animals will be anesthetized with an intraperitoneal injection of 100 mg/kg body weight ketaminehydrochloride (WDT, Garbsen, Germany). Anesthesia will be maintained with 50 mg/kg body weight, if necessary. A PE-50 polyethylene tube will be inserted into the right femoral artery for continuous monitoring of mean arterial blood pressure, blood gases, hematocrit, leukocyte count and blood glucose levels. The right femoral vein will be cannulated by a PE-50 tube for treatment infusion. During the experiment rectal temperature will be monitored and maintained at 37° C. by a thermostatically controlled heating pad (Föhr Medical Intruments, Germany).

Thromboembolic stroke will be induced according to the modified method described by Busch et al (*Brain Res* 1997 Dec. 5; 778(1):16-24). Briefly, the right common carotid (CCA), internal carotid (ICA) and external carotid arteries (ECA) will be exposed through a midline incision of the neck. Further dissection identified the origin of the pterygopalatine artery (PPA). The ECA and the PPA will be permanently ligated by a 6-0 silk suture. The CCA will be only temporarily ligated for the time of embolization. A catheter will be inserted into the ECA proximal to its ligation and 12 red blood clots (each 0.35 mm in diameter and 3 mm in length) were injected, resulting in embolization of the right middle cerebral artery (MCA).

Infarct evolution will be monitored by MR-imaging at 1, 2, 4, and 24 hours by using diffusion-, perfusion-, and T2-weighted imaging. In all animals, outcome will be measured by mortality as well as neurological outcome based on a five point scale 24 hours after ischemia. 24 hours after ischemia, the rats will be anesthetized with ketamine 150 mg/kg body weight and decapitated. The brains will be removed, and fixed with 4% paraformaldehyde in 0.1 mol/l phosphate buffer for 24 hrs. After paraffin-embedding, 1-μm-thick sections will becut and used for TTC, H&E, and Nissl staining and immuno-histochemical analysis.

Statistical Analysis

The values will be means±SD. After acquiring all the data, the randomization code will be broken. ANOVA and subsequent post hoc Fisher protected least significant difference test will be used to determine the statistical significance of differences in continuous variables such as physiological parameters, and infarct volume. The Mann-Whitney U test will be performed for nonparametric data such as the mortality rate. A p value <0.05 will be considered statistically significant.

All of the references cited herein, including patents, patent applications, and publications, are hereby incorporated in their entireties by reference.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of treating traumatic brain injury in a mammal suffering from traumatic brain injury, comprising
administering to the mammal suffering from traumatic brain injury, human G-CSF, or a protein having at least 90% homology to SEQ ID NO:38 in an amount sufficient to treat the traumatic brain injury; and
assessing neurological function in the mammal after said administering.

2. The method of claim 1, wherein human G-CSF is administered.

3. The method of claim 1, wherein the mammal treated is human.

4. The method of claim 1, wherein the human G-CSF, or a protein having at least 90% homology to SEQ ID NO:38 is administered by one or more modes of administration selected from the group consisting of direct intracerebral injection, intravenously, intraarterially, orally, and subcutaneously.

5. A method of treating traumatic brain injury in a mammal suffering from traumatic brain injury, comprising intravenously administering to the mammal suffering from traumatic brain injury, human G-CSF, or a protein having at least 90% homology to SEQ ID NO:38 in an amount sufficient to treat the traumatic brain injury; and
assessing neurological function in the mammal after said administering.

6. The method of claim 5, comprising intravenously administering human G-CSF.

7. The method of claim 5, comprising intravenously administering a protein having at least 90% homology to SEQ ID NO:38.

8. The method of claim 5, comprising intravenously administering a protein having at least 95% homology to SEQ ID NO:38.

9. The method of claim 1, wherein human G-CSF has the amino acid sequence in SEQ ID NO:37, SEQ ID NO:38, or SEQ ID NO:39.

10. The method of claim 5, wherein human G-CSF has the amino acid sequence in SEQ ID NO:37, SEQ ID NO:38, or SEQ ID NO:39.

11. The method of claim 9, wherein human G-CSF has the amino acid sequence in SEQ ID NO:38.

12. The method of claim 10, wherein human G-CSF has the amino acid sequence in SEQ ID NO:38.

13. A method of improving neurological function in a mammal suffering from traumatic brain injury, comprising administering to the mammal suffering from traumatic brain injury, human G-CSF, or a protein having at least 90% homology to SEQ ID NO:38 in an amount sufficient to improve neurological function compared to the mammal prior to administering; and assessing neurological function in the mammal after said administering.

14. The method of claim 13, wherein human G-CSF is administered.

15. The method of claim 13, wherein the mammal suffering from traumatic brain injury is human.

16. The method of claim 13, wherein the human G-CSF, or a protein having at least 90% homology to SEQ ID NO:38 is administered by one or more modes of administration selected from the group consisting of direct intracerebral injection, intravenously, intraarterially, orally, and subcutaneously.

17. The method of claim 16, wherein the mode of administration is intravenously.

18. The method of claim 13, wherein human G-CSF has the amino acid sequence in SEQ ID NO:37, SEQ ID NO:38, or SEQ ID NO:39.

19. The method of claim 18, wherein human G-CSF has the amino acid sequence in SEQ ID NO:38.

* * * * *